(12) United States Patent
Alimi et al.

(10) Patent No.: US 9,782,434 B2
(45) Date of Patent: *Oct. 10, 2017

(54) METHODS OF TREATING OR PREVENTING INFLAMMATION AND HYPERSENSITIVITY WITH OXIDATIVE REDUCTIVE POTENTIAL WATER SOLUTION

(71) Applicant: Oculus Innovative Sciences, Inc., Petaluma, CA (US)

(72) Inventors: Hojabr Alimi, Santa Rosa, CA (US); Andrés Gutiérrez, Petaluma, CA (US)

(73) Assignee: Sonoma Pharmaceuticals, Inc., Petaluma, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/793,649

(22) Filed: Jul. 7, 2015

(65) Prior Publication Data

US 2015/0306137 A1 Oct. 29, 2015

Related U.S. Application Data

(63) Continuation of application No. 12/643,191, filed on Dec. 21, 2009, now Pat. No. 9,072,726, which is a continuation of application No. 11/656,087, filed on Jan. 22, 2007, now abandoned.

(60) Provisional application No. 60/760,635, filed on Jan. 20, 2006, provisional application No. 60/760,567, filed on Jan. 20, 2006, provisional application No. 60/760,645, filed on Jan. 20, 2006, provisional application No. 60/760,557, filed on Jan. 20, 2006.

(51) Int. Cl.
| | |
|---|---|
| *A61K 33/00* | (2006.01) |
| *A61K 33/32* | (2006.01) |
| *A61P 17/00* | (2006.01) |
| *A61K 33/20* | (2006.01) |
| *A61K 33/40* | (2006.01) |
| *A61K 45/06* | (2006.01) |

(52) U.S. Cl.
CPC .............. *A61K 33/20* (2013.01); *A61K 33/00* (2013.01); *A61K 33/40* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 3,066,095 A | 11/1962 | Hronas | |
| 3,616,355 A | 10/1971 | Themy et al. | |
| 3,843,548 A | 10/1974 | James | |
| 3,949,742 A | 4/1976 | Nowakowski | |
| 3,975,246 A | 8/1976 | Eibl et al. | |
| 3,975,247 A | 8/1976 | Straiser | |
| 4,048,032 A | 9/1977 | Eibl | |
| 4,121,991 A | 10/1978 | Miller et al. | |
| 4,146,578 A | 3/1979 | Brennan et al. | |
| 4,190,638 A | 2/1980 | Hoekje et al. | |
| 4,236,992 A | 12/1980 | Themy | |
| 4,242,446 A | 12/1980 | Madappally et al. | |
| 4,289,599 A | 9/1981 | Fushihara | |
| 4,296,103 A | 10/1981 | Laso | |
| 4,382,441 A | 5/1983 | Svedman | |
| 4,615,937 A | 10/1986 | Bouchette | |
| 4,666,621 A | 5/1987 | Clark et al. | |
| 4,670,252 A | 6/1987 | Sampathkumar | |
| 4,693,832 A | 9/1987 | Hurst | |
| 4,767,511 A | 8/1988 | Aragon | |
| 4,781,974 A | 11/1988 | Bouchette et al. | |
| 4,839,004 A | 6/1989 | Castellini | |
| 4,970,216 A | 11/1990 | Deckner et al. | |
| 4,979,938 A | 12/1990 | Stephen et al. | |
| 5,037,627 A | 8/1991 | Melton et al. | |
| 5,063,922 A | 11/1991 | Hakkinen | |
| 5,079,010 A | 1/1992 | Natterer | |
| 5,084,011 A | 1/1992 | Grady | |
| 5,126,057 A | 6/1992 | Worley et al. | |
| 5,128,136 A | 7/1992 | Bentley et al. | |
| 5,152,757 A | 10/1992 | Eriksson | |
| 5,152,915 A | 10/1992 | Ralston, Jr. et al. | |
| 5,165,910 A | 11/1992 | Oikawa et al. | |
| 5,244,768 A | 9/1993 | Inaba | |
| 5,271,943 A | 12/1993 | Bogart et al. | |
| 5,287,847 A | 2/1994 | Piper et al. | |

(Continued)

FOREIGN PATENT DOCUMENTS

| | | |
|---|---|---|
| CN | 1 231 994 A | 10/1999 |
| CN | 1 487 835 A | 4/2004 |

(Continued)

OTHER PUBLICATIONS

Nathan, Nature, 2002, 420, pp. 846-852.*
Theoharides et al., Endocrinology, 1998, 139(1), 403-413.*
Douglass et al., MJA Practice Essentials-Allergy, 2006, 185, 228-233.*
The Merck Manual, 2006, www.merck.com/mmhe/print/sec16/ch185/ch185a.html, obtained online Jun. 16, 2009, pp. 1-6.*
MyVMC.com, Oct. 8, 2005, obtained online at myvmc.com/diseases/hypersensitivity-reaction-type-i/, downloaded on Sep. 28, 2016.*

(Continued)

*Primary Examiner* — Abigail Vanhorn
(74) *Attorney, Agent, or Firm* — Leydig, Voit & Mayer, Ltd.

(57) ABSTRACT

Provided is a method for preventing or treating inflammation and associated states (e.g. infection, hypersensitivity, pain) by administering a therapeutically effective amount of an oxidative reduction potential (ORP) water solution that is stable for at least about twenty-four hours. The ORP water solution administered in accordance with the invention can be combined with one or more suitable carriers and can be administered in conjunction with one or more additional therapeutic agents.

13 Claims, 17 Drawing Sheets

(56) References Cited

U.S. PATENT DOCUMENTS

| | | |
|---|---|---|
| 5,312,281 A | 5/1994 | Takahashi et al. |
| 5,334,383 A | 8/1994 | Morrow |
| 5,376,242 A | 12/1994 | Hayakawa |
| 5,388,571 A | 2/1995 | Roberts et al. |
| 5,427,667 A | 6/1995 | Bakhir et al. |
| 5,445,722 A | 8/1995 | Yamaguti et al. |
| 5,449,442 A | 9/1995 | Yamada et al. |
| 5,474,662 A | 12/1995 | Miyamae |
| 5,507,932 A | 4/1996 | Robinson |
| 5,510,009 A | 4/1996 | Arai et al. |
| 5,543,030 A | 8/1996 | Shiramizu et al. |
| 5,545,374 A | 8/1996 | French et al. |
| 5,560,816 A | 10/1996 | Robinson |
| 5,578,022 A | 11/1996 | Scherson et al. |
| 5,593,554 A | 1/1997 | Yamanaka et al. |
| 5,599,438 A | 2/1997 | Shiramizu et al. |
| 5,615,764 A | 4/1997 | Satoh |
| 5,616,221 A | 4/1997 | Aoki et al. |
| 5,620,587 A | 4/1997 | Nakamura |
| 5,622,725 A | 4/1997 | Kross |
| 5,622,848 A | 4/1997 | Morrow |
| 5,624,535 A | 4/1997 | Tsuchikawa et al. |
| 5,624,544 A | 4/1997 | Deguchi et al. |
| 5,628,888 A | 5/1997 | Bakhir et al. |
| 5,635,040 A | 6/1997 | Bakhir et al. |
| 5,635,053 A | 6/1997 | Aoki et al. |
| 5,636,643 A | 6/1997 | Argenta et al. |
| 5,639,441 A * | 6/1997 | Sievers ............. A61K 9/0073 128/200.23 |
| 5,662,625 A | 9/1997 | Westwood |
| 5,674,365 A | 10/1997 | Sano |
| 5,674,537 A | 10/1997 | Morrow |
| 5,720,869 A | 2/1998 | Yamanaka et al. |
| 5,728,274 A | 3/1998 | Kamitani et al. |
| 5,728,287 A | 3/1998 | Hough et al. |
| 5,731,008 A | 3/1998 | Morrow |
| 5,736,027 A | 4/1998 | Nakamura |
| 5,759,489 A | 6/1998 | Miura et al. |
| 5,762,779 A | 6/1998 | Shiramizu et al. |
| 5,783,052 A | 7/1998 | Bakhir et al. |
| 5,792,090 A | 8/1998 | Ladin |
| 5,798,028 A | 8/1998 | Tsuchikawa et al. |
| 5,833,831 A | 11/1998 | Kitajima et al. |
| 5,843,291 A | 12/1998 | Eki et al. |
| 5,858,201 A | 1/1999 | Otsuka et al. |
| 5,858,202 A | 1/1999 | Nakamura |
| 5,871,623 A | 2/1999 | Dakhir et al. |
| 5,876,743 A | 3/1999 | Ibsen et al. |
| 5,888,357 A | 3/1999 | Mitsumori et al. |
| 5,888,528 A | 3/1999 | Wellinghoff et al. |
| 5,897,757 A | 4/1999 | Sano |
| 5,900,257 A | 5/1999 | Breton et al. |
| 5,902,619 A | 5/1999 | Rubow et al. |
| 5,906,810 A | 5/1999 | Turner |
| 5,908,707 A | 6/1999 | Cabell et al. |
| 5,919,129 A | 7/1999 | Vandre |
| 5,928,488 A | 7/1999 | Newman |
| 5,928,491 A | 7/1999 | Yu et al. |
| 5,932,171 A | 8/1999 | Malchesky |
| 5,938,915 A | 8/1999 | Morisawa |
| 5,938,916 A | 8/1999 | Bryson et al. |
| 5,941,859 A | 8/1999 | Lerman |
| 5,944,978 A | 8/1999 | Okazaki |
| 5,948,220 A | 9/1999 | Kamitani et al. |
| 5,951,859 A | 9/1999 | Miura et al. |
| 5,963,435 A | 10/1999 | Biernson |
| 5,964,089 A | 10/1999 | Murphy et al. |
| 5,965,009 A | 10/1999 | Shimamune et al. |
| 5,980,703 A | 11/1999 | Yamada et al. |
| 5,985,110 A | 11/1999 | Bakhir et al. |
| 5,993,639 A | 11/1999 | Miyashita et al. |
| 5,997,717 A | 12/1999 | Miyashita et al. |
| 6,007,686 A | 12/1999 | Welch et al. |
| 6,007,693 A | 12/1999 | Silveri |
| 6,007,696 A | 12/1999 | Takayasu et al. |
| 6,033,539 A | 3/2000 | Gablenko |
| 6,056,866 A | 5/2000 | Maeda et al. |
| 6,059,941 A | 5/2000 | Bryson et al. |
| 6,093,292 A | 7/2000 | Akiyama |
| 6,106,691 A | 8/2000 | Nakamura et al. |
| 6,117,285 A | 9/2000 | Welch et al. |
| 6,121,317 A | 9/2000 | Wu et al. |
| 6,126,796 A | 10/2000 | Shimamune et al. |
| 6,126,810 A | 10/2000 | Fricker et al. |
| 6,139,876 A | 10/2000 | Kolta |
| 6,143,163 A | 11/2000 | Sawamoto et al. |
| 6,149,780 A | 11/2000 | Miyake |
| 6,171,551 B1 | 1/2001 | Malchesky et al. |
| 6,174,419 B1 | 1/2001 | Akiyama |
| 6,187,154 B1 | 2/2001 | Yamaguchi et al. |
| 6,197,814 B1 | 3/2001 | Arata et al. |
| 6,200,434 B1 | 3/2001 | Shinjo et al. |
| 6,210,748 B1 | 4/2001 | Nagahara et al. |
| 6,228,251 B1 | 5/2001 | Okazaki |
| 6,231,747 B1 | 5/2001 | Fukuzuka et al. |
| 6,231,878 B1 | 5/2001 | Komatu et al. |
| 6,245,210 B1 | 6/2001 | Nakamura et al. |
| 6,251,259 B1 | 6/2001 | Satoh et al. |
| 6,258,225 B1 | 7/2001 | Yamaoka |
| 6,277,266 B1 | 8/2001 | Yamaoka |
| 6,280,594 B1 | 8/2001 | Yamaoka |
| 6,294,073 B1 | 9/2001 | Shirota et al. |
| 6,296,744 B1 | 10/2001 | Djeiranishvili et al. |
| 6,333,054 B1 | 12/2001 | Rogozinski |
| 6,340,663 B1 | 1/2002 | Deleo et al. |
| 6,342,150 B1 | 1/2002 | Sale et al. |
| 6,350,376 B1 | 2/2002 | Imaoka et al. |
| 6,358,395 B1 | 3/2002 | Schorzman et al. |
| 6,361,665 B1 | 3/2002 | Vorack |
| 6,368,592 B1 | 4/2002 | Colton et al. |
| 6,375,809 B1 | 4/2002 | Kato et al. |
| 6,384,363 B1 | 5/2002 | Hayakawa et al. |
| 6,391,169 B1 | 5/2002 | Hara et al. |
| 6,426,066 B1 | 7/2002 | Najafi et al. |
| 6,436,445 B1 | 8/2002 | Hei et al. |
| 6,444,255 B2 | 9/2002 | Nagahara et al. |
| 6,462,250 B1 | 10/2002 | Kuriyama et al. |
| 6,464,845 B2 | 10/2002 | Shirota et al. |
| 6,475,371 B1 | 11/2002 | Shirahata et al. |
| 6,506,416 B1 | 1/2003 | Oakauchi et al. |
| 6,527,940 B1 | 3/2003 | Shimamune et al. |
| 6,544,502 B2 * | 4/2003 | Heesch ............. A61K 9/0014 424/176.1 |
| 6,551,492 B2 | 4/2003 | Hanaoka |
| 6,565,736 B2 | 5/2003 | Park et al. |
| 6,585,867 B1 | 7/2003 | Asano |
| 6,585,868 B1 | 7/2003 | Chihara |
| 6,598,602 B1 | 7/2003 | Sjoholm |
| 6,620,315 B2 | 9/2003 | Martin |
| 6,623,615 B1 * | 9/2003 | Morisawa ............. C02F 1/4602 204/257 |
| 6,623,695 B2 | 9/2003 | Malchesky et al. |
| 6,624,135 B2 | 9/2003 | Takano |
| 6,632,347 B1 | 10/2003 | Buckley et al. |
| 6,638,364 B2 | 10/2003 | Harkins et al. |
| 6,638,413 B1 | 10/2003 | Weinberg et al. |
| 6,663,306 B2 | 12/2003 | Policicchio et al. |
| 6,716,335 B2 | 4/2004 | Takesako et al. |
| 6,723,226 B1 | 4/2004 | Takayasu et al. |
| 6,733,435 B2 | 5/2004 | Canedo |
| 6,743,351 B1 | 6/2004 | Arai et al. |
| 6,752,757 B2 | 6/2004 | Muir et al. |
| 6,767,342 B1 | 7/2004 | Cantwell |
| 6,793,846 B2 | 9/2004 | Yoshikawa et al. |
| 6,815,551 B2 | 11/2004 | Albiez et al. |
| 6,823,609 B2 | 11/2004 | Moretti |
| 6,827,849 B2 | 12/2004 | Kurokawa et al. |
| 6,833,206 B2 | 12/2004 | Erdle et al. |
| 6,833,207 B2 | 12/2004 | Joos et al. |
| 6,838,210 B2 | 1/2005 | Sawa |
| 6,843,448 B2 | 1/2005 | Parmley |
| 6,844,026 B2 | 1/2005 | Anthony et al. |
| 6,852,205 B1 | 2/2005 | Toyoshima et al. |
| 6,855,233 B2 | 2/2005 | Sawada |

(56) References Cited

U.S. PATENT DOCUMENTS

| | | | |
|---|---|---|---|
| 6,855,307 B2 | 2/2005 | Shane et al. | |
| 6,855,490 B2 | 2/2005 | Sompuram et al. | |
| 6,856,916 B2 | 2/2005 | Shyu | |
| 6,866,756 B2 | 3/2005 | Klein | |
| 6,867,048 B2 | 3/2005 | Kovacs | |
| 6,874,675 B2 | 4/2005 | Kida et al. | |
| 6,887,601 B2 | 5/2005 | Moulthrop et al. | |
| 6,899,903 B2 | 5/2005 | Quillin | |
| 6,921,743 B2 | 7/2005 | Scheder et al. | |
| 6,923,893 B2 | 8/2005 | Sano | |
| 7,090,753 B2 | 8/2006 | Sumita | |
| 7,276,051 B1 | 10/2007 | Henley et al. | |
| 7,276,255 B2 | 10/2007 | Selkon | |
| 7,393,522 B2 | 7/2008 | Najafi et al. | |
| 7,749,370 B2 | 7/2010 | Sumita | |
| 7,758,807 B2 | 7/2010 | Smith et al. | |
| 8,062,500 B2 | 11/2011 | Sumita | |
| 8,147,444 B2 | 4/2012 | Alimi et al. | |
| 8,323,252 B2 | 12/2012 | Alimi et al. | |
| 8,784,900 B2 | 7/2014 | Northey | |
| 8,834,445 B2 | 9/2014 | Alimi et al. | |
| 8,840,873 B2 | 9/2014 | Alimi | |
| 9,072,726 B2 * | 7/2015 | Alimi | A61K 33/00 |
| 9,168,318 B2 * | 10/2015 | Alimi | A01N 59/00 |
| 2001/0012544 A1 | 8/2001 | Nagahara et al. | |
| 2001/0022273 A1 | 9/2001 | Popov et al. | |
| 2002/0006961 A1 | 1/2002 | Katz et al. | |
| 2002/0023847 A1 | 2/2002 | Natsume | |
| 2002/0027070 A1 | 3/2002 | Oyokota et al. | |
| 2002/0027079 A1 | 3/2002 | Hanaoka | |
| 2002/0027084 A1 | 3/2002 | Park et al. | |
| 2002/0032141 A1 | 3/2002 | Harkins | |
| 2002/0036134 A1 | 3/2002 | Shirota et al. | |
| 2002/0064565 A1 | 5/2002 | Karagoezian | |
| 2002/0074237 A1 | 6/2002 | Takesako et al. | |
| 2002/0082196 A1 | 6/2002 | Zaveri | |
| 2002/0082566 A1 | 6/2002 | Stenzler | |
| 2002/0112314 A1 | 8/2002 | Harkins | |
| 2002/0134691 A1 | 9/2002 | Satoh et al. | |
| 2002/0135220 A1 | 9/2002 | Yamaguchi et al. | |
| 2002/0160053 A1 | 10/2002 | Yahagi et al. | |
| 2002/0165220 A1 | 11/2002 | Heesch | |
| 2002/0165431 A1 | 11/2002 | Muir et al. | |
| 2002/0168418 A1 | 11/2002 | Lorenz et al. | |
| 2002/0175085 A1 | 11/2002 | Harkins et al. | |
| 2002/0176885 A1 | 11/2002 | Najafi et al. | |
| 2002/0179884 A1 | 12/2002 | Hoshino et al. | |
| 2002/0182262 A1 | 12/2002 | Selkon | |
| 2003/0015418 A1 | 1/2003 | Tseng et al. | |
| 2003/0019764 A1 | 1/2003 | Baldwin et al. | |
| 2003/0024828 A1 | 2/2003 | Kondo et al. | |
| 2003/0045502 A1 | 3/2003 | Kataoka et al. | |
| 2003/0049163 A1 | 3/2003 | Malchesky et al. | |
| 2003/0056805 A1 | 3/2003 | Sumita | |
| 2003/0062068 A1 | 4/2003 | Ko et al. | |
| 2003/0064427 A1 | 4/2003 | Felkner et al. | |
| 2003/0087427 A1 | 5/2003 | Colton et al. | |
| 2003/0089618 A1 | 5/2003 | Satoh et al. | |
| 2003/0098283 A1 | 5/2003 | Katayose et al. | |
| 2003/0138496 A1 | 7/2003 | Teng et al. | |
| 2003/0141200 A1 | 7/2003 | Harada | |
| 2003/0155549 A1 | 8/2003 | Yoshikawa et al. | |
| 2003/0175220 A1 | 9/2003 | Wang et al. | |
| 2003/0185704 A1 | 10/2003 | Bernard et al. | |
| 2003/0212005 A1 | 11/2003 | Petito et al. | |
| 2003/0219361 A1 | 11/2003 | Lee et al. | |
| 2003/0230826 A1 | 12/2003 | Kawaguchi et al. | |
| 2004/0004007 A1 | 1/2004 | Orolin et al. | |
| 2004/0011665 A1 | 1/2004 | Koizumi et al. | |
| 2004/0029761 A1 | 2/2004 | Wakamatsu et al. | |
| 2004/0037737 A1 | 2/2004 | Marais et al. | |
| 2004/0055896 A1 | 3/2004 | Anderson et al. | |
| 2004/0060815 A1 | 4/2004 | Buckley et al. | |
| 2004/0062818 A1 | 4/2004 | Calderon | |
| 2004/0079791 A1 | 4/2004 | Kida et al. | |
| 2004/0081705 A1 | 4/2004 | Gotou | |
| 2004/0084325 A1 | 5/2004 | Weinberg et al. | |
| 2004/0084326 A1 | 5/2004 | Weinberg et al. | |
| 2004/0094406 A1 | 5/2004 | Sawada | |
| 2004/0131695 A1 | 7/2004 | Hinze | |
| 2004/0137078 A1 | 7/2004 | Najafi et al. | |
| 2004/0154993 A1 | 8/2004 | Yanagihara et al. | |
| 2004/0168909 A1 | 9/2004 | Larson | |
| 2004/0168933 A1 | 9/2004 | Inoue | |
| 2004/0171701 A1 | 9/2004 | Shaw | |
| 2004/0171998 A1 | 9/2004 | Marasco, Jr. | |
| 2004/0172985 A1 | 9/2004 | Mamiya et al. | |
| 2004/0177655 A1 | 9/2004 | Kodera et al. | |
| 2004/0185311 A1 | 9/2004 | Muthuswamy et al. | |
| 2004/0185313 A1 | 9/2004 | Halter et al. | |
| 2004/0188248 A1 | 9/2004 | Sawa | |
| 2004/0208940 A1 | 10/2004 | Selkon | |
| 2004/0226894 A1 | 11/2004 | Okazaki | |
| 2004/0231977 A1 | 11/2004 | Roselle et al. | |
| 2004/0244537 A1 | 12/2004 | Runyon | |
| 2004/0250323 A1 | 12/2004 | Arai et al. | |
| 2004/0254744 A1 | 12/2004 | Shyu | |
| 2004/0256317 A1 | 12/2004 | Yamada et al. | |
| 2004/0265394 A1 | 12/2004 | Morris et al. | |
| 2005/0000117 A1 | 1/2005 | Polegato Moretti | |
| 2005/0054973 A1 | 3/2005 | Constantz et al. | |
| 2005/0058013 A1 | 3/2005 | Warf et al. | |
| 2005/0062289 A1 | 3/2005 | Cho et al. | |
| 2005/0064259 A1 | 3/2005 | Coors | |
| 2005/0067300 A1 | 3/2005 | Tremblay et al. | |
| 2005/0074421 A1 | 4/2005 | Tanaka | |
| 2005/0075257 A1 | 4/2005 | Scheper et al. | |
| 2005/0101838 A1 | 5/2005 | Camillocci et al. | |
| 2005/0109610 A1 | 5/2005 | Inamoto et al. | |
| 2005/0113276 A1 | 5/2005 | Taylor et al. | |
| 2005/0121334 A1 | 6/2005 | Sumita | |
| 2005/0126927 A1 | 6/2005 | Lindauer et al. | |
| 2005/0126928 A1 | 6/2005 | Hung et al. | |
| 2005/0129996 A1 | 6/2005 | Moulthrop et al. | |
| 2005/0139465 A1 | 6/2005 | Kasuya et al. | |
| 2005/0139808 A1 | 6/2005 | Alimi | |
| 2005/0142157 A1 * | 6/2005 | Alimi | A01N 59/00 424/405 |
| 2005/0153858 A1 | 7/2005 | Anthony et al. | |
| 2005/0155863 A1 | 7/2005 | Kovacs et al. | |
| 2005/0161950 A1 | 7/2005 | Borden et al. | |
| 2005/0178349 A1 | 8/2005 | Tse | |
| 2005/0178920 A1 | 8/2005 | Wilson | |
| 2005/0180925 A1 | 8/2005 | Chaudry | |
| 2005/0183949 A1 | 8/2005 | Daly et al. | |
| 2005/0183964 A1 | 8/2005 | Roberts et al. | |
| 2005/0189234 A1 | 9/2005 | Gibson et al. | |
| 2005/0189237 A1 | 9/2005 | Sano | |
| 2005/0191372 A1 | 9/2005 | Stenzler et al. | |
| 2005/0196462 A1 | 9/2005 | Alimi | |
| 2005/0198963 A1 | 9/2005 | Wai et al. | |
| 2005/0209518 A1 | 9/2005 | Sage et al. | |
| 2005/0228046 A1 | 10/2005 | Yu | |
| 2006/0086622 A1 | 4/2006 | Prior | |
| 2006/0163085 A1 | 7/2006 | Hanaoka | |
| 2006/0169575 A1 | 8/2006 | Sumita | |
| 2006/0235350 A1 | 10/2006 | Alimi et al. | |
| 2006/0241002 A1 | 10/2006 | Rogozinski | |
| 2006/0241546 A1 | 10/2006 | Alimi | |
| 2006/0253060 A1 | 11/2006 | Alimi | |
| 2006/0263240 A1 | 11/2006 | Hopkins | |
| 2006/0275498 A1 | 12/2006 | Bagley | |
| 2007/0118096 A1 | 5/2007 | Smith et al. | |
| 2007/0134127 A1 | 6/2007 | Smith et al. | |
| 2007/0148256 A1 | 6/2007 | Yanagihara et al. | |
| 2007/0173755 A1 | 7/2007 | Alimi et al. | |
| 2007/0196357 A1 | 8/2007 | Alimi et al. | |
| 2007/0196434 A1 | 8/2007 | Alimi et al. | |
| 2007/0231247 A1 | 10/2007 | Bromberg et al. | |
| 2007/0265586 A1 | 11/2007 | Joshi et al. | |
| 2008/0125494 A1 | 5/2008 | Yu | |
| 2008/0160612 A1 | 7/2008 | Selkon | |
| 2008/0193423 A1 | 8/2008 | Brunton et al. | |
| 2008/0215019 A1 | 9/2008 | Malamutmann | |

(56) References Cited

U.S. PATENT DOCUMENTS

| | | |
|---|---|---|
| 2008/0255498 A1 | 10/2008 | Houle |
| 2008/0279963 A1 | 11/2008 | Najafi et al. |
| 2009/0068255 A1 | 3/2009 | Yu et al. |
| 2012/0164235 A1 | 6/2012 | Northey et al. |
| 2012/0251631 A1 | 10/2012 | Alimi et al. |
| 2012/0269904 A1 | 10/2012 | Northey et al. |
| 2014/0328946 A1 | 11/2014 | Northey |
| 2015/0306137 A1 | 10/2015 | Alimi et al. |
| 2016/0045547 A1* | 2/2016 | Alimi .............. A01N 59/00 424/665 |
| 2016/0120183 A1 | 5/2016 | Northey |

FOREIGN PATENT DOCUMENTS

| | | |
|---|---|---|
| CN | 1 938 053 A | 3/2007 |
| CN | 101163491 A | 4/2008 |
| CN | 101189017 A | 5/2008 |
| DE | 30 46 324 A1 | 12/1982 |
| DE | 10 2004 056456 A1 | 5/2006 |
| EP | 0 368 812 A1 | 5/1990 |
| EP | 0 601 891 A1 | 6/1994 |
| EP | 0 636 581 A1 | 7/1994 |
| EP | 0 740 329 A1 | 10/1996 |
| EP | 0 826 636 A1 | 3/1998 |
| EP | 0 841 305 A2 | 5/1998 |
| EP | 0 889 007 A1 | 1/1999 |
| EP | 0 949 205 A1 | 10/1999 |
| EP | 1 038 993 A1 | 9/2000 |
| EP | 1 064 845 A1 | 1/2001 |
| EP | 1 065 265 A1 | 1/2001 |
| EP | 1 074 515 A2 | 2/2001 |
| EP | 1 103 264 A2 | 5/2001 |
| EP | 1 162 176 A1 | 12/2001 |
| EP | 1 162 179 A1 | 12/2001 |
| EP | 1 293 481 A2 | 3/2003 |
| EP | 1 314 699 A1 | 5/2003 |
| EP | 1 386 887 A1 | 2/2004 |
| EP | 2 130 542 A1 | 12/2009 |
| GB | 1 422 795 A | 1/1976 |
| GB | 2253860 A | 9/1992 |
| GB | 2352728 A | 2/2001 |
| GB | WO 0113926 A2 * | 3/2001 .............. A61K 33/00 |
| JP | 01-194993 A | 8/1989 |
| JP | 01-218682 A | 8/1989 |
| JP | 02-111708 A | 4/1990 |
| JP | 02-149395 A | 6/1990 |
| JP | 05-228474 A | 9/1993 |
| JP | 05-228475 A | 9/1993 |
| JP | 05-339769 A | 12/1993 |
| JP | 06-182345 A | 7/1994 |
| JP | 06-254567 A | 9/1994 |
| JP | 06-312183 A | 11/1994 |
| JP | 06-335685 A | 12/1994 |
| JP | 07-000966 A | 1/1995 |
| JP | 07-010762 A | 1/1995 |
| JP | 07-031981 A | 2/1995 |
| JP | 07-075784 A | 3/1995 |
| JP | 07-155760 A | 6/1995 |
| JP | 07-214063 A | 8/1995 |
| JP | 07-323289 A | 12/1995 |
| JP | 07-328640 A | 12/1995 |
| JP | 08-001160 A | 1/1996 |
| JP | 08-052476 A | 2/1996 |
| JP | 08-061788 A | 3/1996 |
| JP | 08-164192 A | 6/1996 |
| JP | 08-326124 A | 12/1996 |
| JP | 09-025236 A | 1/1997 |
| JP | 09-157173 A | 6/1997 |
| JP | 09-290269 A | 11/1997 |
| JP | 10-080686 A | 3/1998 |
| JP | 10-113664 A | 5/1998 |
| JP | 10-128331 A | 5/1998 |
| JP | 10-192860 A | 7/1998 |
| JP | 11-151493 A | 6/1999 |
| JP | 2000-084559 A | 3/2000 |
| JP | 2000-189972 A | 7/2000 |
| JP | 2001-079548 A | 3/2001 |
| JP | 2001-096275 A | 4/2001 |
| JP | 2001-113276 A | 4/2001 |
| JP | 2001-191076 A | 7/2001 |
| JP | 2001-259640 A | 9/2001 |
| JP | 2001-286868 A | 10/2001 |
| JP | 03-236315 B2 | 12/2001 |
| JP | 03-247134 B2 | 1/2002 |
| JP | 2002-059164 A | 2/2002 |
| JP | 2002-145787 A | 5/2002 |
| JP | 2002165868 A * | 6/2002 |
| JP | 03-299250 B2 | 7/2002 |
| JP | 03-338435 B2 | 10/2002 |
| JP | 2002-363017 A | 12/2002 |
| JP | 03-396853 B2 | 4/2003 |
| JP | 2003-236543 A | 8/2003 |
| JP | 03-458341 B2 | 10/2003 |
| JP | 2004-049946 A | 2/2004 |
| JP | 2004-121607 A | 4/2004 |
| JP | 2004-173628 A | 6/2004 |
| JP | 2004-216349 A | 8/2004 |
| JP | 2004-223306 A | 8/2004 |
| JP | 2004-223309 A | 8/2004 |
| JP | 2004-223310 A | 8/2004 |
| JP | 2004-232413 A | 8/2004 |
| JP | WO 2004080901 A1 * | 9/2004 ............. C02F 1/4618 |
| JP | 2005-013520 A | 1/2005 |
| JP | 2005-058848 A | 3/2005 |
| JP | 2005-507395 A | 3/2005 |
| JP | 2007-512356 A | 5/2007 |
| JP | 2007-522222 A | 8/2007 |
| JP | 2007-523137 A | 8/2007 |
| JP | 2008-530022 A | 8/2008 |
| RO | 117 540 B1 | 4/2002 |
| SU | 1296156 A1 | 3/1987 |
| WO | WO 95/01137 A1 | 1/1995 |
| WO | WO 96/02271 A1 | 2/1996 |
| WO | WO 96/14835 A1 | 5/1996 |
| WO | WO 96/16555 A1 | 6/1996 |
| WO | WO 97/40814 A1 | 11/1997 |
| WO | WO 97/46489 A1 | 12/1997 |
| WO | WO 97/49638 A | 12/1997 |
| WO | WO 98/03713 A1 | 1/1998 |
| WO | WO 98/17588 A1 | 4/1998 |
| WO | WO 98/27013 A1 | 6/1998 |
| WO | WO 98/42625 A1 | 10/1998 |
| WO | WO 98/58880 A1 | 12/1998 |
| WO | WO 99/00588 A2 | 1/1999 |
| WO | WO 99/28238 A1 | 6/1999 |
| WO | WO 00/33757 A1 | 6/2000 |
| WO | WO 00/76475 A1 | 12/2000 |
| WO | WO 01/54704 A1 | 8/2001 |
| WO | WO 01/56616 A2 | 8/2001 |
| WO | WO 02/04032 A2 | 1/2002 |
| WO | WO 03/000957 A1 | 1/2003 |
| WO | WO 03/024491 A2 | 3/2003 |
| WO | WO 03/042111 A2 | 5/2003 |
| WO | WO 03/048421 A1 | 6/2003 |
| WO | WO 03/076688 A2 | 9/2003 |
| WO | WO 03/103522 A1 | 12/2003 |
| WO | WO 2004/076721 A2 | 9/2004 |
| WO | WO 2004/078654 A2 | 9/2004 |
| WO | WO 2004/079051 A1 | 9/2004 |
| WO | WO 2004/081222 A2 | 9/2004 |
| WO | WO 2004/081515 A2 | 9/2004 |
| WO | WO 2004/082690 A1 | 9/2004 |
| WO | WO 2004/092571 A1 | 10/2004 |
| WO | WO 2005/003848 A1 | 1/2005 |
| WO | WO 2005/009336 A2 | 2/2005 |
| WO | WO 2005/011417 A2 | 2/2005 |
| WO | WO 2005/020896 A2 | 3/2005 |
| WO | WO 2005/030651 A1 | 4/2005 |
| WO | WO 2005/051342 A1 | 6/2005 |
| WO | WO 2005/061394 A1 | 7/2005 |
| WO | WO 2005/065383 A2 | 7/2005 |
| WO | WO 2005/075581 A1 | 8/2005 |
| WO | WO 2005/077056 A2 | 8/2005 |

(56) References Cited

FOREIGN PATENT DOCUMENTS

| | | |
|---|---|---|
| WO | WO 2005/079745 A2 | 9/2005 |
| WO | WO 2005/080639 A1 | 9/2005 |
| WO | WO 2005/082176 A1 | 9/2005 |
| WO | WO 2005/117914 A2 | 12/2005 |
| WO | WO 2006/014578 A2 | 2/2006 |
| WO | WO 2006/084251 A2 | 8/2006 |
| WO | WO 2006/102680 A2 | 9/2006 |
| WO | WO 2006/102681 A2 | 9/2006 |
| WO | WO 2006/119300 A2 | 11/2006 |
| WO | WO 2007/031765 A1 | 3/2007 |
| WO | WO 2007/085018 A2 | 7/2007 |
| WO | WO 2008/043067 A2 | 4/2008 |
| WO | WO 2008/089268 A2 | 7/2008 |
| WO | WO 2008/112940 A1 | 9/2008 |
| WO | WO 2014/190184 A1 | 11/2014 |

OTHER PUBLICATIONS

"Buffer Solution," Wikipedia, http://en.wikipedia.org/wiki/Buffer_solution, retrieved Jul. 4, 2012.
"Hypersensitivity reaction—Type I," myvmc.com/diseases/hypersensitivity-reaction-type-i/ (4 pages) Oct. 7, 2005.
"New Remedies of 1917," *American Journal of Pharmacy*, vol. 90, p. 254 (1918).
"Sodium Hypochlorite," *Iryoyaku Nihon Iuakuhin Shu*, 2004 Edition, p. 886.
"Treatments for Cystic Fibrosis," Cystic Fibrosis Foundation, http://cystic-fibrosis.emedtv.com/cystic-fibrosis/treatment-for-cystic-fibrosis.html, retrieved Jun. 28, 2012.
*Aichi Prefectural Journal of Hospital Pharmacy*, vol. 27, No. 2, pp. 3-7 (1999).
Anderson et al., "Intracellular Bacterial Biofilm-Like Pods in Urinary Tract Infections," *Science*, vol. 301, pp. 105-107 (2003).
Arrigo et al., "Cytotoxic effects induced by oxidative stress in culture mammalian cells and protection provided by Hsp27 expression," *Methods* 35: 126-138 (2005).
Ash et al., "Handbook of Cosmetic and Personal Care Additives," Grower Publishing Limited, Hampshire, England, 1994. See, title, contents, pp. 602, 760.
Ayliffe, "Working Party Report: Decontamination of minimally invasive surgical endoscopes and accessories," *Journal of Hospital Infection*, 45: 263-277 (2000).
Badalament et al., "The Sensitivity of Bladder Wash Flow Cytometry, Bladder Wash Cytology, and Voided Cytology in the Detection of Bladder Carcinoma," *Cancer*, vol. 60, pp. 1423-1427 (1987).
Badia et al., "Saline Wound Irrigation Reduces the Postoperative Infection Rate in Guinea Pigs," *Journal of Surgical Research*, 63: 457-459 (1996).
Baoren et al., "Treatment with and toxicity of acidic electrolyzed oxidizing water in mice with peritonitis," *Medical Journal of the Chinese People's Armed Police Forces*, vol. 15, No. 3, pp. 167-169 (2004).
Bari et al., "Chemical and irradiation treatments for killing *Escherichia coli* O157:H7 on alfalfa, radish, and mung bean seeds," *J Food Prot.*, 66(5): 767-774 (2003).
Bari et al., "Effectiveness of electrolyzed acidic water in killing *Escherichia coli* O157:H7, *Salmonella enteritidis*, and *Listeria monocytogenes* on the surfaces of tomatoes," *J Food Prot.*, 66(4): 542-548 (2003).
Beckman et al., "The free radical theory of aging matures," *Physiol. Rev.* 78: 547-581 (1998).
Bibashi et al., "Fungal peritonitis Complicating peritoneal dialysis during an 11-year period: report of 46 cases," *Clinical Infectious Diseases*, 36: 927-931 (2003).
Boulton, "The Diabetic Foot," in *Diabetes: Clinical Management*, Chapter 26, 293-306 (1990).
Brook, "Bacteriology of Acute and Chronic Ethmoid Sinusitis," *Journal of Clinical Microbiology*, vol. 43, No. 7, pp. 3479-3480 (2005).

Bunyan, "The treatment of burns by hypochlorite solution," *Journal of Tropical Pediatrics*, vol. 29, No. 2, pp. 93-94 (1983).
Carlson, "Redox media as a factor in destroying germs," Schriftenreihe des Vereins fuer Wasser-, Boden- und Lufthygiene, 31: 21-39 (1970).
Carton et al., "Hypotonicity induces membrane protrusions and actin remodeling via activation of small GTPases Rac and Cdc42 in Rat-1 fibroblast," *Am. J. Physiol. Cell. Physiol.*, 285: C935-C944 (2003).
Chernomorskii, "Diagram of the electrochemical stability of water", Russian Journal of Physical Chemistry, 51(4), pp. 542-544 (1977) translation of article published in Zhurnal Fizicheskoi Khimii, 51: 924-925 (1977).
Chisholm, "Wound Evaluation and Cleansing," Soft Tissue Emergencies, 10(4), 665-672 (1992).
Cui et al., "Physicochemical properties and bactericidal efficiency of neutral and acidic electrolyzed water under different storage conditions," Journal of Food Engineering, No. 91, pp. 582-586 (2009).
De Beer et al., "Direct Measurement of Chlorine Penetration into Biofilms during Disinfection," *Applied and Environmental Microbiology*, vol. 60, No. 12, pp. 4339-4344 (1994).
De Grey, "Reactive oxygen species production in the mitochondrial matrix: implications for the mechanism of mitochondrial mutation accumulation," *Rejuvenation Res.*, 8(1): 13-17 (2005).
De Lloyd, "Parts Per Millions Conversions," *Delloyd's Lab Tech Resources Reagents and Solutions*, http://delloyd.50megs.com/ppm.html (2000), downloaded Feb. 13, 2013.
Delves, "Overview of Allergic Reactions," *Merck Manual—Consumer Version* http://www.merckmanuals.com/home/immune-disorder/allergic-reactions-and-other-hypersensitivity-disorders/overview-of-allergic-reactions, downloaded Oct. 18, 2016 (13 pgs.) (http://www.merck.com/mmhe/print/sec16/ch185/ch185a.html).
Dimri et al., "A biomarker that identifies senescent human cell in culture and in aging skin in vivo," *Proc. Natl. Acad. Sci. USA*, 92(20): 9363-9667 (1995).
Dire et al., "A Comparison of Wound Irrigation Solutions Used in the Emergency Department," *Ann Emerg Med.*, 19(6): 704-708 (1998).
Douglass et al., "1. Diagnosis, treatment and prevention of allergic disease: the basics," *MJA Practice Essentials—Allergy*, vol. 185, No. 4, pp. 228-233 (2006).
Dressler et al., "Controls, Standards, and Histogram Interpretation in DNA Flow Cytometry," *Methods in Cell Biology*, 41, Chpt 17, pp. 241-262 (1994).
Dyson et al., "Comparison of the Effects of Moist and Dry Conditions on Dermal Repair," *Journal for Investigative Dermatology*, 91(5): 434-439 (1988).
Erwin-Toth et al., "Wound Care Selecting the Right Dressing," *Am J Nurs.*, 95(2): 46-51 (1995).
Eventov et al., "Detoxication and Disinfection with Sodium Hypochlorite," *Biomedical Engineering*, vol. 32, No. 6 (1998).
Fabrizio et al., "Comparison of electrolyzed oxidizing water with various antimicrobial interventions to reduce Salmonella species on poultry," Poultry Science, 81(10), pp. 1598-1605 (2002).
Field et al., "Overview of Wound Healing in a Moist Environment," Am J Surg., 167(1A): 2S-6S (1994).
Flint et al., "Virus cultivation, detection and genetics," in *Principles of Virology, Molecular Biology, Pathogenesis and Control*, Chapter 2, 25-56 (ASM Press 2000).
Fomin et al., "Participation of water [hydroxyl ions] in oxidation-reduction processes," *Sostoyanie Rol Vody Biol. Ob'ektakh, Simp., Tiflis*, 120-131 (1967) (Abstract only).
Fraga et al., "Ascorbic acid protects against endogenous oxidative DNA damage in human sperm," *Proc. Natl. Acad. Sci USA*, 88(24): 11003-11006 (1991).
Fraise, "Choosing disinfectants," *J Hosp infect*, 43: 255-264 (1999).
Frantz, "In Vivo We Trust," *Nature Reviews Drug Discovery*, No. 2, p. 501 (2003).
Free Dictionary.com, "Normal Saline" definition, retrieved from http://medical-dictionary.thefreedictionary.com/normal+saline on May 4, 2011.

(56) References Cited

OTHER PUBLICATIONS

Frippiat et al., "Subcytotoxic H2O2 stress triggers a release of transforming growth factor-beta, which induces biomarkers of cellular senescence of human diploie fibroblast," J. Biol. Chem. 276, 2531-2537 (2001).
Fukuzaki et al., "Effects of Dissociation State of Hypochlorous Acid on Cleaning and Disinfecting Actions," FY2007 Annual Report Industrial Technology Center of Okayama Prefecture, No. 34, Industrial Technology Center of Okayama Prefecture, 2007.
Gao et al., "Observation on the effect of disinfection to HBsAg by electrolyzed oxidizing water," Chinese Journal of Epidemiology, 22(1), pp. 40-42 (2001).
Goberdham et al., "A biomarker that identifies senescent human cell in culture and in aging skin in vivo," Proc. Natl. Acad. Sci. USA, 92: 9663-9667 (1995).
Guitierrez et al., "Produccion de agents biologicos par alas terapias genicas y celulares en humanos," Diagnostico molecular en medicina, 265-291 (2003).
Harada, "Behavior of hydrogen peroxide in electrolyzed anode water," Biosci. Biotechnol Biochem., 66(9): 1783-1791 (2002).
Hatto et al., "The physiological property and function of the electrolyzed-ionized calcium Aquamax on water molecular clusters fractionization," Artif. Organs, 21(1): 43-49 (1997). (Abstract only).
Hayashi et al., "Successful treatment of mediastinitis after cardiovascular surgery using electrolyzed strong acid water aqueous solution," Artif Organs, 21: 39-42 (1997).
Higgins et al., "Wound dressings and Topical Agents," The Diabetic Foot, 12(1): 31-40, (1995).
Hinman et al., "Effect of Air Exposure and Occlusion on Experimental Human Skin Wounds," Nature, 200, No. 4904, 377-379 (1963).
Hollander et al., "Laceration Management," Annals of Emergency Medicine, 34(3): 356-367 (1999).
Holmes et al., "Interactions of Candida albicanswith bacteria and salivary molecules in oral biofilms," Journal of Industrial Microbiology, vol. 15, pp. 208-213 (1995).
Horiba et al., "Bactericidal effect of electrolyzed neutral water on bacteria isolated from infected root canals," Oral Surg Oral Med Oral Pathol Oral Radiol Endod, 87(1): 83-87 (1999).
Horita et al., "Healing of Fournier's gangrene of the scrotum in a haemodialysis patient after conservative therapy alone," Nephrology Dialysis Transplantation, 15(3): 419-421 (2000).
Hybrid Turkeys, "Effective Chlorination" Info Sheet (3 pgs.) no date.
Inoue et al., "Trial of electrolyzed strong acid aqueous solution lavage in the treatment of peritonitis and intraperitoneal abscess," Artif Organs, 21(1): 28-31 (1997).
Ivanova et al., "Mechanism of the extracellular antioxidant defend," Experimental Pathology and Parasitology, 4: 49-59 (2000).
Iwasawa et al., "Bactericidal effect of acidic electrolyzed water—comparison of chemical acidic sodium hydrochloride (NaOCl) solution," Kansenshogaku Zasshi—Journal of Japanese Association on Infectious Diseases, 70(9): 915-922 (1996)—Abstract only.
Iwasawa et al., "The influence of pH on bactericidal effects of strong acidic electrolyzed water," Bokin Bobai, 30(10): 635-643, (2002).
Jeter et al., "Wound Dressings of the Nineties: Indications and Contraindications," Wound Healing, 8(4): 799-816 (1991).
Jiang et al., "5-Chlorouracil, A Marker of DNA Damage from Hypochlorous Acid during Inflammation," Journal of Biological Chemistry, vol. 278, No. 35, pp. 32834-32840 (2003).
Jones-Carson et al., "Susceptibility of Immunodeficeint Gene-Knockout Mice to Urinary Tract Infection," Journal of Urology, vol. 161, pp. 338-341 (1999).
Kanofsky et al., "Singlet Oxygen Production by Chloroperoxidase-Hydrogen Peroxide-Halide Systems," Journal of Biological Chemistry, vol. 259, No. 9, pp. 5596-5600 (1984).
Kanofsky et al., "Singlet Oxygen Production from the Reactions of Ozone with Biological Molecules," Journal of Biological Chemistry, vol. 266, No. 4, pp. 9039-9042 (1991).
Kaufman et al., "Preventing Diabetic Foot Ulcers," Derm. Nurs., 6(5): 313-320 (1994).
Kim et al., "Efficacy of electrolyzed oxidizing water in inactivating Salmonella on alfalfa seeds and sprouts," J Food Prot., 66(2): 208-214 (2003).
Kim et al., "Roles of oxidation-reduction potential in electrolyzed oxidizing and chemically modified water for the inactivation of food-related pathogens," J Food Prot, 63: 19-24 (2000).
Kimbrough et al., "Electrochemical removal of bromide and reduction of THM formation potential in drinking water," Water Res., 36(19): 4902-4906 (2002).
Kitamoto et al., "Use of hyperacidity water in hemodialysis facilities," Journal of Osaka Society for Dialysis Treatment, vol. 15, No. 2, pp. 183-186 (1997).
Kitaoka, K., "On the electrolytic separation factor of tritium," Radioisotopes, 30(5): 247-252 (1981)—Abstract only.
Kiura et al., "Bactericidal activity of electrolyzed acid water from solution containing sodium chloride at low concentration, in comparison with that at high concentration," J Microbiol Methods, 49(3): 285-93 (2002).
Koseki et al., "Decontamination of lettuce using acidic electrolyzed water," J Food Prot., 64(5): 652-658 (2001).
Koseki et al., "Decontaminative effect of frozen acidic electrolyzed water on lettuce," J Food Prot., 65(2): 411-414 (2002).
Koseki et al., "Effect of mild heat pre-treatment with alkaline electrolyzed water on the efficacy of acidic electrolyzed water against Escherichia coli O157:H7 and Salmonella on lettuce," Food Microbiology, 21(5): 559-566 (2004).
Koseki et al., "Effect of nitrogen gas packaging on the quality and microbial growth of fresh-cut vegetables under low temperatures," J Food Prot., 65(2): 326-332 (2002).
Koseki et al., "Prediction of microbial growth in fresh-cut vegetables treated with acidic electrolyzed water during storage under various temperature conditions," J Food Prot., 64(12): 1935-1942 (2001).
Kubota et al., "Effectiveness of acidic oxidative potential water in peritoneal lavage for perforated appendicitis," Asian Journal of Surgery, Department of Surgery, University of Hong Kong, Hong Kong., 22(3), 282-284 (Jul. 1999).
Laing, P., "Diabetic Foot Ulcers," Am J Surg, 167: 31S-36S (1994).
Landa-Solis et al., "Microcyn TM: a novel super-oxidized water with neutral pH and disinfectant activity," Journal of Hospital Infection, No. 61, pp. 291-299 (2005).
Len et al., "Effects of storage conditions and pH on chlorine loss in electrolyzed oxidizing (EO) water," J Agric Food Chem, 50: 209-212 (2002).
Len et al., "Ultraviolet spectrophotometric characterization and bactericidal properties of electrolyzed oxidizing water as influenced by amperage and pH," J Food Prot, 63: 1534-1537 (2000).
Li et al., "Preliminary study of microbiocide effect and its mechanism of electrolyzed oxidizing water," Chinese Journal of Epidemiology, 17(2): 95-98 (1996).
Loshon et al., "Analysis of the killing of spores of Bacillus subtilis by a new disinfectant, Sterilox," Journal of Applied Microbiology, 91: 1051-1058 (2001).
Madden et al., "Application of Principles of Fluid Dynamics to Surgical Wound Irrigation," Current Topics in Surgical Research, 3: 85-93 (1971).
Mak et al., "Reactive Oxidant Species in Asthma," Curr Opin Pulm Med, vol. 12, pp. 7-11 (2006).
Mangram et al., "Guideline for prevention of surgical site infection," Infection Control and Hospital Epidemiology, 20 (4): 247-278 (1999).
Marnett, L.J., "Oxyradicals and DNA damage," Carcinogenesis, 21(3), 361-370 (2000).
Martinez, F., "Sterilant for Human Wounds is Changing Patients' Lives" Infection Control Today, 3 pgs. (Nov. 2004), downloaded from http://www.infectioncontroltoday.com/articles/2004/11/sterilant-for-human-wounds-is-changing-patients-l.aspx.
MedlinePlus: AIDS [online] retrieved from http://www.nlm.nih.gov/medlineplus/ency/article/000594.htm on Jan. 16, 2010. May 30, 2009, pp. 1-6.

(56) References Cited

OTHER PUBLICATIONS

MedlinePlus: Asthma [online] retrieved from http://www.nlm.nih.gov/medlineplus/ency/article/000141.htm on Jan. 16, 2010. May 21, 2009, pp. 1-5.

MedlinePlus: Multiple Sclerosis [online] retrieved from http://www.nlm.nih.gov/medlineplus/ency/article/000737.htm on Jun. 11, 2009. Jan. 21, 2009, pp. 1-5.

MedlinePlus: Myocarditis [online] retrieved from http://www.nlm.nih.gov/medlineplus/ency/article/000149.htm on Jan. 16, 2010. May 15, 2008, pp. 1-4.

Michida et al., "Biomimetic oxidation of diphenyl sulfide with electrochemical P-450 model system in CH2Cl2 treated with alkaline solution," *Yakugaku Zasshi—Journal of the Pharmaceutical Society of Japan*, 119(10): 780-785 (1999).

Middleton et al., "Comparison of a solution of super-oxidized water (Sterilox) with glutaraldehyde for the disinfection of bronchoscopes, contaminated in vitro with *Mycobacterium tuberculosis* and *Mycobacterium avium-intracellulare* in sputum," *Journal of Hospital Infection*, 45: 278-282 (2000).

Miranda-Altamirano et al., "Treatment of 2nd and 3rd Degree Burns in 48 Pediatric Patients Without Routine Antibiotics Routine Using New Super-oxidized Water Technology" Abstract for Meeting of the Texas Surgical Society, San Antonio, TX, Apr. 1-3, 2005 (2 pgs).

Miyamoto et al., "Effectiveness of acidic oxidative potential water in preventing bacterial infection in islet transplantation," *Cell Transplantation*, 8: 405-411 (1999).

Model, et al., "Effectiveness of electrolyzed oxidized water irrigation in a burn-wound infection," *J Trauma Injury, Infection, and Critical Care*, 49: 511-514 (2000).

Morita et al., "Disinfection potential of electrolyzed solution containing sodium chloride at low concentrations," *J Virol Methods*, 85: 163-174 (2000).

Morris et al., "Biofilm: Why the Sudden Interest," *Journal of Otolaryngology*, vol. 34, Suppl. 2, pp. S56-S59 (2005).

Moscati et al., "Comparison of Normal Saline with Tap Water for Wound Irrigation," *American Journal of Emergency Medicine*, 16(4): 379-385 (1998).

Moyer et al., "Modulation of human fibroblast Gap junction intercellular communication by Hyaluronan," *J. Cell. Biol.* 196: 165-170 (2003).

Naderi et al., "Oxidative stress-induced apoptosis in dividing fibroblast involves activation of p38 MAP kinase and over expression of Bax: Resistance of quiescent cells to oxidative stress," *Apoptosis*, 8(1): 91-100 (2003).

Nagamatsu et al., "Application of electrolyzed acid water to sterilization of denture base part 1. Examination of sterilization effects on resin plate," *Dent. Mater J*, 20(2): 148-55, (2001)—Abstract only.

Nagamatsu et al., "Durability of bactericidal activity in electrolyzed neutral water by storage," *Dental Materials Journal*, 21(2): 93-104 (2002).

Nakae et al., "Effectiveness of electrolyzed oxidized water irrigation in a burn-wound infection model," *J Trauma*, 49(3): 511-514 (2000).

Nakae et al., "Electronlyzed Strong Acidic Water in a Burn Injury Model, on Usefulness of Hydrocolloid Dressing for Wound Healing," *Japanese Journal of Burn Injuries*, vol. 26, No. 2, p. 7 (2000).

Nakagawa et al., "Effect of rinsing hydrocolloid impressions using acidic electrolyzed water on surface roughness and surface hardness of stone models," *J Oral Sci.*, 44(3-4): 141-146 (2002)—Abstract only.

Nakagawara et al., "Spectroscopic characterization and the pH dependence of bactericidal activity of the aqueous chlorine solution," *Analytical Sciences*, 14(4): 691-698 (1998).

Nathan, "Points of control in inflammation," *Nature*, vol. 420, pp. 846-852 (2002).

Nelson, D., "Newer technologies for endoscope disinfection: electrolyzed acid water and disposable-component endoscope systems," *Gasatrointestinal Endoscopy Clinics of North America*, (Kerry Holland, Ed.) WB Saunders Co., Philadelphia, PA, vol. 10, No. 2, pp. 319-328 (2000).

Nomasa et al., "Sterilization of Dental Instruments by Electrolyzed Water and Their Corrosion Behaviors," *Journal of Kyushu Dental Society*, vol. 51, No. 6, pp. 784-799 (1997).

Ogino et al., "Treatment for abdominal aortic graft infection: irrigation with electrolyzed strong aqueous acid, in-situ grafting, and omentoplasty," *Thorac Cardiovasc Surg*, 48(1): 43-44 (2000).

Ohno et al., "Mediastinal Irrigation with Superoxidized Water After Open-Heart Surgery: The Safety and Pitfalls of Cardiovascular Surgical Application," *Surgery Today*, 30: 1055-1056 (2000).

Okubo et al., "Cytotoxicity and microbicidal activity of electrolyzed strong acid water and acidic hypochlorite solution under isotonic conditions," *Kansenshogaku Zasshi: Journal of the Japanese Association for Infectious Diseases*, 73(10): 1025-1031 (1999)—Abstract only.

O'Neill, "Physiological significance of volume-regulatory transporters," *Am. J. Physiol.*, 276: C995-C1001 (1999).

Oomori et al., "The efficiency of disinfection of acidic electrolyzed water in the presence of organic materials," *Analytical Science*, 16: 365-369 (2000).

Otteneder et al., "Correlation of DNA adduct levels with tumor incidence: carcinogenic potency of DNA adducts," *Mutat. Res.*, 424: 237-247 (1999).

Park et al., "Antimicrobial effect of electrolyzed water for inactivating Campylobacter jejuni during poultry washing," International Journal of Food Microbiology, 72(1-2): 77-83 (2002).

Park et al., "Effectiveness of electrolyzed water as a sanitizer for treating different surfaces," *J Food Prot.*, 65(8): 1276-1280 (2002).

Park et al., "Effects of chlorine and pH on efficacy of electrolyzed water for inactivating *Escherichia coli* O157:H7 and *Listeria monocytogenes*," *International Journal of Food Microbiology*, 91(1): 13-18 (2004).

Perezous et al., "Colonization of *Candida* species in denture wearers with emphasis on HIV infection: A literature review," *Journal of Prosthetic Dentistry*, vol. 93, No. 3, pp. 288-293 (2005).

Piaggesi et al., "Sodium carboxyl-methyl-cellulose dressings in the management of deep ulcerations of diabetic foot," *Diabet Med.*, 18(4): 320-324 (2001).

Plontke et al., "Transtympanic Endoscopy for Drug Delivery to the Inner Ear Using a New Microendoscope," *Adv. Otorhinolaryngol.*, vol. 59, pp. 149-155 (2002).

Powis et al., "Redox signaling and the control of cell growth and death," *Pharmacol Ther.*, 68(1): 149-173 (1995).

Prutz, "Reactions of hypochlorous acid with biological substrates are activated catalytically by tertiary amines," *Archives of Biochemistry and Biophysics*, vol. 357, No. 2, pp. 265-273 (1998).

Rodeheaver et al., "Identification of the Wound Infection-Potentiating Factors in Soil," *American Journal of Surgery*, 128(1): 8-14, (1974).

Ruddy et al., "Decontamination in Practice: Endoscopic decontamination: an audit and practical review," *Journal of Hospital Infection*, 50: 261-268 (2002).

Russell, S.M., "The effect of electrolyzed oxidative water applied using electrostatic spraying on pathogenic and indicator bacteria on the surface of eggs," *Poult. Sci.*, 82(1): 158-162 (2003).

Rutala et al., "New Disinfection and Sterilization Methods," *Emerging Infectious Diseases*, 7(2): 348-353 (2001).

Rutala et al., "Stability and bactericidal activity of chlorine solutions," *Infection Control and Hospital Epidemiology: The Official Journal of the Society of Hospital Epidemiologists of America*, vol. 19, No. 5, pp. 323-327 (1998).

Sakai, S., "Development of ionic electrolyzed water and its utilities. The preparation of ionic electrolyzed water and its application to disinfection," *Kurin Tekunoroji*, 6(3): 53-57 (1996)—Abstract only.

Sakashita et al., "Antimicrobial effects and efficacy on habitually hand-washing of strong acidic electrolyzed water—a comparative study of alcoholic antiseptics and soap and tap water", *Kansenshogaku Zasshi: The Journal of the Japanese Association on Infectious Diseases*, 76: 373-377 (2002).

Sanders, L., "Diabetes Mellitus: Prevention of Amputation," *J Am Pod Med Assoc*, 84(7): 322-328 (1994).

(56) References Cited

OTHER PUBLICATIONS

Sawada et al., "Complete electrolysis using a microflow cell with an oil/water interface," *Anal Chem.*, 74(5): 1177-1181 (2002).
Schaap et al., "Singlet Molecule Oxygen and Superoxide Dismutase," *JACS*, vol. 96, No. 12, pp. 4025-4026 (1974).
Sekiya et al., "The Use of Function Water for Treating Infected Skin Ulcers: Clinical Results," *Japanese Journal of Plastic Surgery*, vol. 38, No. 10, pp. 1051-1057 (1995).
Sekiya et al., "Treatment of Infectious Skin Defects or Ulcers with Electrolyzed Strong Acid Aqueous Solution," *Artificial Organs*, 21(1): 32-38 (1997).
Selkon et al., "Evaluation of the antimicrobial activity of a new super-oxidized water, Sterilox®, for the disinfection of endoscopes," *Journal of Hospital Infection*, 41: 59-70 (1999).
Sena et al., "In Vitro antimicrobial activity of sodium hypochlorite and chlorhexidine against selected single-species biofilms," *International Endodontic Journal*, vol. 39, pp. 878-885 (2006).
Severino et al., "Is ?-galactosidase staining a marker of senescence in vitro and in vivo?" *Exp. Cell. Res.*, 257(1): 162-171 (2000).
Sharma et al., "Treatment of *Escherichia coli* O157:H7 inoculated alfalfa seeds and sprouts with electrolyzed oxidizing water," *International Journal of Food Microbiology*, 86(3): 231-237 (2003).
Shen et al., "Interactions of selenium compounds with other antioxidants in DNA damage and apoptosis in Human normal keratinocytes," *Cancer Epidemiology, Biomarkers, & Prevention*, 10(4): 385-390 (2001).
Shetty et al., "Evaluation of microbicidal activity of a new disinfectant: Sterilox® 2500 against Clostridium difficile spores, Helicobacter pylori, cancomycin resistant *Enterococcus* species, Candida albicans and several *Mycobacterium* species," Journal of Hospital Infection, 41: 101-105 (1999).
Shimada et al., "A comparison of the bactericidal effects and cytotoxic activity of three types of oxidizing water, prepared by electrolysis, as chemical dental plaque control agents," *International Journal of Antimicrobial Agents*, vol. 15, No. 1, pp. 4-53 (2000).
Shimmura et al., "Acidic Electrolyzed Water in the Disinfection of the Ocular Surface," *Experimental Eye Research*, 70(1): 1-6 (2000).
Shirahata et al., "Electrolyzed-reduced water scavenges active oxygen species and protects DNA from oxidative damage," *Biochem. Biophys. Res. Commun.*, 234(1): 269-274 (1997).
Singer et al., "Evaluation and Management of Traumatic Lacerations," *New England Journal of Medicine*, vol. 337., No. 16, pp. 1142-1148 (1997).
SMARTe.org, "Understanding Units of Measurement," http://www.smarte.org/smarte/dynamic/resource/sn-units-of-measure.xml.pdf (2008).
Smirnov et al., "Electron exchangers and electron- and ion-exchangers and their use in a water treatment system," *Khim. Aktiv. Polim. Ikh Primen*, 259-262 (1969)—Abstract only.
Solovyeva et al., "Cleaning effectiveness of root canal irrigation with electrochemically activated anolyte and catholyte solutions: a pilot study," *International Endodontic Journal*, 33: 494-504 (2000).
Soto et al., "Bacterial sulfate production by biodesulfurization of aromatic hydrocarbons, determined by ion chromatography," *J Chromatogr A*, 824(1): 45-52 (1998).
Soucek et al., "Clinical and histopathological aspects of ear disease in the acquired immunodeficiency syndrome," *Progress in Human Auditory and Vestibular Histopathology*, Kugler Publications, pp. 117-123 (1997).
Stein, G., "SV-40-transformed human fibroblasts: evidence for cellular aging in pre-crises cells," *J Cell Physiol*, 125: 36-44 (1985).
Stevenson et al., "Cleansing the Traumatic Wound by High Pressure Syringe Irrigation," *JACEP*, 5(1): 17-21 (1976).
Subrahmanyam, "Topical Application of Honey in Treatment of Burns," *British Journal of Surgery*, vol. 78, pp. 497-498 (1991).
Sumita et al., "Characteristics and use of acidified water from redox water generator," *Shokuhin Kogyo*, 40(10): 29-36 (1997)—Abstract only.
Suzuki et al., "Novel products generated from 2'-deoxyguanosine by hypochlorous acid or a myeloperoxidase-H2O2—Cl-system: identification of diimino-imidazole and amino-imidazolone nucleosides," *Nucleic Acids Res.*, 30(11): 2555-2564 (2002).
Takeshita et al., "Influence of free residual chlorine concentration and pH on bactericidal effects of electrolyzed water," *Bokin Bobai*, 29(2): 69-72 (2001).
Takeyoshi et al., "Primary eye irritation and 5-day cumulative skin irritation studies of super oxidized water in rabbits," *Oyo Yakuri*, 48(3): 173-177 (1994)—Abstract only.
Tanaka et al., "Antimicrobial activity of superoxidized water" *Journal of Hospital Infection*, 34: 43-49 (1996).
Tanaka et al., "Molecular basis of antiapoptotic effect of immunophilin ligands on hydrogen peroxide-induced apoptosis in human glioma cells," *Neurochem Res.*, 29(8): 1529-1536 (2004).
Tanaka et al., "The use of electrolyzed solutions for the cleaning and disinfecting of dialyzers" *Artif. Organs*, 24(12): 921-928 (2000).
Tateno et al., "MT-4 plaque formation can distinguish cytopathic subtypes of the human immunodeficiency virus (HIV)," *Virology*, 167: 299-301 (1988).
Theoharides et al., "Corticotropin-Releasing Hormone Induces Skin Mast Cell Degranulation and Increased Vascular Permeability, a Possible Explanation for Its Proinflammatory Effects," *Endorinology*, vol. 139, No. 1, pp. 403-413 (1998).
Thurnheer et al., "Mass Transport of Macromolecules within an In Vitro Model of Supragingival Plaque," *Applied and Environmental Microbiology*, vol. 69, No. 3, pp. 1702-1709 (2003).
Upright et al., "Evaluation of Mesalt dressings and continuous wet saline dressings in ulcerating metastatic skin lesions," *Cancer Nursing*, 17(2): 149-155 (1994).
Valko et al., "Role of oxygen radicals in DNA damage and cancer incidence," *Mol Cell Biochem*, 266: 37-56 (2004).
Van Britsom et al., "A rapid method for the detection of uranium in surface water," *Sci. Total Environ.*, vols. 173/174, pp. 83-89 (1995).
Venkitanarayanan et al., "Efficacy of Electrolyzed Oxidizing Water for Inactivating *Escherichia coli* O157:H7, *Salmonella enteritidis*, and *Listeria monocytogenes*," *Applied and Environmental Microbiology*, 65(9): 4276-4279 (1999).
Veves et al., "A randomized, controlled trial of Promogran (a collagen/oxidized regenerated cellulose dressing) vs standard treatment in the management of diabetic foot ulcers," *Arch Surg.*, 137(7): 822-827 (2002).
Winter, "Formation of the Scab and the Rate of Epithelization of Superficial Wounds in the Skin of the Young Domestic Pig," *Nature*, 193: 293-294 (1962).
Xakellis et al., "Hydrocolloid versus saline-gauze dressings in treating pressure ulcers: a cost-effectiveness analysis," *Arch Phys Med Rehabil.*, 73(5): 463-9 (1992).
Yahagi et al., "Effect of Electrolyzed Water on Wound Healing," *Artificial Organs*, 24 (12): 984-987 (2000).
Yang et al., "The effect of pH on inactivation of pathogenic bacteria on fresh-cut lettuce by dipping treatment with electrolyzed water," *Journal of Food Science*, 68(3): 1013-1017 (2003).
Yoshimoto et al., "Virucidal effect of super oxidized water" *Kagaku Ryoho no Ryoiki*, 12(7): 1337-1342 (1996)—Abstract only.
Young et al., "Mechanisms of killing of Bacillus subtilis spores by hypochlorite and chlorine dioxide," *J Appl Microbiol*, 95: 54-67 (2003).
Zambon et al., "Studies of the Subgingival Microflora in Patients with Acquired Immunodeficiency Syndrome," *Journal of Peridontology*, vol. 61, No. 11, pp. 699-704 (1990).
Zhang et al., "Antioxidant superoxide dismutase attenuates increased endothelial permeability induced by platelet activating factor," *Soc Gynecol Investig.* 10: 5-10 (2003).
Zinkevich et al., "The effect of super-oxidized water on *Escherichia coli*," *Journal of Hospital Infection*, 46: 153-156 (2000).
European Patent Office, International Search Report in International Application No. PCT/US2007/060854 (Sep. 4, 2007).
European Patent Office, Written Opinion in International Application No. PCT/US2007/060854 (Sep. 4, 2007).
International Bureau of WIPO, International Preliminary Report on Patentability in International Application No. PCT/US2007/060854 (Jul. 31, 2008).

(56) References Cited

OTHER PUBLICATIONS

U.S. Appl. No. 09/714,826, filed Nov. 17, 2000.
U.S. Appl. No. 10/146,140, filed May 16, 2002.
U.S. Appl. No. 10/496,092, filed May 19, 2004.
U.S. Appl. No. 10/380,902, filed Sep. 20, 2001.
U.S. Appl. No. 10/862,092, filed Jun. 4, 2004.
U.S. Appl. No. 10/242,779, filed Sep. 13, 2002.
U.S. Appl. No. 10/916,278, filed Aug. 11, 2004.
U.S. Appl. No. 10/916,566, filed Aug. 11, 2004.
U.S. Appl. No. 10/496,092, filed Dec. 5, 2002.
U.S. Appl. No. 11/388,912, filed Mar. 23, 2006.
U.S. Appl. No. 11/388,930, filed Mar. 23, 2006.
U.S. Appl. No. 11/416,091, filed May 2, 2006.
U.S. Appl. No. 11/502,821, filed Aug. 11, 2006.
U.S. Appl. No. 11/656,328, filed Jan. 22, 2007.
U.S. Appl. No. 11/656,088, filed Jan. 22, 2007.
U.S. Appl. No. 11/656,087, filed Jan. 22, 2007.
U.S. Appl. No. 11/725,279, filed Mar. 19, 2007.
U.S. Appl. No. 12/477,792, filed Jun. 3, 2009.
U.S. Appl. No. 12/531,276, filed Mar. 13, 2008.
U.S. Appl. No. 12/645,419, filed Dec. 22, 2009.
U.S. Appl. No. 12/643,191, filed Dec. 21, 2009.
U.S. Appl. No. 13/320,225, filed May 10, 2010.
U.S. Appl. No. 13/436,288, filed Mar. 30, 2012.
U.S. Appl. No. 13/378,659, filed Jun. 15, 2010.
U.S. Appl. No. 13/387,923, filed Jul. 30, 2010.
U.S. Appl. No. 14/893,448, filed May 22, 2014.
U.S. Appl. No. 14/336,575, filed Jul. 21, 2014.
U.S. Appl. No. 14/924,361, filed Oct. 27, 2015.
U.S. Appl. No. 15/346,446, filed Nov. 8, 2016.
U.S. Appl. No. 15/358,639, filed Nov. 22, 2016.

\* cited by examiner

METHODS OF TREATING OR PREVENTING INFLAMMATION AND HYPERSENSITIVITY WITH OXIDATIVE REDUCTIVE POTENTIAL WATER SOLUTION

CROSS-REFERENCE TO RELATED APPLICATIONS

This patent application is a continuation of U.S. patent application Ser. No. 12/643,191, filed Dec. 21, 2009, which is a continuation of U.S. patent application Ser. No. 11/656, 087, filed Jan. 22, 2007, which claims the benefit of U.S. Provisional Application Nos. 60/760,635, filed Jan. 20, 2006; 60/760,567, filed Jan. 20, 2006; 60/760,645, filed Jan. 20, 2006; and 60/760,557, filed Jan. 20, 2006; all of which are hereby incorporated by reference in their entireties.

BACKGROUND OF THE INVENTION

Inflammation is a biological response that can result from a noxious stimulus and is normally intended to remove that stimulus or ameliorate its effects. Although normally intended to promote survival, inflammation can cause damage to the host, especially in mammals. The stimulus or insult initiating inflammation can be caused by endogenous factors (e.g., an auto-antigen or irritating body fluid) or exogenous factors (e.g., a foreign body or infectious agent).

Inflammation has been classified as "acute" and "chronic." Acute inflammation is typically of relatively short duration, lasting minutes to hours and, in some cases, a few days. Acute inflammation can be characterized by the exudation of fluid and plasma proteins and the accumulation of polymorphonuclear leukocytes (PMNLs) at the site of the insult. Acute inflammation usually includes an increase in blood flow to the area of the insult mediated by cellular molecules released in response to the insult. Increased vascular permeability also results from cellular mediators and leads to an accumulation of protein-rich fluid. Important mediators of this increased blood flow and vascular permeability include histamine from mast cells, serotonin and bradykinin.

In acute inflammation, PMNLs are also attracted to the area of insult and migrate out of the blood stream toward the insult. The PMNLs release toxic metabolites and proteinases that can cause tissue damage. These proteinases include proteins in the complement system, which can damage cell membranes and kallikreins which generate bradykinin. Acute inflammation can undergo complete resolution, lead to the formation of an abscess, result in scarring fibrosis or progress to chronic inflammation.

Chronic inflammation is of longer duration, lasting weeks to months, and possibly years, in which tissue destruction and biological processes that are intended to repair the injury are simultaneously ongoing. Chronic inflammation more typically involves lymphocytes and macrophages and may also include a proliferation of blood vessels, fibrosis and/or necrosis. Chronic inflammation can result from a number of conditions including persistent infections, prolonged exposure to toxic agents, and autoimmune reactions. Chronic inflammation is often maintained by the production of cytokines by lymphocytes and macrophages at the site of the persistent insult. Chronic inflammation can result in permanent tissue damage or complete healing.

Hypersensitivity generally refers to inflammation that causes damage to the host, in which the damage outweighs the benefit to the host. Hypersensitivity can result in significant pathology including, e.g., anaphylaxis, transplant rejection, and autoimmune diseases. The most common type of hypersensititvity is allergy.

Independently of the inducing factor—and the length of the exposure—an inflammatory reaction is mediated by a varied number and type of cells and molecules, the later including cytokines, growth factors, clotting factors, enzymes, neurotransmitters and complement proteins, among others. These molecules are primarily secreted by fibroblasts, endothelial and infiltrating cells (e.g. macrophages, lymphocytes, mast cells, polymorphonuclear cells, etc), and local nerves in response to the insulting agent. The mixture and amount of cytokines therein released will depend on the type, concentration and exposure time of the inducing agent. Therefore, these proteins could mediate from an acute local inflammatory reaction to systemic life-threatening responses (e.g. acute systemic inflammatory response syndrome, SIRS; multiple organ failure as in septic shock; anaphylaxis, etc). In chronic inflammatory processes, the cytokines continuously recruit more and more infiltrating cells that generate, for example, granulomas, induration of the tissues, and encapsulated abscesses. In any case, proteins secreted during an inflammatory process are central players in the grade and persistence of the final reaction.

Stimulation of the aforementioned cells by the induction agent leads to a cascade of intracellular signaling events that ultimately result in production and secretion of cytokines and other inflammatory mediators that constitute the pro-inflammatory response. While the pro-inflammatory response is crucial for effective clearance of the pathogen or allergen, the inflammatory mediators produced cause tissue damage and inflammation. Hence, a balance needs to be maintained between the activation and down-regulation of this response in order to avoid severe tissue damage (Cohen, J.: The immunopathogenesis of sepsis. *Nature* 2002 420, 885-891). Dysregulation of this response could induce local damage (e.g. lung fibrosis) or could lead to potentially lethal conditions like septic shock and systemic inflammatory response syndrome (SIRS) as previously mentioned. Thus, microbes allergens, endotoxins, and many other molecules induce the production of pro-inflammatory mediator proteins by different cells in the human body. The combined effects of all these molecules in living tissues could mediate changes in the clotting system, wound healing process, anti-microbial activity, antibody production and the perception of pain, among many other reactions.

The systemic inflammatory response syndrome (SIRS), a syndrome that encompasses the features of systemic inflammation without end-organ damage or identifiable bacteremia. SIRS is separate and distinct from sepsis, severe sepsis or septic shock. The key transition from SIRS to sepsis is the presence of an identified pathogen in the blood. The pathophysiology of SIRS includes, but is not limited to, complement activation, cytokine and arachidonic acid metabolites secretion, stimulated cell-mediated immunity, activation of the clotting cascades, and humoral immune mechanisms. Clinically SIRS is characterized by tachycardia, tachypnea, hypotension, hypoperfusion, oliguria, leukocytosis or leukopenia, pyrexia or hypothermia, metabolic acidosis, and the need for volume support. SIRS may affect all organ systems and may lead to multiple organ dysfunction syndrome (MODS). Thus, even in early stages (i.e. SIRS), there is accumulation of pro-inflammatory cytokines at the primary site of inflammation and in the blood that can contribute to the establishment of multi-organ failure and death.

Typically, inflammation is treated with steroidal or non-steroidal anti-inflammatory drugs. However, conventional anti-inflammatory therapy suffers from several drawbacks, e.g., systemic toxicity, allergic reactions, insulin resistance, hypertension, cardiac toxicity, renal toxicity, various coagulopathies and gastric erosions. Accordingly, there is a need for mild, yet safe and effective methods for treating or preventing inflammation. The present invention provides such methods. These and other advantages of the invention, as well as additional inventive features, will be apparent from the description of the invention provided herein.

BRIEF SUMMARY OF THE INVENTION

The present invention provides a method of preventing or treating inflammation in a patient by administering to the patient a therapeutically effective amount of an oxidative reductive potential (ORP) water solution, wherein the solution is stable for at least twenty-four hours. The method of the present invention can be used in the treatment of inflammation resulting from a variety of causative factors, e.g., allergic reaction, autoimmune reaction, infection, contact with one or more inflammation-causing substances, and combinations of such causative factors.

The method of the present invention can further include administering the ORP water solution in conjunction with one or more therapeutic agents, e.g., one or more compounds selected from the group consisting of antibiotics, anti-viral agents, anti-inflammatory agents, and combinations thereof. Administering such therapeutic agents in conjunction with the ORP water solution includes administering one or more of such agents, e.g., prior to, during (e.g., contemporaneously, by co-administration or in combination with), or following administration of the ORP water solution.

The ORP water solution can be administered by any suitable route in accordance with the present invention, e.g., by delivering the ORP water solution topically or parenterally, so as to contact a therapeutically effective amount of the ORP water solution with one or more affected tissues, which may reside inside or outside of the body. Accordingly, the invention provides a method wherein the ORP water solution is administered to one or more tissues, e.g., nasal, sinus, pharyngeal, tracheal, pulmonary, esophageal, gastric, intestinal, mesothelial, peritoneal, synovial, urinary bladder, uretheral, vaginal, uterine, fallopian, pancreatic, nervous, oral, cutaneous, and subcutaneous. The ORP water solution can be administered in any suitable form in accordance with the present invention, e.g., as a liquid, spray, mist, aerosol or steam, and, if desired, can be combined with one or more suitable carriers, e.g., vehicles, adjuvants, excipients, diluents, and the like.

The ORP water solution administered in accordance with the present invention can be contained within a sealed container and is stable for at least twenty-four hours. The ORP water solution administered in accordance with the invention can be produced by electrolysis, and preferably comprises a mixture of anode water and cathode water, which contains one or more species, including, e.g., reactive species, ionic species, radical species, precursors thereof and combinations thereof. The ORP water solution administered in accordance with the invention exhibits potent anti-inflammatory activity, yet is virtually free of toxicity to normal tissues and normal eukaryotic cells.

DETAILED DESCRIPTION OF THE INVENTION

Figure 1:
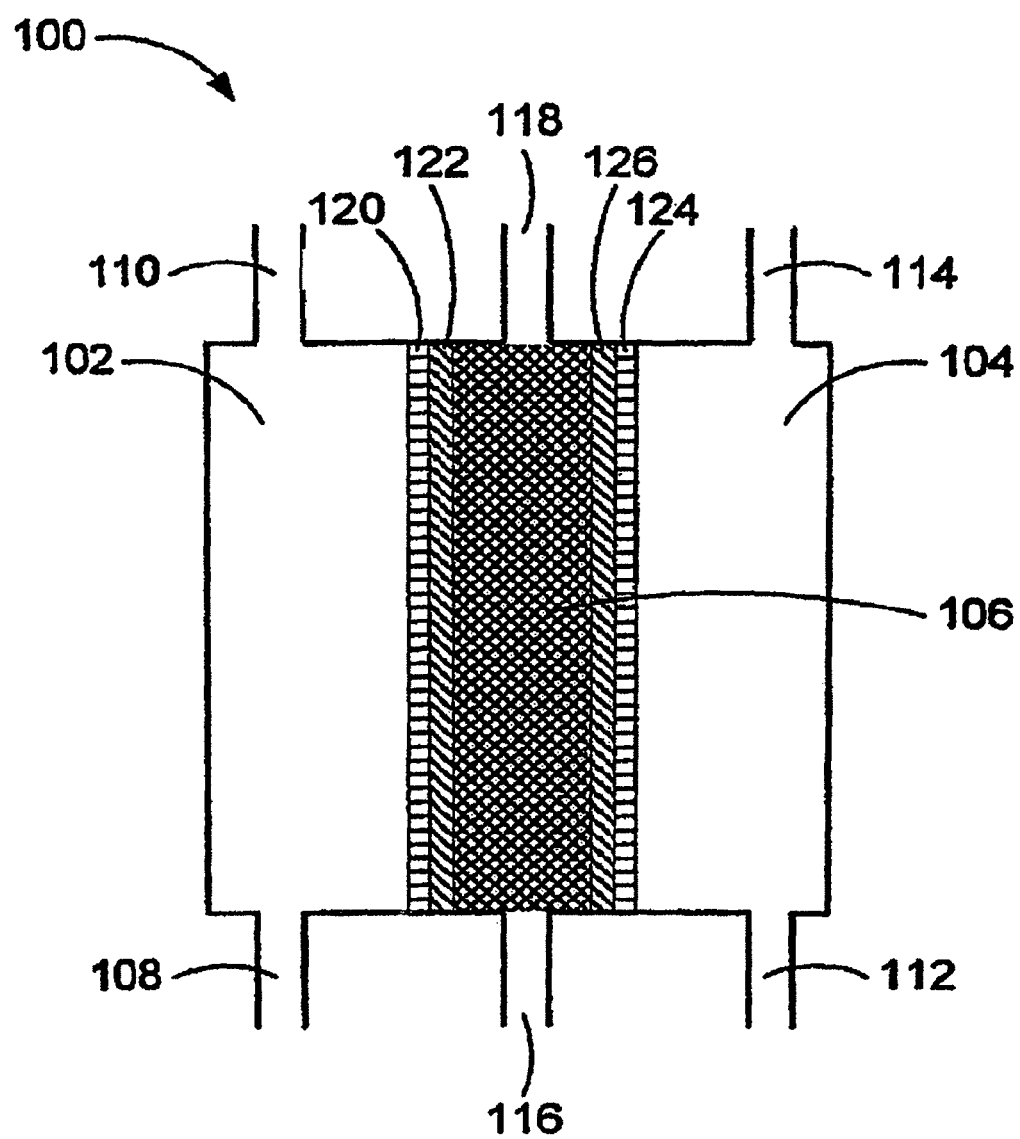
FIG. 1 illustrates a three-chambered electrolysis cell for producing an exemplary ORP water solution.

The present invention provides a method of preventing or treating inflammation in a patient, which method comprises administering to the patient a therapeutically effective amount of an oxidative reductive potential (ORP) water solution (also known as super-oxidized water (SOW)), wherein the solution is stable for at least about twenty-four hours. The method of the present invention can be used for treating or preventing (e.g., inhibiting the onset of, inhibiting the escalation of, decreasing the likelihood of) acute inflammation and chronic inflammation, including hypersensitivity such as, e.g., in allergies. The inflammation and hypersensitivity treatable or preventable in accordance with the method of the present invention can include inflammation that results from, e.g., contact with a noxious stimulus, injury, infection, autoimmune reaction, hypersensitivity, and allergic reaction, including allergic reactions associated with cellular histamine and pro-inflammatory cytokine release.

Surprisingly, it has been found that the ORP water solution administered in accordance with the invention is a highly effective inhibitor of mast cell degranulation, one of the primary inflammation and allergy-causing biological cascades. The ORP water solution administered in accordance with the invention inhibits degranulation of mast cells regardless of whether they are activated with an antigen or a calcium ionophore. Also surprisingly, it has been found that the ORP water solution administered in accordance with the present invention non-selectively inhibits the secretion of pro-inflammatory cytokines in mast cells. For example, the ORP water solution of the present invention can inhibit the secretion of, e.g., TNF-$\alpha$, MIP1-$\alpha$, IL-6, and IL-13 in mast cells. It is believed that the ORP water solution administered in accordance with the invention also can inhibit the secretion of pro-inflammatory cytokines in other cytokine-secreting cells including, but not limited to, macrophages, monocytes, lymphocytes, macrophages, PMN, fibroblasts and endothelial cells. These findings demonstrate that the ORP water administered in accordance with the present invention should exhibit broad anti-inflammatory efficacy.

The ORP water solution administered in accordance with the invention preferably inhibits mast cell degranulation by more than about 50% relative to untreated mast cells, more preferably by more than about 80% relative to untreated mast cells, still more preferably by more than about 90% relative to untreated mast cells, and even more preferably by more than about 95% relative to untreated mast cells, when contacted with the ORP water solution for up to about 30 minutes, more preferably up to about 15 minutes, and still more preferably up to about 5 minutes.

The ORP water solution administered in accordance with the invention also preferably inhibits the secretion of TNF-$\alpha$ by more than about 50%, more preferably by more than about 60%, still more preferably by more than about 70%, and even more preferably by more than about 85%. In addition, the ORP water solution administered in accordance with the invention also preferably inhibits the secretion of MIP1-$\alpha$ by more than 25%, more preferably by more than about 50%, and still more preferably by more than about 60%. Further, the ORP water solution administered in accordance with the invention also preferably inhibits the secretion of IL-6 and/or IL-13 by more than 25%, more preferably by more than about 50%, and still more preferably by more than about 60%. In accordance with the method of the invention, secretion of these and that of other cytokines, can be therapeutically inhibited down to certain % by the administration of the ORP water solution alone or in combination with a diluent (e.g., water), by increasing the concentration of the components of the ORP water solution, by utilizing special delivery systems and/or by increasing the exposure time. For instance, cytokine secretion can be therapeutically inhibited by administering compositions in which the ORP water solution is diluted, e.g., by a ratio of up to about 50% (vol./vol.) ORP water solution/diluent, by a ratio of up to about 25% (vol./vol.) ORP water solution/diluent, by a ratio of up to about 10% (vol./vol.) ORP water solution/diluent, by a ratio of up to about 5% (vol./vol.) ORP water solution/diluent, or even by a ratio of up to about 1% (vol./vol.) ORP water solution/diluent.

The method of the present invention can be used for treating or preventing cell-mediated inflammation, which results from an autoimmune reaction, including, but not limited to, SLE, autoimmune thyroiditis, sarcoidosis, inflammatory bowel disease, rheumatoid arthritis, rheumatic fever, psoriasis, pemphigus, erythema multiforme, other bullous diseases of the skin, and atopias. The method of the invention can be used for treating or preventing inflammation, which results from infection, allergens, foreign bodies, and autoimmune processes. The method of the invention can also be used for treating or preventing inflammation, which results from infection, e.g., from an infection by one or more microorganisms selected from the group consisting of viruses, bacteria, and fungi, including hypersensitivity and autoimmune-mediated inflammation resulting from infection.

The method of the present invention can be used for treating or preventing inflammation associated with an upper respiratory condition. When the inflammation is associated with an upper respiratory condition, the ORP water solution is preferably administered to the upper airway, e.g., as a spray, mist, aerosol or steam, so as to contact one or more upper airway tissues affected by the condition. Any suitable method can be employed for delivering the ORP water solution to the upper airway so as to treat or prevent one or more upper respiratory conditions in accordance with the present invention, including one or more routes of administration described herein.

The method of the present invention can be used for preventing or treating inflammation affecting one or more upper respiratory airway tissues (e.g., nasal tissue, sinus tissue) or lung tissues. Such conditions can include, for example, sinusitis (e.g., rhinosinusitis, acute sinusitis, chronic sinusitis, and the like), pharyngitis, asthma, and the like, which are preventable or treatable with the ORP solution administered in accordance with the invention.

Chronic sinusitis typically refers to inflammation of the sinuses that continues for at least 3 weeks, but the inflammation can (and often does) continue for months or even years. Allergies are frequently associated with chronic sinusitis. In addition, patients with asthma have a particularly high frequency of chronic sinusitis Inhalation of airborne allergens (substances that provoke an allergic reaction), such as dust, mold, and pollen, often set off allergic reactions (e.g., allergic rhinitis) that, in turn, may contribute to sinusitis (particularly rhinosinusitis or rhinitis). People who are allergic to fungi can develop a condition called "allergic fungal sinusitis." Damp weather or pollutants in the air and in buildings also can affect people subject to chronic sinusitis.

Like acute sinusitis, chronic sinusitis is more common in patients with immune deficiency or abnormalities of mucus secretion or movement (e.g., immune deficiency, HIV infection, cystic fibrosis, Kartagener's syndrome). In addition, some patients have severe asthma, nasal polyps, and severe asthmatic responses to aspirin and aspirin-like medications (so-called non-steroidal anti-inflammatory drugs, or NSAIDs). These latter patients have a high frequency of chronic sinusitis.

A doctor can diagnose sinusitis by medical history, physical examination, X-rays, and if necessary, MRIs or CT scans (magnetic resonance imaging and computed tomography). After diagnosing sinusitis and identifying a possible cause, a doctor can prescribe a course of treatment that will reduce the inflammation and relieve the symptoms. Treating acute sinusitis typically requires re-establishing drainage of the nasal passages, controlling or eliminating the source of the inflammation, and relieving the pain. Doctors generally recommend decongestants to reduce the congestion, antibiotics to control a bacterial infection, if present, and pain relievers to reduce the pain.

When treatment with drugs fails, surgery may be the only alternative for treating chronic sinusitis, e.g., removal of adenoids, removal of nasal polyps, repair of a deviated septum, endoscopic sinus surgery, and the like. It is believed that the administration of ORP water in accordance with the method of the present invention can be used for treating chronic sinusitis and inflammation associated therewith as an alternative to potentially avoid more aggressive therapies, such as antibiotics and surgery.

With regard to pharyngitis, it is estimated that worldwide, 1 to 2% of all visits to doctors' offices, clinics and emergency rooms are because of pharyngitis. In the United States and Mexico, pharyngitis and tonsillitis is believed to account for about 15 and 12 million consultations per year, respectively. These cases are typically caused by various bacteria and viruses. Also, pharyngitis and tonsillitis caused by group A β-hemolytic *Streptococcus* can significantly raise the risk of rheumatic fever in poor populations; however it is believed that only 5 to 15% of pharyngitis cases are caused by this bacterium, and that the rest of the acute cases are due to bacteria and viruses of little epidemiological relevance. The latter cases tend to be self-limiting in a few days and do not leave sequelae.

It has been verified that a great number of doctors worldwide prescribe antibiotics indiscriminately for acute pharyngitis. This occurs in a daily practice, often because patients tend to request powerful antibiotics. Unfortunately, it is difficult to establish an accurate diagnosis of streptococcal pharyngitis/tonsillitis clinically and the cost/benefit ratio of treating acute pharyngitis/tonsillitis with antibiotics is questionable.

It is believed that the method of the present invention provides a safe, efficacious and cost-effective adjuvant therapy for the treatment or prevention of acute pharyngitis and/or tonsillitis due to bacteria and/or viruses. The empirical treatment of acute pharyngitis/tonsillitis may begin with administering an ORP water solution in accordance with the present invention, and, depending on evolution or the result of the rapid test for *Streptococcus*, antibiotics may be initiated from 48-72 hours thereafter only if needed. The method of the present invention may thus allow the use of antibiotics to be deferred and, at the same time, reduce the symptomatology of the patient and accelerate the patient's recovery if the pharyngitis/tonsillitis is not from group A *Streptococcus*. The adjuvant use of an ORP water solution of the present invention with antibiotics for the treatment of streptococcal pharyngitis/tonsillitis also may shorten the period of clinical response and decrease the incidence of recurrences.

The method of the present invention also can be used for treating or preventing inflammation associated with hypersensitivity. Historically, hypersensitivity reactions have been classified as one of four types, from which significant disease can result. The ORP water solution administered in accordance with the invention can be used to treat and/or prevent (e.g., inhibit the onset of, inhibit the escalation of or decrease the likelihood of) one or more of such reactions. Type I hypersensitivity typically results from the combination of an antigen with an antibody bound to a mast cell or basophil. Type I reactions occur within minutes of exposure to the antigen in individuals who have been previously sensitized to the antigen. In humans, Type I reactions are mediated by IgE which has high affinity Fc receptors on mast cells and basophils.

Mast cells' role in Type I hypersensitivity is especially important because they reside in tissues under the epithelial surface near blood vessels and nerves. Multiple clinical symptoms observed in atopic dermatitis, allergic rhinitis and atopic asthma are produced by IgE-antigen stimulation of mast cells located in distinct affected tissues. The currently accepted view of the pathogenesis of atopic asthma is that allergens initiate the process by triggering IgE-bearing pulmonary mast cells (MCs) to release mediators such as histamine, leukotrienes, prostaglandins, kininis, platelet activating factor (PAF), etc. in the so-called early phase of the reaction (see Kumar et al., Robbins & Cotran Pathologic Basis of Disease, 2004, pp. 193-268, which is hereby incorporated by reference). In turn, these mediators induce bronchoconstriction and enhance vascular permeability and mucus production. According to this model, following mast cell activation in the late phase, those cells secrete various cytokines, including tumor necrosis factor alpha (TNF-α), IL-4, IL-5 and IL-6, which participate in the local recruitment and activation of other inflammatory cells such as eosinophils, basophils, T lymphocytes, platelets and mononuclear phagocytes. These recruited cells, in turn, contribute to the development of an inflammatory response that may then become autonomous and aggravate the asthmatic symptoms. This late phase response constitutes a long term inflammatory process which will induce changes in surrounding tissues (Kumar et al., pp. 193-268). Clinically, Type I reactions can have local effects such as allergic rhinitis, or systemic effects as is found in anaphylaxis which manifests with itching, hives, respiratory distress, and circulatory collapse.

Type II hypersensitivity is mediated by antibodies directed to antigens on the surfaces of cells and in the extracellular space. These antibodies can direct cell lysis or result in opsonization of the target molecules (preparation for phagocytosis by other cells). Alternatively, the antibodies can be directed to and activate cell surface receptors. Conditions resulting from Type II reactions include transfusion reactions, Graves disease (thyrotoxicosis), drug reactions, pernicious anemia, and acute rheumatic fever. In rheumatic fever the antibodies are formed against Streptococcal antigens but, cross-react with human tissues such as heart valves.

Type III hypersensitivity is caused by immune complexes, which are combinations of antibodies and other host immune system proteins, most typically complement proteins. It is the normal function of antibodies to bind and active complement. However, when the resulting macromolecular immune complexes are not adequately processed, they can lead to persistent tissue damage. Macrophages and PMNLs can be activated by immune complexes and lead to the release of toxic chemicals by these cells. Immune complex reactions can be local and may result in conditions such as, e.g., the arthus reaction or cause systemic disease such as serum sickness or some of the aspects of systemic lupus erythematous (SLE).

Type IV hypersensitivity is cell mediated and is sometimes called delayed-type hypersensitivity. Type IV hypersensitivity is mediated by T lymphocytes and often results in the formation of a granulomatous reaction. In a granulomatous reaction, a form of macrophage called an epitheloid cells attempts to, but fails, to digest an antigen. The antigen's persistence leads to the release of cytokines that attract additional lymphocytes resulting in chronic foci of inflammation. The foci have high concentrations of cyotoxic T-lymphocytes which release granzymes and perforins which are toxic to adjacent cells. Type IV hypersensitivity is a prominent component of autoimmune diseases such as, e.g., Sjogrren's Syndrome, Sarcoidosis, and contact dermatitis.

Pathologic states can combine different types of hypersensitivity reactions. In autoimmune diseases host antigens stimulate hypersensitivity with serious consequences for the host. For example, in SLE host antigens induce Type II reactions against blood cells while Type III reactions lead to blood vessel and renal glomerular damage. In addition, hypersensitivity reactions are also seen in iatragenic conditions such as drug reactions and transplant rejection. Transplant rejection includes components of Type II and Type IV hypersensivity. Accordingly, ORP water solution in accordance with the invention in transplantable organs or cells could greatly reduced the possibility of being rejected by the host.

It has been found that the ORP water solution administered in accordance with the invention is virtually free of toxicity to normal tissues and normal mammalian cells. The ORP water solution administered in accordance with the invention causes no significant decrease in the viability of eukaryotic cells, no significant increase in apoptosis, no significant acceleration of cell aging and/or no significant oxidative DNA damage in mammalian cells. The non-toxicity is particularly advantageous, and perhaps even surprising, given that the disinfecting power of the ORP water solution administered in accordance with the invention is roughly equivalent to that of hydrogen peroxide, yet is significantly less toxic than hydrogen peroxide is to normal tissues and normal mammalian cells. These findings demonstrate that the ORP water solution administered in accordance with the present invention is safe for use, e.g., in mammals, including humans.

For the ORP water solution administered in accordance with the invention, the cell viability rate is preferably at least about 65%, more preferably at least about 70%, and still more preferably at least about 75% after an about 30 minute exposure to the ORP water solution. In addition, the ORP water solution administered in accordance with the invention preferably causes only up to about 10% of cells, more preferably only up to about 5% of cells, and still more preferably only up to about 3% of cells to expose Annexin-V on their cellular surfaces when contacted with the ORP water solution for up to about thirty minutes or less (e.g., after about thirty minutes or after about five minutes of contact with the ORP water solution).

Further, the ORP water solution administered in accordance with the invention preferably causes less than about 15% of cells, more preferably less than about 10% of cells, and still more preferably less than about 5% of cells to express the SA-β-galactosidase enzyme after chronic exposure to the OPR water solution. The ORP water solution administered in accordance with the invention preferably causes caused the same fraction of the oxidative DNA adduct formation caused by saline solution, e.g., less than about 20% of the oxidative DNA adduct formation, less than about 10% of the oxidative DNA adduct formation, or about 5% or less of the oxidative DNA adduct formation normally caused by hydrogen peroxide in cells treated under equivalent conditions.

The ORP water solution administered in accordance with the invention produces no significant RNA degradation. Accordingly, RNA extracted from human cell cultures after an about 30 minutes exposure to the ORP water solution or r at about 3 hours after an about 30 minute-exposure, and analyzed by denaturing gel electrophoresis, will typically show no significant RNA degradation and will typically exhibit two discreet bands corresponding to the ribosomal eukaryotic RNAs (i.e. 28S and 18S) indicating that the ORP water solution administered in accordance with the invention leaves the RNA substantially intact. Similarly, RNA extracted from human cell cultures after about 30 minutes of exposure to the ORP water solution or after about 3 hours of exposure, can be subjected reverse transcription and amplification (RT-PCR) of the constitutive human GAPDH (Glyceraldehyde-3-phosphate dehydrogenase) gene and result in a strong GAPDH band on gel electrophoresis of the RT-PCR products. By contrast, cells treated with HP for a similar period show significant RNA degradation and little if any GAPDH RT-PCR product.

The ORP water solution used in accordance with the present invention can be administered using any suitable method of administration known in the art. For instance, the ORP water solution can be administered parenterally, endoscopically or directly to the surface of any affected biological tissue, e.g., to the skin and/or one or more mucosal surfaces. Parenteral administration can include using, for example, administering the ORP water solution intramuscularly, subcutaneously, intravenously, intra-arterially, intrathecally, intravesically or into a synovial space. Endoscopic administration of the ORP water solution can include using, e.g., bronchoscopy, colonoscopy, sigmoidoscopy, hysterscopy, laproscopy, athroscopy, gastroscopy or a transurethral approach. Administering the ORP water solution to a mucosal surface can include, e.g., administration to a nasal, oral, tracheal, bronchial, esophageal, gastric, intestinal, peritoneal, urethral, vesicular, urethral, vaginal, uterine, fallopian, and synovial mucosal surface.

Parenteral administration also can include administering the ORP water solution used in accordance with the invention intravenously, subcutaneously, intramuscularly, or intraperitoneally. The ORP water solution of the present invention can be administered intravenously as described, e.g., in U.S. Pat. Nos. 5,334,383 and 5,622,848 (hereby incorporated by reference), which describe methods of treating viral myocarditis, multiple sclerosis, and AIDS via intravenous administration of ORP water solutions. Other applications include the treatment of any hypersensitivity and infectious processes, as mentioned above.

The ORP water solution used in accordance with the invention can be administered topically, e.g., as a liquid, spray, mist, aerosol or steam by any suitable process, e.g., by aerosolization, nebulization or atomization. The ORP solution of the present invention can be administered to the upper airway as a steam or a spray. When the ORP water solution is administered by aerosolization, nebulization or atomization, it is preferably administered in the form of droplets having a diameter in the range of from about 0.1 micron to about 100 microns, preferably from about 1 micron to about 10 microns. In one embodiment, the method of the present invention includes administering the ORP water solution in the form of droplets having a diameter in the range of from about 1 micron to about 10 microns to one or more mucosal tissues, e.g., one or more upper respiratory tissues and/or lung tissues.

Methods and devices, which are useful for aerosolization, nebulization and atomization, are well known in the art. Medical nebulizers, for example, have been used to deliver a metered dose of a physiologically active liquid into an inspiration gas stream for inhalation by a recipient. See, e.g., U.S. Pat. No. 6,598,602 (hereby incorporated by reference). Medical nebulizers can operate to generate liquid droplets, which form an aerosol with the inspiration gas. In other circumstances medical nebulizers may be used to inject water droplets into an inspiration gas stream to provide gas with a suitable moisture content to a recipient, which is particularly useful where the inspiration gas stream is provided by a mechanical breathing aid such as a respirator, ventilator or anaesthetic delivery system.

An exemplary nebulizer is described, for example, in WO 95/01137, which describes a hand held device that operates to eject droplets of a medical liquid into a passing air stream (inspiration gas stream), which is generated by a recipient's inhalation through a mouthpiece. Another example can be found in U.S. Pat. No. 5,388,571 (hereby incorporated by reference), which describes a positive-pressure ventilator system which provides control and augmentation of breathing for a patient with respiratory insufficiency and which includes a nebulizer for delivering particles of liquid medication into the airways and alveoli of the lungs of a patient. U.S. Pat. No. 5,312,281 (hereby incorporated by reference) describes an ultrasonic wave nebulizer, which atomizes water or liquid at low temperature and reportedly can adjust the size of mist. In addition, U.S. Pat. No. 5,287,847 (hereby incorporated by reference) describes a pneumatic nebulizing apparatus with scalable flow rates and output volumes for delivering a medicinal aerosol to neonates, children and adults. Further, U.S. Pat. No. 5,063,922 (hereby incorporated by reference) describes an ultrasonic atomizer. The ORP water solution also may be dispensed in aerosol form as part of an inhaler system for treatment of infections in the lungs and/or air passages or for the healing of wounds in such parts of the body.

For larger scale applications, a suitable device may be used to disperse the ORP water solution into the air including, but not limited to, humidifiers, misters, foggers, vaporizers, atomizers, water sprays, and other spray devices. Such devices permit the dispensing of the ORP water solution on a continuous basis. An ejector which directly mixes air and water in a nozzle may be employed. The ORP water solution may be converted to steam, such as low pressure steam, and released into the air stream. Various types of humidifiers may be used such as ultrasonic humidifiers, stream humidifiers or vaporizers, and evaporative humidifiers. The particular device used to disperse the ORP water solution may be incorporated into a ventilation system to provide for widespread application of the ORP water solution throughout an entire house or healthcare facility (e.g., hospital, nursing home, etc.).

In accordance with the invention, the ORP water solution can be administered alone or in combination with one or more pharmaceutically acceptable carriers, e.g., vehicles, adjuvants, excipients, diluents, combinations thereof, and the like, which are preferably compatible with one or more of the species that exist in the ORP water solution. One skilled in the art can easily determine the appropriate formulation and method for administering the ORP water solution used in accordance with the present invention. Any necessary adjustments in dose can be readily made by a skilled practitioner to address the nature and/or severity of the condition being treated in view of one or more clinically relevant factors, such as, e.g., side effects, changes in the patient's overall condition, and the like.

For example, the ORP water solution can be formulated by combining or diluting the ORP water solution with up to about 25% (wt./wt. or vol./vol.) of a suitable carrier, up to about 50% (wt./wt. or vol./vol.) of a suitable carrier, up to about 75% (wt./wt. or vol./vol.) of a suitable carrier, up to about 90% (wt./wt. or vol./vol.) of a suitable carrier, up to about 95% (wt./wt. or vol./vol.) of a suitable carrier, or even with up to about 99% (wt./wt. or vol./vol.) or more of a suitable carrier. Suitable carriers can include, e.g., water (e.g., distilled water, sterile water, e.g., sterile water for injection, sterile saline and the like). Suitable carriers also can include one or more carriers described in U.S. patent application Ser. No. 10/916,278 (hereby incorporated by reference). Exemplary formulations can include, e.g., solutions in which the ORP water solution is diluted with sterile water or sterile saline, wherein the ORP water solution is diluted by up to about 25% (vol./vol.), by up to about 50% (vol./vol.), by up to about 75% (vol./vol.), by up to about 90% (vol./vol.), by up to about 95% (vol./vol.), or by up to 99% (vol./vol.) or more of a suitable carrier.

The ORP water solution administered in accordance with the invention can further be combined with (or be administered in conjunction with) one or more additional therapeutic agents, e.g., one or more active compounds selected from the group consisting of antibacterial agents (e.g., antibiotics), anti-viral agents, anti-inflammatory agents, and combinations thereof.

The therapeutically effective amount administered to the patient, e.g., a mammal, particularly a human, in the context of the present invention should be sufficient to affect a therapeutic or prophylactic response in the patient over a reasonable time frame. The dose can be readily determined using methods that are well known in the art. One skilled in the art will recognize that the specific dosage level for any particular patient will depend upon a variety of potentially therapeutically relevant factors. For example, the dose can be determined based on the strength of the particular ORP water solution employed, the severity of the condition, the body weight of the patient, the age of the patient, the physical and mental condition of the patient, general health, sex, diet, the frequency of applications, and the like. The size of the dose also can be determined based on the existence, nature, and extent of any adverse side effects that might accompany the administration of a particular ORP water solution. It is desirable, whenever possible, to keep adverse side effects to a minimum.

Factors, which can be taken into account for a specific dosage can include, for example, bioavailability, metabolic profile, time of administration, route of administration, rate of excretion, the pharmacodynamics associated with a particular ORP water solution in a particular patient, and the like. Other factors can include, e.g., the potency or effectiveness of the ORP water solution with respect to the particular condition to be treated, the severity of the symptoms presented prior to or during the course of therapy, and the like. In some instances, what constitutes a therapeutically effective amount also can be determined, in part, by the use of one or more of the assays, e.g., bioassays, which are reasonably clinically predictive of the efficacy of a particular ORP water solution for the treatment or prevention of a particular condition.

The ORP water solution used in accordance with the present invention can be administered, alone or in combination with one or more additional therapeutic agents, to a patient, e.g., a human, e.g., to treat an existing condition. The ORP water solution of the present invention also can be administered prophylactically, alone or in combination with one or more additional therapeutic agents, to a patient, e.g., a human, that has been exposed to one or more causative agents associated with the condition. For example, the ORP water solution can be suitably administered prophylactically to a patient that has been exposed to one or more inflammation-causing microorganisms (e.g., infections, viruses, bacteria and/or fungi)—or hypersensitivity epitope or allergen- to inhibit or decrease the likelihood of inflammation (and even infection) associated with the microorganism or epitope in a patient, or decrease the severity of an inflammation (and even infection or allergy) that develops as a result of such exposure.

One skilled in the art will appreciate that suitable methods of administering the ORP water solution used in accordance with the present invention are available, and, although more than one route of administration can be used, a particular route can provide a more immediate and more effective reaction than another route. The therapeutically effective amount can be the dose necessary to achieve an "effective level" of the ORP water solution in an individual patient, independent of the number of applications a day. The therapeutically effective amount can be defined, for example, as the amount required to be administered to an individual patient to achieve a blood level, tissue level, and/or intracellular level of the ORP water solution (or one or more active species contained therein) to prevent or treat the condition in the patient.

When the effective level is used as a preferred endpoint for dosing, the actual dose and schedule can vary depending, for example, upon interindividual differences in pharmacokinetics, distribution, metabolism, and the like. The effective level also can vary when the ORP water solution is used in combination with one or more additional therapeutic agents, e.g., one or more anti-infective agents, one or more "moderating," "modulating" or "neutralizing agents," e.g., as described in U.S. Pat. Nos. 5,334,383 and 5,622,848 (hereby incorporated by reference), one or more anti-inflammatory agents, and the like.

An appropriate indicator can be used for determining and/or monitoring the effective level. For example, the effective level can be determined by direct analysis (e.g., analytical chemistry) or by indirect analysis (e.g., with clinical chemistry indicators) of appropriate patient samples (e.g., blood and/or tissues). The effective level also can be determined, for example, by direct or indirect observations such as, e.g., the concentration of urinary metabolites, changes in markers associated with the condition (e.g., viral count in the case of a viral infection), histopathology and immunochemistry analysis, positive changes in image analysis (e.g. X ray, CT scan, NMR, PET, etc), nuclear medicine studies, decrease in the symptoms associated with the conditions, and the like.

Conventional ORP water solutions have an extremely limited shelf-life, usually only a few hours. As a result of this short lifespan, using conventional ORP water solutions requires the production to take place in close proximity to the point of use. From a practical standpoint, this means that the facility, e.g., a healthcare facility such as a hospital, must purchase, house and maintain the equipment necessary to produce conventional ORP water solution. Additionally, conventional manufacturing techniques have not been able to produce sufficient commercial-scale quantities to permit widespread use, e.g., as a general disinfecting agent for healthcare facilities.

Unlike conventional ORP water solutions, the ORP water solution administered in accordance with the invention is stable for at least about twenty-hours after its preparation. In addition, the ORP water solution administered in accordance with the invention is generally environmentally safe and, thus, avoids the need for costly disposal procedures. Preferably, the ORP water solution administered in accordance with the invention is stable for at least about one week (e.g., one week, two weeks, three weeks, four weeks or more.), and more preferably at least about two months. Still more preferably, the ORP water solution administered in accordance with the invention is stable for at least about six months. Even more preferably, the ORP water solution administered in accordance with the invention is stable for at least about one year, and most preferably is stable for more than about one year, e.g., at least about two years or at least about three years.

Stability can be measured based on the ability of the ORP water solution to remain suitable for one or more uses, for example, inhibiting mast cell degranulation, inhibiting cytokine secretion, decontamination, disinfection, sterilization, anti-microbial cleansing, and wound cleansing, for a specified period of time after its preparation under normal storage conditions (e.g., room temperature). The stability of the ORP water solution administered in accordance with the invention also can be measured by storage under accelerated conditions, e.g., from about 30° C. to about 60° C., in which the ORP water solution preferably is stable for up to about 90 days, and more preferably for up to about 180 days.

Stability also can be measured based on the concentration over time of one or more species (or precursors thereof) present in solution during the shelf-life of the ORP water solution. Preferably, the concentrations of one or more species, e.g., free chlorine, hypocholorous acid and one or more additional superoxidized water species and are maintained at about 70% or greater of their initial concentration for at least about two months after preparation of the ORP water solution. More preferably, the concentration of one of more of these species is maintained at about 80% or greater of their initial concentration for at least about two months after preparation of the ORP water solution. Still more preferably, the concentration of one or more of such species is maintained at about 90% or greater, and most preferably is maintained at about 95% or greater, of their initial concentration for at least about two months after preparation of the ORP water solution.

Stability also can be determined based on the reduction in the amount of organisms present in a sample following exposure to the ORP water solution. Measuring the reduction of organism concentration can be made on the basis of any suitable organism including, e.g., bacteria, fungi, yeasts, or viruses. Suitable organisms can include, e.g., *Escherichia coli, Staphylococcus aureus, Candida albicans*, and *Bacillus athrophaeus* (formerly *B. subtilis*).

The ORP water solution administered in accordance with the invention can function as a low-level disinfectant capable of a four log ($10^4$) reduction in the concentration of live microorganisms, and also can function as a high-level disinfectant capable of a six log ($10^6$) reduction in concentration of live microorganisms. Preferably, the ORP water solution administered in accordance with the invention is capable of yielding at least about a four log ($10^4$) reduction in total organism concentration, following exposure for one minute when measured at least about two months after preparation of the solution. More preferably, the ORP water solution is capable of a $10^4$-$10^6$ reduction of organism concentration when measured at least about six months after preparation of the solution. Still more preferably, the ORP water solution is capable of a $10^4$-$10^6$ reduction of organism concentration when measured at least about one year after preparation of the ORP water solution, and most preferably when measured more than about one year, e.g., at least about two years or at least about three years, after preparation of the ORP water solution.

For instance, the ORP water solution administered in accordance with the present invention can be capable of at least about a five log ($10^5$) reduction in the concentration of a sample of live microorganisms from the group consisting of *Pseudomonas aeruginosa, Escherichia coli, Enterococcus hirae, Acinetobacter baumannii, Acinetobacter* species, *Bacteroides fragilis, Enterobacter aerogenes, Enterococcus faecalis*, Vancomycin resistant-*Enterococcus faecium* (VRE, MDR), *Haemophilus influenzae, Klebsiella oxytoca, Klebsiella pneumoniae, Micrococcus luteus, Proteus mirabilis, Serratia marcescens, Staphylococcus aureus, Staphylococcus epidermidis, Staphylococcus haemolyticus, Staphylococcus hominis, Staphylococcus saprophyticus, Streptococcus pneumoniae, *Streptococcus pyogenes, Candida albicans* within thirty seconds of exposure, when measured at least two months after preparation of the ORP water solution (BioSciences Labs, Montana, US). Preferably, the ORP water solution is capable of achieving a $10^5$ reduction of all these organisms when measured at least about six months after preparation, and more preferably when measured at least about one year after preparation.

The invention also provides methods for killing bacteria in biofilms, e.g., *Pseudomonas aeruginosa* in biofilms. The invention further provides methods for killing of *Moraexlla catarrhalis* and antibiotic resistant bacteria, e.g., penicillin resistant *Streptococcus*. The methods disclosed herein can be used in accordance with the invention for killing bacteria using ORP water solutions faster than with using Bacitracin.

In one embodiment, the ORP water solution administered in accordance with the invention can reduce a sample of live microorganisms including, but not limited to, *Escherichia coli, Pseudomonas aeruginosa, Staphylococcus aureus* and *Candida albicans*, from an initial concentration of between about $1 \times 10^6$ and about $1 \times 10^8$ organisms/ml to a final concentration of about zero organisms/ml within about one minute of exposure when measured at least about two months after preparation of the ORP water solution. This corresponds to from about a six log ($10^6$) to about an eight log ($10^8$) reduction in organism concentration. Preferably, the ORP water solution is capable of achieving a $10^6$-$10^8$ reduction of *Escherichia coli, Pseudomonas aeruginosa, Staphylococcus aureus* or *Candida albicans* organisms when measured at least about six months after preparation, and more preferably when measured at least about one year after preparation.

Alternatively, the ORP water solution administered in accordance with the present invention can produce about a six log ($10^6$) reduction in the concentration of a spore suspension of *Bacillus athrophaeus* spores within about five minutes of exposure when measured at least about two months after preparation of the ORP water solution. Preferably, the ORP water solution administered in accordance with the invention can achieve about a $10^6$ reduction in the concentration of *Bacillus athrophaeus* spores when measured at least about six months after preparation, and more preferably when measured at least about one year after preparation.

The ORP water solution administered in accordance with the invention also can produce about a four log ($10^4$) reduction in the concentration of a spore suspension of *Bacillus athrophaeus* spores within about thirty (30) seconds of exposure when measured at least about two months after preparation of the ORP water solution. Preferably, the ORP water solution can achieve this reduction in the concentration of *Bacillus athrophaeus* spores when measured at least about six months after preparation, and more preferably when measured, at least about one year after preparation.

The ORP water solution administered in accordance with the invention further can produce about a six log ($10^6$) reduction in the concentration of fungal spores, such as *Aspergillis niger* spores, within about five to about ten minutes of exposure when measured at least about two months after preparation of the ORP water solution. Preferably, the ORP water solution can achieve a $10^6$ reduction in the concentration of fungal spores when measured at least about six months after preparation, and more preferably when measured at least about one year after preparation.

The ORP water solution administered in accordance with the invention can be acidic, neutral or basic, and generally can have a pH of from about 1 to about 14. Within this pH range, the ORP water solution can be safely applied in suitable quantities, e.g., to surfaces without damaging the surfaces or harming objects, such as human skin, that comes into contact with the ORP water solution. Preferably, the pH of the ORP water solution administered in accordance with the invention is from about 3 to about 8. More preferably, the pH of the ORP water solution is from about 6.4 to about 7.8, and still more preferably, the pH is from about 7.4 to about 7.6.

The ORP water solution administered in accordance with the invention can have an oxidation-reduction potential of from about −1000 millivolts (mV) to about +1150 millivolts (mV). This potential is a measure of the tendency (i.e., the potential) of a solution to either accept or transfer electrons that are sensed by a metal electrode and compared with a reference electrode in the same solution. This potential may be measured by standard techniques including, for example, measuring the electrical potential in millivolts of the ORP water solution relative to standard reference such as, e.g., a silver/silver chloride electrode.

The ORP water solution administered in accordance with the invention preferably has a potential of from about −400 mV to about +1300 mV. More preferably, the ORP water solution has a potential of from about 0 mV to about +1250 mV, and still more preferably from about +500 mV to about +1250 mV. Even more preferably, the ORP water solution administered in accordance with the present invention has a potential of from about +800 mV to about +1100 mV, and most preferably from about +800 mV to about +1000 mV.

Various ionic and other species may be present in the ORP water solution administered in accordance with the invention. For example, the ORP water solution may contain chlorine (e.g., free chlorine and bound chlorine), and dissolved oxygen and, optionally, ozone and peroxides (e.g., hydrogen peroxide). The presence of one or more of these species is believed to contribute to at least the disinfectant ability of the ORP water solution to kill a variety of microorganisms, such as bacteria and fungi, as well as viruses. Although not wishing to be bound by any particular theory, it is believed that or more of such species also may contribute the anti-inflammatory efficacy of the ORP water solution.

Free chlorine typically includes, but is not limited to, hypochlorous acid (HClO), hypochlorite ions (ClO), sodium hypochlorite (NaOCl), and precursors thereof. The ratio of hypochlorous acid to hypochlorite ion is dependent upon pH. At a pH of 7.4, hypochlorous acid levels are typically from about 25 ppm to about 75 ppm. Temperature also impacts the ratio of the free chlorine component.

Bound chlorine typically includes chlorine in chemical combination with, e.g., ammonia or organic amines (e.g., chloramines). Bound chlorine is preferably present in an amount of up to about 20 ppm.

One or more chlorine species, one or more additional superoxidized water species (e.g., one or more additional oxidizing species such as, e.g., oxygen) can be present in the ORP water solution administered in accordance with the invention in any suitable amount. The levels of these components may be measured by any suitable method, including methods known in the art.

The total amount of free chlorine species is preferably from about 10 ppm to about 400 ppm, more preferably from about 50 ppm to about 200 ppm, and most preferably from about 50 ppm to about 80 ppm. The amount of hypochlorous acid is preferably from about 15 ppm to about 35 ppm. The amount of sodium hypochlorite is preferably in the range of from about 25 ppm to about 50 ppm. Optionally, Chlorine dioxide levels are preferably less than about 5 ppm.

The chlorine content may be measured by methods known in the art, such as the DPD colorimeter method (Lamotte Company, Chestertown, Md.) or other known methods such as, e.g., methods established by the Environmental Protection Agency. In the DPD colorimeter method, a yellow color is formed by the reaction of free chlorine with N,N-diethyl-p-phenylenediamine (DPD) and the intensity is measured with a calibrated calorimeter that provides the output in parts per million. Further addition of potassium iodide turns the solution a pink color to provide the total chlorine value. The amount of bound chlorine present is then determined by subtracting free chlorine from the total chlorine.

The total amount of oxidizing chemical species present in the ORP water solution is preferably in the range of about 2 millimolar (mM), which includes the aforementioned chlorine species, oxygen species, and additional species, including those, which can be difficult to measure such as, e.g., $Cl^-$, $ClO_3$, $Cl_2^-$, and $ClO_x$.

In one embodiment, the ORP water solution administered in accordance with the invention comprises one or more chlorine species and one or more additional superoxidized water species (e.g., one or more additional oxidizing species such as, e.g., oxygen). Preferably, the chlorine species present is a free chlorine species. The free chlorine species can include one or more species selected from the group consisting of hypochlorous acid (HOCl), hypochlorite ions ($OCl^-$), and sodium hypochlorite (NaOCl), chloride ion ($Cl^-$), and optionally, chlorine dioxide ($ClO_2$), dissolved chlorine gas ($Cl_2$), precursors thereof and mixtures thereof.

In one embodiment, the ORP water solution includes one or more chlorine species or one or more precursors thereof, and one or more additional superoxidized water species or one or more precursors thereof, and, optionally, hydrogen peroxide, and is stable for at least about 24 hours, preferably for at least about one week, more preferably for at about least two months, and still more preferably for at least about six months after its preparation. Even more preferably, such ORP water solution is stable for at least about one year, and most preferably for more than about one year, e.g., at least about two years or at least about three years.

It is also preferred that the ORP water solution includes one or more chlorine species (e.g., hypocholorous acid and sodium hypochlorite) or one or more precursors thereof and one or one or more additional superoxidized water species (e.g., one or more oxygen species, dissolved oxygen) or one or more precursors thereof and has a pH of from about 6 to about 8. More preferably from about 6.2 to about 7.8, and most preferably from about 7.4 to about 7.6. An exemplary ORP water solution administered in accordance with the present invention can comprise, e.g., from about 15 ppm to about 35 ppm hypochlorous acid, from about 25 ppm to about 50 ppm sodium hypochlorite, from about 1 ppm to about 4 ppm of one or more additional superoxidized water species and a pH of from about 6.2 to about 7.8, and can be stable for at least about one week, e.g., at least about two months, at least about six months, at least about one year, or more than about one year, e.g., at least about two years or at least about three years.

While in no way limiting the present invention, it is believed that the control of pH and other variables (e.g., salinity) can provide stable ORP water solutions, which contain one or more chlorine species or precursors thereof, such as, e.g., hypochlorous acid and hypochlorite ions, and one or more additional superoxidized water species (e.g., oxygen) or one or more precursors thereof.

The ORP water solutions administered in accordance with the invention preferably comprises one or more oxidized water species which can yield free radicals (such as, e.g., hydroxyl radicals) on exposure to iron. The ORP water can optionally include one or more chemical compounds generated during the production thereof such as, e.g., sodium hydroxide (NaOH), chlorine dioxide ($ClO_2$), peroxides (e.g., hydrogen peroxide ($H_2O_2$), and ozone ($O_3$) although, it has been reported that sodium hydroxide, chlorine dioxide, hydrogen peroxide, and ozone may react with hypocholrite resulting in their consumption and the production of other chemical species.

The ORP water solution administered in accordance with the present invention can be produced by an oxidation-reduction process, e.g., by an electrolytic process or redox reaction, in which electrical energy is used to produce one or more chemical changes in an aqueous solution. Exemplary processes for preparing suitable ORP water solutions are described, e.g., in U.S. Patent Application Publication Nos. US 2005/0139808 and US 2005/0142157 (hereby incorporated by reference).

In the electrolytic process, electrical energy is introduced into and transported through water by the conduction of electrical charge from one point to another in the form of an electrical current. In order for the electrical current to arise and subsist there should be charge carriers in the water, and there should be a force that makes the carriers move. The charge carriers can be electrons, as in the case of metal and semiconductors, or they can be positive and negative ions in the case of solutions. A reduction reaction occurs at the cathode while an oxidation reaction occurs at the anode. At least some of the reductive and oxidative reactions that are believed to occur are described in International Application WO 03/048421 A1.

As used herein, water produced at an anode is referred to as anode water and water produced at a cathode is referred to as cathode water. Anode water typically contains oxidized species produced from the electrolytic reaction while cathode water typically contains reduced species from the reaction. Anode water generally has a low pH, typically of from about 1 to about 6.8. The anode water preferably contains chlorine in various forms including, for example, chlorine gas, chloride ions, hydrochloric acid and/or hypochlorous acid, or one or more precursors thereof. Oxygen in various forms is also preferably present including, for example, oxygen gas, and possibly one or more species formed during production (e.g., peroxides, and/or ozone), or one or more precursors thereof. Cathode water generally has a high pH, typically from about 7.2 to about 11. Cathode water can contain hydrogen gas, hydroxyl radicals, and/or sodium ions.

The ORP water solution administered in accordance with the invention can include a mixture of anode water (e.g., water produced in the anode chamber of an electrolytic cell) and cathode water (e.g., water produced in the cathode chamber of an electrolysis cell). Preferably, the ORP water solution administered in accordance with the present invention contains cathode water, e.g., in an amount of from about 10% by volume to about 90% by volume of the solution. More preferably, cathode water is present in the ORP water solution in an amount of from about 10% by volume to about 50% by volume, and still more preferably of from about 20% by volume to about 40% by volume of the solution, e.g., from about 20% by volume to about 30% by volume of the solution. Additionally, anode water can be present in the ORP water solution, e.g., in an amount of from about 50% by volume to about 90% by volume of the solution. Exemplary ORP water solutions can contain from about 10% by volume to about 50% by volume of cathode water and from about 50% by volume to about 90% by volume of anode water. The anode and cathode water can be produced using the three-chambered electrolysis cell shown in FIG. 1.

Figure 2:
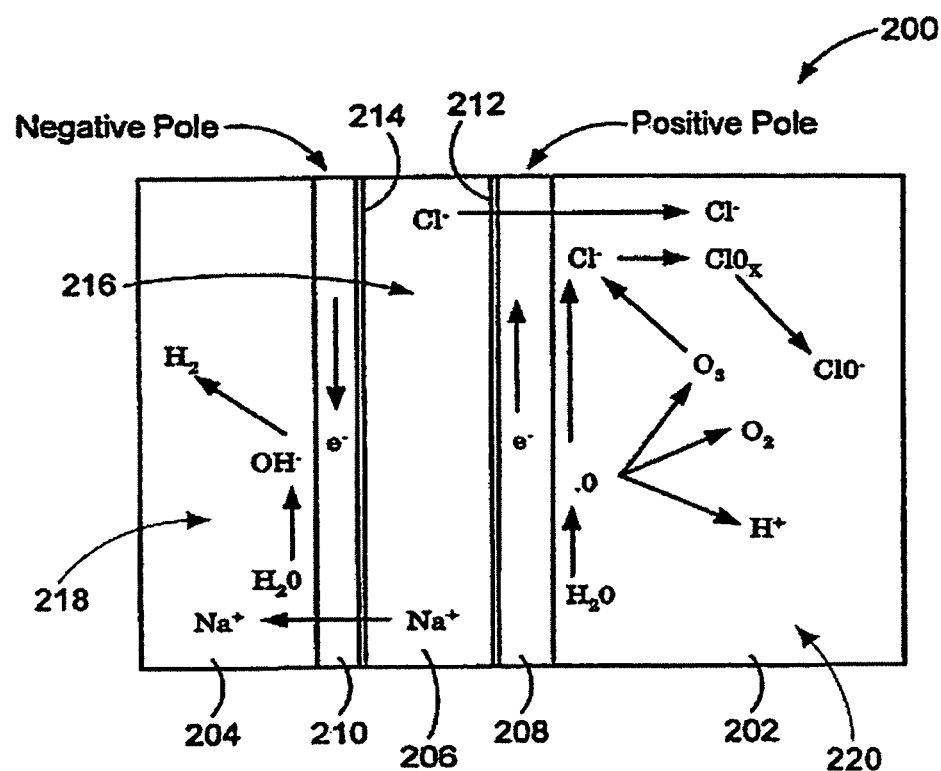
FIG. 2 illustrates a three-chambered electrolysis cell and depicts ionic species that are believed to be generated during the production process.

The ORP water solution administered in accordance with the invention is preferably produced using at least one electrolysis cell comprising an anode chamber, a cathode chamber and a salt solution chamber located between the anode and cathode chambers, wherein at least some of the anode and cathode water are combined such that the ORP water solution comprises anode water and cathode water. A diagram of an exemplary three chamber electrolysis cell that can be used in preparing an exemplary ORP water solution is shown in FIG. 2.

The electrolysis cell 100 has an anode chamber 102, cathode chamber 104 and salt solution chamber 106. The salt solution chamber is located between the anode chamber 102 and cathode chamber 104. The anode chamber 102 has an inlet 108 and outlet 110 to permit the flow of water through the anode chamber 100. The cathode chamber 104 similarly has an inlet 112 and outlet 114 to permit the flow of water through the cathode chamber 104. The salt solution chamber 106 has an inlet 116 and outlet 118. The electrolysis cell 100 preferably includes a housing to hold all of the components together.

The anode chamber 102 is separated from the salt solution chamber by an anode electrode 120 and an anion ion exchange membrane 122. The anode electrode 120 may be positioned adjacent to the anode chamber 102 with the membrane 122 located between the anode electrode 120 and the salt solution chamber 106. Alternatively, the membrane 122 may be positioned adjacent to the anode chamber 102 with the anode electrode 120 located between the membrane 122 and the salt solution chamber 106.

The cathode chamber 104 is separated from the salt solution chamber by a cathode electrode 124 and a cathode ion exchange membrane 126. The cathode electrode 124 may be positioned adjacent to the cathode chamber 104 with the membrane 126 located between the cathode electrode 124 and the salt solution chamber 106. Alternatively, the membrane 126 may be positioned adjacent to the cathode chamber 104 with the cathode electrode 124 located between the membrane 126 and the salt solution chamber 106.

The electrodes preferably are constructed of metal to permit a voltage potential to be applied between the anode chamber and cathode chamber. The metal electrodes are generally planar and have similar dimensions and cross-sectional surface area to that of the ion exchange membranes. The electrodes are configured to expose a substantial portion of the surface of the ion exchange members to the water in their respective anode chamber and cathode chamber. This permits the migration of ionic species between the salt solution chamber, anode chamber and cathode chamber. Preferably, the electrodes have a plurality of passages or apertures evenly spaced across the surface of the electrodes.

A source of electrical potential is connected to the anode electrode 120 and cathode electrode 124 so as to induce an oxidation reaction in the anode chamber 102 and a reduction reaction in the cathode chamber 104.

The ion exchange membranes 122 and 126 used in the electrolysis cell 100 may be constructed of any suitable material to permit the exchange of ions between the salt solution chamber 106 and the anode chamber 102 such as, e.g., chloride ions ($Cl^-$) and between the salt solution salt solution chamber 106 and the cathode chamber 104 such as, e.g., sodium ions ($Na^+$). The anode ion exchange membrane 122 and cathode ion exchange membrane 126 may be made of the same or different material of construction. Preferably, the anode ion exchange membrane comprises a fluorinated polymer. Suitable fluorinated polymers include, for example, perfluorosulfonic acid polymers and copolymers such as perfluorosulfonic acid/PTFE copolymers and perfluorosulfonic acid/TFE copolymers. The ion exchange membrane may be constructed of a single layer of material or multiple layers. Suitable ion exchange membrane polymers can include one or more ion exchange membrane polymers marketed under the trademark Nafion®.

The source of the water for the anode chamber 102 and cathode chamber 104 of the electrolysis cell 100 may be any suitable water supply. The water may be from a municipal water supply or alternatively pretreated prior to use in the electrolysis cell. Preferably, the water is pretreated and is selected from the group consisting of softened water, purified water, distilled water, and deionized water. More preferably, the pretreated water source is ultrapure water obtained using reverse osmosis purification equipment.

The salt water solution for use in the salt water chamber 106 can include any aqueous salt solution that contains suitable ionic species to produce the ORP water solution. Preferably, the salt water solution is an aqueous sodium chloride (NaCl) salt solution, also commonly referred to as a saline solution. Other suitable salt solutions can include other chloride salts such as potassium chloride, ammonium chloride and magnesium chloride as well as other halogen salts such as potassium and bromine salts. The salt solution can contain a mixture of salts.

The salt solution can have any suitable concentration. For example, the salt solution can be saturated or concentrated. Preferably, the salt solution is a saturated sodium chloride solution.

FIG. 2 illustrates what are believed to be various ionic species produced in the three chambered electrolysis cell useful in connection with the invention. The three chambered electrolysis cell 200 includes an anode chamber 202, cathode chamber 204, and a salt solution chamber 206. Upon application of a suitable electrical current to the anode 208 and cathode 210, the ions present in the salt solution flowing through the salt solution chamber 206 migrate through the anode ion exchange membrane 212 and cathode ion exchange membrane 214 into the water flowing through the anode chamber 202 and cathode chamber 204, respectively.

Positive ions migrate from the salt solution 216 flowing through the salt solution chamber 206 to the cathode water 218 flowing through the cathode chamber 204. Negative ions migrate from the salt solution 216 flowing through the salt solution chamber 206 to the anode water 220 flowing through the anode chamber 202.

Preferably, the salt solution 216 is aqueous sodium chloride (NaCl), which contains both sodium ions ($Na^+$) and chloride ions ($Cl^-$) ions. Positive $Na^+$ ions migrate from the salt solution 216 to the cathode water 218. Negative $Cl^-$ ions migrate from the salt solution 216 to the anode water 220.

The sodium ions and chloride ions may undergo further reaction in the anode chamber 202 and cathode chamber 204. For example, chloride ions can react with various oxygen ions and other species (e.g., oxygen containing free radicals, $O_2$, $O_3$) present in the anode water 220 to produce ClOn- and $ClO^-$. Other reactions may also take place in the anode chamber 202 including the formation of oxygen free radicals, hydrogen ions ($H^+$), oxygen (e.g., as $O_2$), ozone ($O_3$), and peroxides. In the cathode chamber 204, hydrogen gas ($H_2$), sodium hydroxide (NaOH), hydroxide ions ($OH^-$), and other radicals may be formed.

Figure 3:
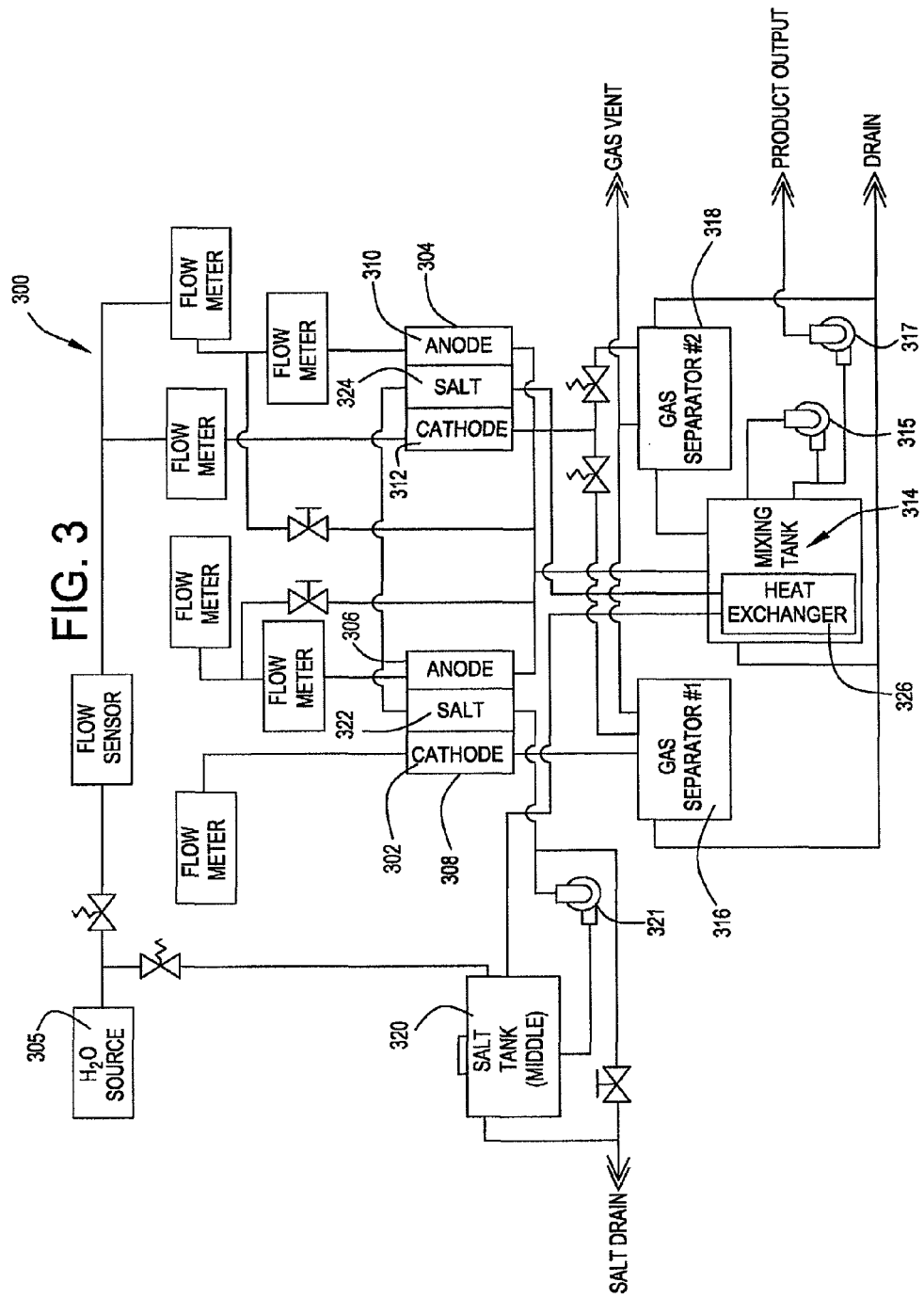
FIG. 3 is a schematic flow diagram of a process for producing an exemplary ORP water solution.

The apparatus for producing the ORP water solution also can be constructed to include at least two three chambered electrolysis cells. Each of the electrolytic cells includes an anode chamber, cathode chamber, and salt solution chamber separating the anode and cathode chambers. The apparatus includes a mixing tank for collecting the anode water produced by the electrolytic cells and a portion of the cathode water produced by one or more of the electrolytic cells. Preferably, the apparatus further includes a salt recirculation system to permit recycling of the salt solution supplied to the salt solution chambers of the electrolytic cells. A diagram of an exemplary process for producing an ORP water solution using two electrolysis cells is shown in FIG. 3.

The process 300 includes two three-chambered electrolytic cells, specifically a first electrolytic cell 302 and second electrolytic cell 304. Water is transferred, pumped or otherwise dispensed from the water source 305 to anode chamber 306 and cathode chamber 308 of the first electrolytic cell 302 and to anode chamber 310 and cathode chamber 312 of the second electrolytic cell 304. Advantageously, this process can produce from about 1 liter/minute to about 50 liters/minute of ORP water solution. The production capacity may be increased by using additional electrolytic cells. For example, three, four, five, six, seven, eight, nine, ten or more three-chambered electrolytic cells may be used to increase the output of the ORP water solution administered in accordance with the invention.

The anode water produced in the anode chamber 306 and anode chamber 310 are collected in the mixing tank 314. A portion of the cathode water produced in the cathode chamber 308 and cathode chamber 312 is collected in mixing tank 314 and combined with the anode water. The remaining portion of cathode water produced in the process is discarded. The cathode water may optionally be subjected to gas separator 316 and/or gas separator 318 prior to addition to the mixing tank 314. The gas separators remove gases such as hydrogen gas that are formed in cathode water during the production process.

The mixing tank 314 may optionally be connected to a recirculation pump 315 to permit homogenous mixing of the anode water and portion of cathode water from electrolysis cells 302 and 304. Further, the mixing tank 314 may optionally include suitable devices for monitoring the level and pH of the ORP water solution. The ORP water solution may be transferred from the mixing tank 314 via pump 317 for application in disinfection or sterilization at or near the location of the mixing tank. Alternatively, the ORP water solution may be dispensed into one or more suitable containers for shipment to a remote site (e.g., warehouse, hospital, etc.).

The process 300 further includes a salt solution recirculation system to provide the salt solution to salt solution chamber 322 of the first electrolytic cell 302 and the salt solution chamber 324 of the second electrolytic cell 304. The salt solution is prepared in the salt tank 320. The salt is transferred via pump 321 to the salt solution chambers 322 and 324. Preferably, the salt solution flows in series through salt solution chamber 322 first followed by salt solution chamber 324. Alternatively, the salt solution may be pumped to both salt solution chambers simultaneously.

Before returning to the salt tank 320, the salt solution may flow through a heat exchanger 326 in the mixing tank 314 to control the temperature of the ORP water solution as needed.

The ions present in the salt solution are depleted over time in the first electrolytic cell 302 and second electrolytic cell 304. An additional source of ions periodically can be added to the mixing tank 320 to replace the ions that are transferred to the anode water and cathode water. The additional source of ions may be used, e.g., to maintain a constant pH of the salt solution, which can to drop (i.e., become acidic) over time. The source of additional ions may be any suitable compound including, for example, salts such as, e.g., sodium chloride. Preferably, sodium hydroxide is added to the mixing tank 320 to replace the sodium ions ($Na^+$) that are transferred to the anode water and cathode water.

Following its preparation, the ORP water solution can be transferred to one or more suitable containers, e.g., a sealed container for distribution and sale to end users such as, e.g., health care facilities including, e.g., hospitals, nursing homes, doctor offices, outpatient surgical centers, dental offices, and the like. Suitable containers can include, e.g., a sealed container that maintains the sterility and stability of the ORP water solution held by the container. The container can be constructed of any material that is compatible with the ORP water solution. Preferably, the container is generally non-reactive with one or more ions or other species present in the ORP water solution.

Preferably, the container is constructed of plastic or glass. The plastic can be rigid so that the container is capable of being stored on a shelf. Alternatively, the container can be flexible, e.g., a container made of flexible plastic such as, e.g., a flexible bag.

Suitable plastics can include, e.g., polypropylene, polyester terephthalate (PET), polyolefin, cycloolefin, polycarbonate, ABS resin, polyethylene, polyvinyl chloride, and mixtures thereof. Preferably, the container comprises one or more polyethylenes selected from the group consisting of high-density polyethylene (HDPE), low-density polyethylene (LDPE), and linear low-density polyethylene (LLDPE). Most preferably, the container is constructed of high density polyethylene.

The container preferably has an opening to permit dispensing of the ORP water solution. The container opening can be sealed in any suitable manner. For example, the container can be sealed with a twist-off cap or stopper. Optionally, the opening can be further sealed with a foil layer.

The headspace gas of the sealed container can be air or any other suitable gas, which preferably does not react with one or more species in the ORP water solution. Suitable headspace gases can include, e.g., nitrogen, oxygen, and mixtures thereof.

The ORP water solution administered in accordance with the invention also can be used for the prevention or treatment of an infection, e.g., by one or more infectious pathogens such as, for example, infectious microorganisms. Such microorganisms can include, for example, viruses, bacteria, and fungi. The viruses can include, e.g., one or more viruses selected from the group consisting of adenoviruses, herpes viruses, coxsackie viruses, HIV, rhinoviruses, cornaviruses, and flu viruses. The bacteria can include, e.g., one or more bacteria selected from the group consisting of *Escherichia coli, Pseudomonas aeruginosa, Staphylococcus aureus*, and *Mycobaterium tuberculosis*. The fungi can include, e.g., one or more fungi selected from the group consisting of *Candida albicans, Bacillus subtilis* and *Bacillus athrophaeus*.

The ORP water solution administered in accordance with the invention also can be effective against adenovirus. Preferably, the ORP water solution administered in accordance with the invention preferably achieves a log-10 reduction in the adenoviral load of greater than about 2, more preferably greater than about 2.5, and still more preferably greater than about 3, after exposure to the ORP water solution for about 20 minutes, more preferably after exposure for about 15 minutes, and still more preferably after exposure for about 10 minutes. The ORP water solution administered in accordance with the invention also can be effective for reducing the viral load of HIV-1, preferably by a log reduction factor greater than about 2, more preferably by a log reduction factor of greater than about 2.5, and still more preferably by a log reduction factor of greater than about 3 after exposure to the ORP water solution for about five minutes.

In accordance with the method of the present invention, administering the ORP water solution for the prevention or treatment of infection also can serve to prevent or treat inflammation associated with the infection (or the affected tissues) as described herein.

The ORP water solution administered in accordance with the invention also can be used for treating impaired or damaged tissue, e.g., by contacting one or more impaired or damaged tissues with a therapeutically effective amount of the ORP water solution. Any suitable method can be used for contacting the impaired or damaged tissue, so as to treat the impaired or damaged tissue. For example, the impaired or damaged tissue can be treated by irrigating the tissue with the ORP water solution, so as to contact the impaired or damaged tissue with a therapeutically effective amount of the ORP water solution. The ORP water solution can be administered as a steam or a spray, or by aerosolization, nebulization or atomization, as described herein, so as to contact the impaired or damaged tissue with a therapeutically effective amount of the ORP water solution.

The ORP water solution administered in accordance with the invention can be used for treating tissues, which have been impaired or damaged, e.g., by surgery. For instance, the ORP water solution can be used for treating tissues, which have been impaired or damaged by an incision. In addition, the ORP water solution can be used for treating tissues, which have been impaired or damaged by oral surgery, graft surgery, implant surgery, transplant surgery, cauterization, amputation, radiation, chemotherapy, and combinations thereof. The oral surgery can include, for example, dental surgery such as, e.g., root canal surgery, tooth extraction, gum surgery, and the like.

The ORP water solution administered in accordance with the invention can be used for treating tissues, which have been impaired or damaged by one or more burns, cuts, abrasions, scrapes, rashes, ulcers, puncture wounds, combinations thereof, and the like, which are not necessarily caused by surgery. The ORP water solution administered in accordance with the invention can be used for treating impaired or damaged tissue, which is infected, or tissue impaired or damaged due to infection. Such infection can be caused by one or more infectious pathogens, such as, e.g., one or more microorganisms selected from the group consisting of viruses, bacteria, and fungi, as described herein.

In accordance with the present invention, administering the ORP water solution for treating impaired or damaged tissue also can serve to prevent or treat inflammation associated with the impairment or damage (or with the impaired or damaged tissue).

The ORP water solution administered in accordance with the invention also can be used as a disinfectant to eradicate microorganisms, including bacteria, viruses and spores, in a variety of settings, e.g., in the healthcare and medical device fields, to disinfect surfaces and medical equipment, and also can be applied in wound care, medical device sterilization, food sterilization, hospitals, consumer households and anti-bioterrorism. The ORP water solution can be used for disinfecting a surface, e.g., by contacting the surface with an anti-infective amount of the ORP water solution. The surface can be contacted using any suitable method. For example, the surface can be contacted by irrigating the surface with the ORP water solution, so as to disinfect the surface. Additionally, the surface can be contacted by applying the ORP water solution to the surface as a steam or a spray, or by aerosolization, nebulization or atomization, as described herein, so as to disinfect the surface. Further, the ORP water solution can be applied to the surface with a cleaning wipe, as described herein. By disinfecting a surface, the surface may be cleansed of infectious microorganisms. Alternatively (or additionally), the ORP water solution administered in accordance with the present invention can be applied to the surface to provide a barrier to infection, to thereby disinfect the surface.

The surface(s) can include one or more biological surfaces, one or more inanimate surfaces, and combinations thereof. Biological surfaces can include, for example, tissues within one or more body cavities such as, for example, the oral cavity, the sinus cavity, the cranial cavity, the abdominal cavity, and the thoracic cavity. Tissues within the oral cavity include, e.g., mouth tissue, gum tissue, tongue tissue, and throat tissue. The biological tissue also can include muscle tissue, bone tissue, organ tissue, mucosal tissue, vascular tissue, neurological tissue, and combinations thereof. Biological surfaces also include any other cultured tissue in vitro, such as primary and established cell lines, stem cells of any nature, xenotransplants, tissue substitutes (e.g. made of collagen or any other organic material in addition or not of cellular elements), any other tissue-engineered substitutes and combinations thereof.

Inanimate surfaces include, for example, surgically implantable devices, prosthetic devices, and medical devices. In accordance with the method of the present invention, the surfaces of internal organs, viscera, muscle, and the like, which may be exposed during surgery, can be disinfected, e.g., to maintain sterility of the surgical environment. In accordance with the present invention, administering the ORP water solution for disinfecting a surface also can serve to treat or prevent inflammation affecting one or more biological tissues associated with such surfaces.

The ORP water solution may also be applied to humans and/or animals to treat various conditions, including inflammation, hypersensitivity, and associated systemic effects associated with one or more of the following: surgical/open wound cleansing agent; skin pathogen disinfection (e.g., for bacteria, mycoplasmas, virus, fungi, prions); battle wound disinfection; wound healing promotion; burn healing promotion; treatment of stomach ulcers; wound irrigation; skin fungi; psoriasis; athlete's foot; pinkeye and other eye infections; ear infections (e.g., swimmer's ear); lung/nasal/sinus infections; and other medical applications on or in the human or animal body, as well as environmental remediation. The use of ORP water solutions as a tissue cell growth promoter is further described in U.S. Patent Application Publication 2002/0160053 (hereby incorporated by reference).

The ORP water solution may be used as a disinfectant, sterilization agent, decontaminant, antiseptic and/or cleanser. The ORP water solution administered in accordance with the invention is suitable for use in the following representative applications: medical, dental and/or veterinary equipment and devices; food industry (e.g., hard surfaces, fruits, vegetables, meats); hospitals/health care facilities (e.g., hard surfaces); cosmetic industry (e.g., skin cleaner); households (e.g., floors, counters, hard surfaces); electronics industry (e.g., cleaning circuitry, hard drives); and bio-terrorism (e.g., anthrax, infectious microbes).

Organisms that can be controlled, reduced, killed or eradicated by treatment with the ORP water solution include, but are not limited to, bacteria, fungi, yeasts, and viruses. Susceptible bacteria include, but are not limited to, *Escherichia coli, Staphylococcus aureus, Bacillus athrophaeus, Streptococcus pyogenes, Salmonella choleraesuis, Pseudomonas aeruginosa, Shingella dysenteriae*, and other susceptible bacteria. Fungi and yeasts that may be treated with the ORP water solution include, for example, *Candida albicans* and *Trichophyton mentagrophytes*. The ORP water solution may also be applied to viruses including, for example, adenovirus, human immunodeficiency virus (HIV), rhinovirus, influenza (e.g., influenza A), hepatitis (e.g., hepatitis A), coronavirus (responsible for Severe Acute Respiratory Syndrome (SARS)), rotavirus, respiratory syncytial virus, herpes simplex virus, varicella zoster virus, rubella virus, and other susceptible viruses.

The ORP water solution may be applied to disinfect and sterilize in any suitable manner. For example, to disinfect and sterilize medical or dental equipment, the equipment can be maintained in contact with the ORP water solution for a sufficient period of time to reduce the level of organisms present on the equipment to a desired level. Alternatively, the ORP water solution can be applied to medical or dental equipment by immersing the equipment in a container with or without the application of enhancing physical procedures, e.g. ultrasound, shakers, heaters, and the like.

For disinfection and sterilization of hard surfaces, the ORP water solution can be applied to the hard surface directly from a container in which the ORP water solution is stored. For example, the ORP water solution can be poured, sprayed or otherwise directly applied to the hard surface. The ORP water solution can then be distributed over the hard surface using a suitable substrate such as, for example, cloth, fabric or paper towel. In hospital applications, the substrate is preferably sterile. Alternatively, the ORP water solution can first be applied to a substrate such as cloth, fabric or paper towel. The wetted substrate can then be contacted with the hard surface. Alternatively, the ORP water solution can be applied to hard surfaces by dispersing the solution into the air as described herein. The ORP water solution can be applied in a similar manner to humans and animals.

The ORP water solution also can be applied with a cleaning wipe comprising a water insoluble substrate and the ORP water solution as described herein, wherein the ORP water solution is dispensed onto the substrate. The ORP water solution can be impregnated, coated, covered or otherwise applied to the substrate. Preferably, the substrate is pretreated with the ORP water solution before distribution of the cleaning wipes to end users.

The substrate for the cleaning wipe can be any suitable water-insoluble absorbent or adsorbent material. A wide variety of materials can be used as the substrate. It should have sufficient wet strength, abrasivity, loft and porosity. Further, the substrate should not adversely impact the stability of the ORP water solution. Examples include non woven substrates, woven substrates, hydroentangled substrates and sponges.

The substrate can have one or more layers. Each layer can have the same or different textures and abrasiveness. Differing textures can result from the use of different combinations of materials or from the use of different manufacturing processes or a combination thereof. The substrate should not dissolve or break apart in water. The substrate can thereby provide a vehicle for delivering the ORP water solution to the surface to be treated.

The substrate can be a single nonwoven sheet or multiple nonwoven sheets. The nonwoven sheet can be made of wood pulp, synthetic fibers, natural fibers, and blends thereof. Suitable synthetic fibers for use in the substrate can include, without limitation, polyester, rayon, nylon, polypropylene, polyethylene, other cellulose polymers, and mixtures of such fibers. The nonwovens can include nonwoven fibrous sheet materials which include meltblown, coform, air-laid, spun bond, wet laid, bonded-carded web materials, hydroentangled (also known as spunlaced) materials, and combinations thereof. These materials can comprise synthetic or natural fibers or combinations thereof. A binder can optionally be present in the substrate.

Examples of suitable nonwoven, water insoluble substrates include 100% cellulose Wadding Grade 1804 from Little Rapids Corporation, 100% polypropylene needlepunch material NB 701-2.8-W/R from American Nonwovens Corporation, a blend of cellulosic and synthetic fibres-Hydraspun 8579 from Ahlstrom Fibre Composites, and 70% Viscose/30% PES Code 9881 from PGI Nonwovens Polymer Corp. Additional examples of nonwoven substrates suitable for use in the cleaning wipes are described in U.S. Pat. Nos. 4,781,974, 4,615,937, 4,666,621, and 5,908,707, and International Patent Application Publications WO 98/03713, WO 97/40814, and WO 96/14835 (all herby incorporated by reference.).

The substrate also can be made of woven materials, such as cotton fibers, cotton/nylon blends, or other textiles. Regenerated cellulose, polyurethane foams, and the like, which are used in making sponges, also can be suitable for use.

The liquid loading capacity of the substrate should be at least about 50%-1000% of the dry weight thereof, most preferably at least about 200%-800%. This is expressed as loading ½ to 10 times the weight of the substrate. The weight of the substrate varies without limitation from about 0.01 to about 1,000 grams per square meter, most preferably 25 to 120 grams/m$^2$ (referred to as "basis weight") and typically is produced as a sheet or web which is cut, die-cut, or otherwise sized into the appropriate shape and size. The cleaning wipes will preferably have a certain wet tensile strength which is without limitation about 25 to about 250 Newtons/m, more preferably about 75-170 Newtons/m.

The ORP water solution can be dispensed, impregnated, coated, covered or otherwise applied to the substrate by any suitable method. For example, individual portions of substrate can be treated with a discrete amount of the ORP water solution. Preferably, a mass treatment of a continuous web of substrate material with the ORP water solution is carried out. The entire web of substrate material can be soaked in the ORP water solution. Alternatively, as the substrate web is spooled, or even during creation of a nonwoven substrate, the ORP water solution can be sprayed or metered onto the web. A stack of individually cut and sized portions of substrate can be impregnated or coated with the ORP water solution in its container by the manufacturer.

The cleaning wipes optionally can contain additional components to improve the properties of the wipes. For example, the cleaning wipes can further comprise polymers, surfactants, polysaccharides, polycarboxylates, polyvinyl alcohols, solvents, chelating agents, buffers, thickeners, dyes, colorants, fragrances, and mixtures thereof to improve the properties of the wipes. These optional components should not adversely impact the stability of the ORP water solution. Examples of various components that may optionally be included in the cleaning wipes are described in U.S. Pat. Nos. 6,340,663, 6,649,584 and 6,624,135 (hereby incorporated by reference).

The cleaning wipes can be individually sealed with a heat-sealable or glueable thermoplastic overwrap (such as polyethylene, Mylar, and the like). The wipes can also be packaged as numerous, individual sheets for more economical dispensing. The cleaning wipes can be prepared by first placing multiple sheets of the substrate in a dispenser and then contacting the substrate sheets with the ORP water solution administered in accordance with the invention. Alternatively, the cleaning wipes can be formed as a continuous web by applying the ORP water solution to the substrate during the manufacturing process and then loading the wetted substrate into a dispenser.

The dispenser includes, but is not limited to, a canister with a closure, or a tub with closure. The closure on the dispenser is to seal the moist wipes from the external environment and to prevent premature volatilization of the liquid ingredients.

The dispenser can be made of any suitable material that is compatible with both the substrate and the ORP water solution. For example, the dispenser can be made of plastic, such as high density polyethylene, polypropylene, polycarbonate, polyethylene terephthalate (PET), polyvinyl chloride (PVC), or other rigid plastics.

The continuous web of wipes can be threaded through a thin opening in the top of the dispenser, most preferably, through the closure. A means of sizing the desired length or size of the wipe from the web can then be desirable. A knife blade, serrated edge, or other means of cutting the web to desired size can be provided on the top of the dispenser, for non-limiting example, with the thin opening actually doubling in duty as a cutting edge. Alternatively, the continuous web of wipes can be scored, folded, segmented, perforated or partially cut into uniform or non-uniform sizes or lengths, which would then obviate the need for a sharp cutting edge. Further, the wipes can be interleaved, so that the removal of one wipe advances the next.

The ORP water solution alternatively can be dispersed into the environment through a gaseous medium, such as air. The ORP water solution can be dispersed into the air by any suitable means. For example, the ORP water solution can be formed into droplets of any suitable size and dispersed into a room.

For small scale applications, the ORP water solution can be dispensed through a spray bottle that includes a standpipe and pump. Alternatively, the ORP water solution can be packaged in aerosol containers. Aerosol containers can include the product to be dispensed, propellant, container, and valve. The valve can include both an actuator and dip tube. The contents of the container can be dispensed by pressing down on the actuator. The various components of the aerosol container should be compatible with the ORP water solution. Suitable propellants can include a liquefied halocarbon, hydrocarbon, or halocarbon-hydrocarbon blend, or a compressed gas such as carbon dioxide, nitrogen, or nitrous oxide. Aerosol systems preferably yield droplets that range in size from about 0.15 µm to about 5 µm.

Applications can also be conducted by using various hydrosurgery equipments for debriding and cleaning (e.g VersaJet devices sold in the United States by Smith and Nephew, Debritom in Europe by Medaxis, JetOx in the United States and Europe by DeRoyal or PulsaVac in Italy), irrigation systems with negative pressure (e.g., VAC Instill), and the like.

Optionally, several adjuvant therapies can also be utilized in accordance with the invention including bioengineered skin (Apligraf, Organogenesis, Inc., Canton), acellular skin substitutes (Oasis Wound Matrix, Healthpoint), ultrasonic application of ORP water solutions, and local oxygen replacement or hyperbaric oxygen treatment (such as, e.g., hyperbaric boots, the Vent-Ox System).

For some applications, the ORP water solution optionally can contain a bleaching agent. The bleaching agent can include, e.g., any suitable compound that lightens or whitens a substrate. The ORP water solution containing a bleaching agent can be used in home laundering to disinfect and sterilize bacteria and germs as well as brighten clothing. Suitable bleaching agents include, but are not limited to, chlorine-containing bleaching agents and peroxide-containing bleaching agents. Mixtures of bleaching agents also can be added to the ORP water solution. Preferably, the bleaching agent is added in the form of an aqueous solution to the ORP water solution.

Suitable chlorine-containing bleaching agents can include, e.g., chlorine, hypochlorites, N-chloro compounds, and chlorine dioxide. Preferably, the chlorine-containing bleaching agent added to the ORP water solution is sodium hypochlorite or hypochlorous acid. Other suitable chlorine-containing bleaching agents include, e.g., chlorine, calcium hypochlorite, bleach liquor (e.g., aqueous solution of calcium hypochlorite and calcium chloride), bleaching powder (e.g., mixture of calcium hypochlorite, calcium hydroxide, calcium chloride, and hydrates thereof), dibasic magnesium hypochlorite, lithium hypochlorite, chlorinated trisodium phosphate and mixtures thereof.

The addition of a bleaching agent to the ORP water solution can be carried out in any suitable manner. Preferably, an aqueous solution containing the bleaching agent is first prepared. The aqueous solution containing the bleaching agent can be prepared using household bleach (e.g., Clorox® bleach) or other suitable source of chlorine-containing bleaching agent or other bleaching agent. The bleaching agent solution can then be combined with the ORP water solution.

The bleaching agent can be added to the ORP water solution in any suitable amount. Preferably, the ORP water solution containing a bleaching agent is non-irritating to human or animal skin. Preferably, the total chloride ion content of the ORP water solution containing a chlorine-containing bleaching agent is from about 1000 ppm to about 5000 ppm, and preferably from about 1000 ppm to about 3000 ppm. The pH of the ORP water solution containing a chlorine-containing bleaching agent is preferably from about 8 to about 10, and the oxidative-reductive potential is preferably from about +700 mV to about +800 mV.

The following examples further illustrate the invention but, of course, should not be construed as in any way limiting in its scope.

EXAMPLES 1-3

These examples demonstrate the unique features of the ORP water solution used in accordance with the invention. The samples of the ORP water solution in Examples 1-3 were analyzed in accordance with the methods described herein to determine the physical properties and levels of ionic and other chemical species present in each sample. The results obtained for chlorine dioxide, ozone and hydrogen peroxide are based on standard tests used to measure such species but may be indicative of different species, which can also generate positive test results. Further, it has been reported that chlorine dioxide, ozone and hydrogen peroxide react with hypocholrite resulting in their consumption and the production of other compounds (e.g., HCl and $O_2$.) The pH, oxidative-reductive potential (ORP) and ionic species present are set forth in Table 1 for each sample of the ORP water solution.

TABLE 1

Physical characteristics and ion species present for the ORP water solution samples

|  | EXAMPLE 1 | EXAMPLE 2 | EXAMPLE 3 |
|---|---|---|---|
| pH | 7.45 | 7.44 | 7.45 |
| ORP (mV) | +879 | +881 | +874 |
| Total Cl$^-$ (ppm) | 110 | 110 | 120 |
| Bound Cl$^-$ (ppm) | 5 | 6 | 6 |

The ORP water solution has suitable physical characteristics for use in, e.g., disinfection, sterilization, cleaning, and/or the prevention and/or treatment of inflammation, sinusitis, peritonitis, or infection.

EXAMPLES 4-10

These examples demonstrate the addition of a bleaching agent to the ORP water solution according to the invention in various amounts. In particular, these examples demonstrate the antimicrobial activity and fabric bleaching ability of the compositions.

A 10% Clorox® bleach solution was prepared using distilled water. The following solutions were then prepared using the 10% bleach solution: 80% ORP water solution/20% bleach (Example 4); 60% ORP water solution/40% bleach (Example 5); 40% ORP water solution/60% bleach (Example 6); 20% ORP water solution/80% bleach (Example 7); and 0% ORP water solution/100% bleach (Example 8). Two control solutions were also used for comparison including 100% ORP water solution/0% bleach (Example 9) and an ORP water solution with 0.01% Tween 20 detergent (Example 10). The physical characteristics of these samples were determined, specifically pH, oxidative-reductive potential (ORP), total chlorine (Cl$^-$) content, hypochlorous acid (HClO$^-$) content, and were tested for chlorine dioxide content and peroxide content, the results are set forth in Table 2.

TABLE 2

Physical characteristics of ORP water solution/bleach compositions

|  | pH | ORP | Total Cl$^-$ (ppm) | HClO$^-$ (ppm) |
|---|---|---|---|---|
| Ex. 4 | 8.92 | +789 | 1248 | 62 |
| Ex. 5 | 9.20 | +782 | 2610 | 104 |
| Ex. 6 | 9.69 | +743 | 4006 | 80 |
| Ex. 7 | 9.86 | +730 | 4800 | 48 |
| Ex. 8 | 9.80 | +737 | 5000 | 50 |
| Ex. 9 | 7.06 | +901 | 64 | 32 |
| Ex. 10 | 6.86 | +914 | 51 | 26 |

The large bolus of chlorine ions added as part of the bleaching agent prevented the accurate measurement of the chlorine dioxide and peroxide levels as indicated with the n.d. designations. Also, the results obtained for chlorine dioxide and peroxide are based on standard tests used to measure such species but may be indicative of different species, which can also generate positive test results. Further, it has been reported that chlorine dioxide, ozone and hydrogen peroxide react with hypocholrite resulting in their consumption and the production of other compounds (e.g., HCl and $O_2$.) As these examples demonstrate, the hypochlorous acid levels of the ORP water solution with and without the addition of a bleaching agent are similar.

The samples of Examples 4-10 were subjected to a high spore count test using *Bacillus subtilis* var. *niger* spores (ATCC #9372 obtained from SPS Medical of Rush, New York). Spore suspensions were concentrated (by evaporation in a sterile hood) to $4 \times 10^6$ spores per 100 microliters. A 100 microliter sample of the spore suspension were mixed with 900 microliters of each of the samples in Examples 4-10. The samples were incubated at room temperature for periods of 1 to 5 minutes as set forth in Table 3. At the indicated times, 100 microliters of the incubated samples were plated onto individual TSA plates and incubated for 24 hours at 35° C.±2° C., after which the number of resulting colonies on each plate was determined. The control plates demonstrated that the starting spore concentrations were $>1 \times 10^6$ spores/100 microliters. The concentration of *Bacillus* spores for the various samples at the various incubation times (as the average of two determinations) is set forth in Table 3.

TABLE 3

*Bacillus* spore concentrations

|  | 1 minute | 2 minutes | 3 minutes | 4 minutes | 5 minutes |
|---|---|---|---|---|---|
| Ex. 4 | >>1000 | 411 | 1 | 0 | 2 |
| Ex. 5 | >>1000 | 1000 | 1 | 0 | 0 |
| Ex. 6 | >>1000 | >>1000 | >1000 | 22 | 0 |
| Ex. 7 | >>1000 | >>1000 | >1000 | 15 | 0 |
| Ex. 8 | >>1000 | >>1000 | >1000 | 3 | 1 |
| Ex. 9 | >>1000 | 74 | 0 | 0 | 0 |
| Ex 10 | >>1000 | 239 | 3 | 0 | 0 |

As these results demonstrate, as the concentration of bleach (as 10% aqueous bleach solution) increases, the amount of *Bacillus* spores killed is reduced for the samples incubated for 2-3 minutes. However, for samples incubated for 5 minutes, the bleach concentration does not impact *Bacillus* spore kill. Further, the results demonstrate that the addition of 0.01% detergent to the ORP water solution does not reduce spore kill.

The samples of Examples 4-10 were subjected to a fabric bleaching test. The fabric upon which the samples were tested was a 100% rayon children's t-shirt with dark blue dye patches. Two inch square pieces of dyed fabric were placed into 50 mL plastic tubes. Each fabric piece was covered by a sample of the solution in Examples 4-10. The elapsed time until complete bleaching was obtained, as determined by the whitening of the fabric, is set forth in Table 4.

TABLE 4

Time until complete bleaching of fabric sample

| Example | Time |
|---|---|
| Ex. 4 | 39 minutes |
| Ex. 5 | 23 minutes |
| Ex. 6 | 18 minutes |
| Ex. 7 | 19 minutes |
| Ex. 8 | 10 minutes |

TABLE 4-continued

Time until complete bleaching of fabric sample

| Example | Time |
|---------|------|
| Ex. 9 | >6 hours |
| Ex. 10 | >6 hours |

As demonstrated by these examples, as the concentration of the ORP water solution increases in the composition, the time until complete bleaching is achieved increases.

EXAMPLE 11

The purpose of this study was to assess the safety of the test an exemplary ORP water solution, Microcyn, when administered as drops into the nasal cavity of rabbits. Thirty-three rabbits were randomly assigned to two groups, Groups I and II. Group I (18 animals) served as the control group and Group II (15 animals) was dosed with the test article. On Day −1 or Day 0, body weights were recorded and blood samples were, collected for analysis of selected parameters. On Day 0, 500 μL of sterile saline was administered to the Group I animals and 500 μL of the test article (at a 50% concentration) was administered to Group n annuals. Both the control and the test articles were administered twice daily as drops into the right nostril. The animals were dosed in the same manner on Days 1-6. Animals were observed daily for signs of pharmacologic and/or toxicologic effects with special attention paid to the nose. Body weights were recorded weekly through study termination. On Day 7, one-third of the animals from each group were selected for blood collection, sacrifice and necropsy. The remaining animals continued to be dosed through Day 14, when half of the animals from each group were selected for blood collection, sacrifice and necropsy. On Day 21, after a 7-day recovery period), the remaining animals had blood collected and were sacrificed and necropsied. Samples of the nasal mucosa from both nostrils were collected from each animal for histopathological analysis.

The necropsy consisted of gross observations of the respiratory tract. The entire nasal passage and associated bone were taken and fixed in buffered formalin. Samples of any visible abnormalities in the respiratory tract were also collected for histopathology. Three biopsy samples (anterior, middle and posterior nasal cavity) per nostril (treated right and untreated left) were examined. The microscopic histopathology of the nasal mucosa included: integrity of epithelium, presence or loss of epithelial cilia, inflammatory cell infiltration, edema, presence of goblet cells, hyperplasia of glands, changes in number or characteristics of blood vessels and any other changes or observations.

The results (in-life observations including nasal observations, body weights, blood analysis, gross necropsy and histopathology results) from the test group were compared to the control group. The test group was not significantly different from animals treated with saline in terms of mild irritation.

EXAMPLE 12

This example illustrates the lack of toxicity from the use of an exemplary ORP water solution.

The characterization of local and systemic toxicity from topically applied Microcyn 60 to a deep wound was evaluated in rats. No abnormalities, significant differences in the parameters of the blood chemistry or hematic cytology were observed, nor anomalies in the autopsies. The skin irritation gradings and the histopathology of the wounds and the tissues around the place of application did not reveal any difference between the wounds treated with Microcyn 60 and those of the control group treated with saline solution.

The systemic toxicity of Microcyn 60 was also evaluated by means of an intraperitoneal injection in mice. For this, five mice were injected with a single dose (50 mL/kg) of Microcyn 60 by the intraperitoneal route. In the same way, five control mice were injected with a single dose (50 mL/kg) of saline solution (sodium chloride at 0.9%). In this investigation, neither mortality nor any evidence of systemic toxicity was observed in any of the animals that received the single intraperitoneal dose of Microcyn 60, indicating that the $LD_{50}$ is above 50 mL/kg.

Microcyn 60 was administered by the oral route to rats to allow its absorption and to characterize any inherent toxic effect of the product. In this study, a single dose (4.98 mL/kg) was administered by esophageal tube to three albino rats of the Sprague-Dawley strain. There was no mortality, nor were there clinical signs or abnormalities in the autopsies of any of the animals exposed to the single oral dose of Microcyn 60.

The potential of topically applied Microcyn 60 for ocular irritation was also evaluated in rabbits. Ocular irritation was not observed nor any other clinical sign in any animal exposed to Microcyn 60 by topical administration through the ocular route.

Microcyn 60 was applied by the inhalatory route to rats to determine potential acute toxicity by inhalation. All the animals showed a very slight or slight reduction in activity and piloerection after the exposure, but they were all asymptomatic on the following day. Mortality or abnormalities were not observed at autopsy of the animals exposed to Microcyn 60 by inhalation.

Evaluation of the potential for sensitization of the skin with Microcyn 60 was carried out in guinea pigs using a modified occlusion patch method (Buehler). Irritation was not observed in the animals of the control group after a simple treatment challenge, nor in the animals evaluated (treated by induction) after challenge with the treatment. These studies demonstrate that Microcyn 60 does not provoke a sensitizing reaction.

Thus, when it has been applied to the intact skin, deep open dermal wounds, in the conjunctival sac, by oral and inhalation routes or by means of intraperitoneal injection, Microcyn 60 has not shown adverse effects related to the product. There is also experience in having treated more than thousands of patients with wounds of very diverse nature in the skin and mucosae, with excellent antiseptic and cosmetic results. Accordingly, topically applied Microcyn 60 should be effective and well-tolerated in this clinical trial.

Microcyn 60 is packaged in transparent 240 mL PET sealed bottles. This product is stored at ambient temperature and remains stable for up to 2 years in such bottles. From its profile of high biological safety, Microcyn 60 can be safely disposed of, e.g., emptied into the sink without risk of contamination or corrosion.

EXAMPLE 13

This example illustrates a clinical study, which can be used to determine the effectiveness of an exemplary ORP water solution for treating pharyngitis.

Multiple microbial trials have been run with Microcyn 60, both in the United States and in Mexico. Eradication of more than 90% of the bacteria occurs in the first few seconds of exposure. The antibacterial and antimycotic activity that Microcyn 60 exhibits in accordance with this standard is summarized in Table 5.

TABLE 5

Kill times.

| Bacterium | Catalog | Time of action (reduction below 99.999%) |
|---|---|---|
| Ps. Aeruginosa | ATCC 25619 | 1 min |
| St. aureus | ATCC 6538 | 1 min |
| E. coli | ATCC 11229 | 1 min |
| S. typhi | CDC 99 | 1 min |
| C. albicans | ATCC 9372 | 1 min |
| B. subtilis | | |
| Low spore ($10^4$) | | 10 min |
| High spore ($10^6$) | | 15 min |

The sporicidal activity trial was carried out in accordance with the PAHO [Pan-American Health Organization]/WHO protocol.

The virucidal activity of Microcyn 60 has recently been confirmed in studies carried out in the United States against HIV and its activity against *Listeria monocytogenes*, MRSA and *Mycobacterium tuberculosis* has also been demonstrated. Thus, it has been demonstrated that Microcyn 60, when it is administered as recommended, can eradicate bacteria, fungi, viruses and spores from one to fifteen minutes of exposure.

Additionally, the following is a clinical study that can be used to assess the efficacy of Microcyn 60 for the treatment of pharyngitis/tonsilitis. In this study, 40 patients with acute pharyngitis/tonsillitis caused by group A β-hemolytic *Streptococcus* and who have not received treatment are recruited. The inclusion criteria are as follows: age 12 to 40 years and two or more of the following symptoms: oropharyngeal burning; pain on swallowing; pharyngeal erythema or of the tonsils (with or without exudate); cervical lymphadenopathy; and positive immunoassay for group A *Streptococcus* antigen (StrepA Test-Abbott Labs). The exclusion criteria are as follows: fever >38° C.; bronchospasm (excluded by the clinic); severe cough; sinusitis-rhinitis (excluded by the clinic); esophageal reflux (excluded by the clinic); use of antibiotics in the two weeks prior to the study; patients who have taken part in another clinical study in the last 8 weeks; rheumatic fever; poststreptococcal glomerulonephritis; severe chronic cardiopathy; severe renal, hepatic or pulmonary insufficiencies; and pregnancy or lactation.

At the beginning of the study, patients may use such concomitant medicines as antipyretics and analgesics, including paracetamol and acetylsalicylics but not anti-inflammatories such as ibuprofen, Mesulid, COX-2 inhibitors, or steroids. Written informed consent must be obtained before the patient submits to any specific procedure of the study.

The patients are evaluated in three visits. In the first visit, the patient clinically presents acute pharyngitis/tonsillitis, and the clinical history is taken, and a medical examination, rapid immunoassay for *Streptococcus*, and taking of a pharyngeal exudate is carried out. After being declared eligible and after having signed the letter of informed consent, the patient is prescribed two oropharyngeal cleansings of 30 sec and 5 mL Microcyn 60 each. These rinsings are done every 3 h for a total of four times a day for 3 days.

The second is made 72 h after having been treated with Microcyn 60. In the second visit, the clinical evolution and side effects of Microcyn 60 are evaluated. A new pharyngeal exudate is taken, and it will be decided, in accordance with the clinical evolution, if the continuing treatment will be with antibiotics or a palliative. A third visit is done after 10 days to discharge the patient.

To be eligible and clinically evaluated in this study, each patient must present A β-hemolytic *Streptococcus* pharyngitis/tonsillitis confirmed by culture. All the patients must comply with 18 rinsings of 30 sec and 5 mL of Microcyn 60 each, or a maximum of 24 rinsings in the space of 72 h.

The primary parameter of efficacy is a reduction by 3 orders of magnitude in the bacterial load of the initial culture compared to the culture taken after the administration of Microcyn 60. This bacteriological evaluation is realized 72 h after treatment with Microcyn 60. Secondary parameters of efficacy are the improvement reported clinically, with particular emphasis on the reduction of pharyngeal pain and dysphagia. Clinical symptoms are reported in visits 1, 2 and 3.

Tolerance is evaluated by reports of adverse events. An adverse event is defined as any symptomatic declaration of the patient who submits to the treatment with Microcyn 60, related or not to the antiseptic, that appears in the course of the treatment.

The results of bacteriological efficacy (the principal criterion of efficacy) are issued by a bacteriologist independently of the clinical symptoms. The tests for the group A *Streptococcus* antigen and the initial pharyngeal exudate culture are done in the first visit (Visit 1), in accordance with the Schedule of Evaluations and before the administration of Microcyn 60. The second taking and culture of pharyngeal exudate is carried out 72 h after the administration of Microcyn 60 (Visit 2). An antibiogram is done on all the cultures to determine the bacterial resistance to penicillin, erythromycin, clarithromycin and lincomycin by means of the standard diffusion disc test. Bacteriological efficacy is defined as the reduction by three orders of magnitude of the bacterial count between the initial culture and the culture taken 72 h after administering Microcyn 60.

Bacteriological failure is indicated by a reduction of less than three orders of magnitude of the bacterial count in the culture at 72 h posttreatment. Indeterminate responses are documented in those cases in which the transport of the sample has been delayed for more than 48 h, in those cases in which the swab has not been immersed in the transport medium, or in those cases in which the sample has been lost. These cases are outside the analysis of the study and are replaced by new cases until those of forty eligible patients have been completed.

The follow-up and reporting phase begins when the patient finishes the administration of Microcyn 60, and from the second visit. In this evaluation, according to the clinical evolution and the presence of possible adverse effects, the patients are categorized as follows:

Therapeutic failures if their initial signs and symptoms have not been eliminated or if there is worsening of their general condition with systemic symptoms. In these cases an oral antibiotic is prescribed, such as procaine penicillin, clarithromycin or azithromycin at the dose and for the time that the treating doctor indicates, and they are evaluated in one week.

Clinically cured if the symptoms and signs that were present in Visit 1 have been eliminated. In these cases in which the acute process is resolved, the patient is discharged and reported as clinically cured. In any case, the patient is asked to return for a third check-up visit in one week.

Indeterminate evolution. The evolution of any patient who could not have been evaluated clinically for any good reason; for example, a coinfection, or if the evaluation was done very late, later than 72 h. In these cases, the patients is still able to be included in the analysis of the study provided it is possible to document the result of the pharyngeal exudate and culture at 72 h.

The statistical analysis used in this clinical study takes into account all the patients who have received at least 18 rinsings of Microcyn 60 of 30 sec each in a period of 72 h. This same criterion is considered to include any patient in the analysis of tolerance. The principal criterion for analysis of efficacy is the reduction of the bacterial count of β-hemolytic Streptococcus by three orders of magnitude in the culture carried out at 72 h posttreatment with Microcyn 60. The statistical analysis is realized by means of a Wilcoxon paired samples test. Statistical analysis of the clinical variables is realized using the ANOVA test for quantitative variables. The minimal evaluable number of patients is 30 patients.

An adverse event is any contrary medical occurrence in a patient or subject of clinical investigation to whom a pharmaceutical product is administered and that does not necessarily have a causal relationship with that medicine. An adverse event can, therefore, be any unfavorable and unintended sign (including an abnormal laboratory finding), symptom or illness temporarily associated with the use of a medical product, whether it is considered to be related to this use or not. Preexisting conditions that deteriorate during a study are reported as adverse events.

The treatment is suspended at any time during the 72 h of duration in case of adverse events that are moderate to severe in intensity. Subsequent treatment is determined by the treating doctor. In accordance with this example, the effectiveness of an ORP water solution of the present invention for treating sinusitis is thus demonstrated.

EXAMPLE 14

This example demonstrates the viricidal activity of an exemplary ORP water solution against Adenovirus-serotype 5. For this example Adenoviral (Ad) vectors based on human adenovirus type 5 which are E1a-, partially E1-b, and partially E3-deleted were used. A shuttle plasmid containing the Green Fluorescent Protein (GFP) reporter gene under the transcriptional control of pCMV was prepared (pAd-Track). Homologous recombination of this pShuttle plasmid with AdEasy 1 plasmid was carried out in electrocompetent bacteria. Clones that had inserts were tested by restriction endonuclease digestions. Once confirmed, supercoiled plasmid DMA was transformed into DH1 OB cells for large scale amplification. Subsequently, 293 cells (ATCC 1573) were cultured in serum-free medium (OptiMEM-GIBCO) and transfected with recombinant plasmid digested with Pad. Infected cells were monitored for cytopathic effect, collected and lysed with three cycles of freezing and thawing. The resultant viruses (AdGFP) were purified with AdenoPure columns (BD Clontech) according to the manufacturer's instructions. Viruses were quantitated by OD 260/280. Final yield was $1.52 \times 10^{11}$ pfu/mL.

The efficacy of the ORP water solution for inactivating adenovirus encoding the green fluorescence protein gene (AdGFP), was evaluated using a test based on the detection of fluorescence emission from HeLa cells infected with either, control AdGFP viruses or ORP water solution-treated AdGFP, using fluorescence-activated flow cytometry. Infection of HeLa cells was always carried out with $7.5 \times 10^7$ pfu/mL (i.e. 150 m.o.i.). In all test conditions, cells appeared normal under light microscopy. The background fluorescence measured in control HeLa cells was 0.06%. After infection with control AdGFP, 88.51% of HeLa cells expressed GFP. Following exposure to the ORP water solution, adenovirus infectivity decreased inversely proportionally to the exposure period. Accordingly, ORP water solution-treated virus for 1, 5, and 10 min could only express GFP in 2.8%, 0.13%, and 0.09% of HeLa cell cultures, respectively. Considering the autofluorescence and the initial viral load for all tested conditions (i.e. $7.5 \times 10^7$ pfu), the infectious titer was $6.6 \times 10^7$ pfu in the control AdGFP-HeLa group. In the groups where the virus had been treated with the ORP water solution, the infectious titers were $2.0 \times 10^6$, $5.2 \times 10^4$ and $2.2 \times 10^4$ at one, five and ten minutes of virus exposure to the ORP water solution, respectively. Therefore, the log-10 reduction factor was 1.5, 3.1, and 3.5 at one, five and ten minutes of viral exposure to the ORP water solution. Taken together, these results demonstrate that the virus exposure to the ORP water solution for 5 minutes achieves a log-10 reduction in the viral load of >3.

EXAMPLE 15

This example demonstrates the viricidal effectiveness of an exemplary ORP water solution against HIV using the United States Environmental Protection Agency protocol for disinfection of inanimate environmental surfaces.

The SF33 strain of HIV-1 used for this study. Peripheral blood mononuclear cells from healthy donors were activated with PHA (3 µg/mL, Sigma) and human IL-2 (20 U/mL, Roche) in HUT media for three days. Cells were washed and infected with SF33 strain. Supernatant was collected on days 4 and 6, and tested for the p24 HIV-1 antigen by ELISA (Beckman Coulter). Supernatant was centrifuged to remove cell and debris at 3000 RPM for 20 min at room temperature. Supernatant was removed, aliquoted, and the virus was stored at −80° C. until the day of use.

Frozen aliquots were thawed at 37° C. for two minutes immediately prior to its use. Serial logarithmic dilutions (−1 to −5) in HUT medium were used. Films of virus were prepared by spreading 0.2 ml of virus inoculum uniformly over the bottoms of 55 cm² sterile polystyrene Petri dishes. The virus films were air-dried at room temperature (21° C.) in a biological safety cabinet until they looked visibly dry (20 minutes). (To assure that the virus strain (SF33) was capable of replicating and causing cytopathic effects, the procedure was repeated with a viral suspension that had remained in HUT medium without being dried.)

The control film was exposed to 2 ml HUT media for five minutes. The virus was then scraped and diluted. Separate dried films were exposed to 2 ml each of the ORP water solution for five minutes at room temperature. Following the exposure time, the plates were scraped and their contents were resuspended. The virus-ORP water solution mixture was immediately diluted (10:1) in HUT medium. Serial log dilutions of this resulting suspension were assayed for infectivity. (To control for a possible direct cytotoxic effect of ORP water solution on MT-2 cells, a 2 ml aliquot of ORP water solution was diluted serially (10:1 to 10:5) in medium and inoculated into MT-2 cell cultures.)

The MT-2 cell line was used as the indicator cell line in the infectivity assays. This line shows a cytopathic effect consisting of sincitia formation when infected with HIV-1. Four microwells were inoculated with 0.2 ml of each dilution of the reconstituted virus suspension from test (reconstituted in ORP water) and control (reconstituted with control medium) groups. Uninfected cell controls were inoculated with test medium only. Cultures were incubated at 37° C. and 5% $CO_2$.

The cultures were scored periodically every two days for the presence or absence of cytopathic effect as well as presence of p24-HIV-1 antigen by ELISA. Experimental infection with control HIV-1 exerted a cytopathic effect and Ag p24 protein release into the supernatant in infected MT-2 cultures. In contrast, treatment of HIV-1 with the ORP water solution for five minutes, achieved a log reduction factor >3 in the viral load as measured in MT-2 cultures by both assays. These results thus demonstrate the level of efficacy that is in conformity with the EPA requirements for HIV-1 virucidal activity on inanimate surfaces.

EXAMPLE 16

This example demonstrates the effect of an exemplary ORP water solution versus hydrogen peroxide (HP) on the viability of human diploid fibroblasts (HDFs). To study this potential toxicity, HDFs were exposed in vitro to ORP water solution and hydrogen peroxide (HP). HP is known to be toxic to eukaryotic cells, increasing apoptosis and necrosis and reducing cellular viability. In this example, cell viability, apoptosis and necrosis were measured in HDFs exposed to pure ORP water solution and 880 mM HP (a concentration employed for antiseptic uses of HP) for 5 and 30 minutes.

Figure 4A:
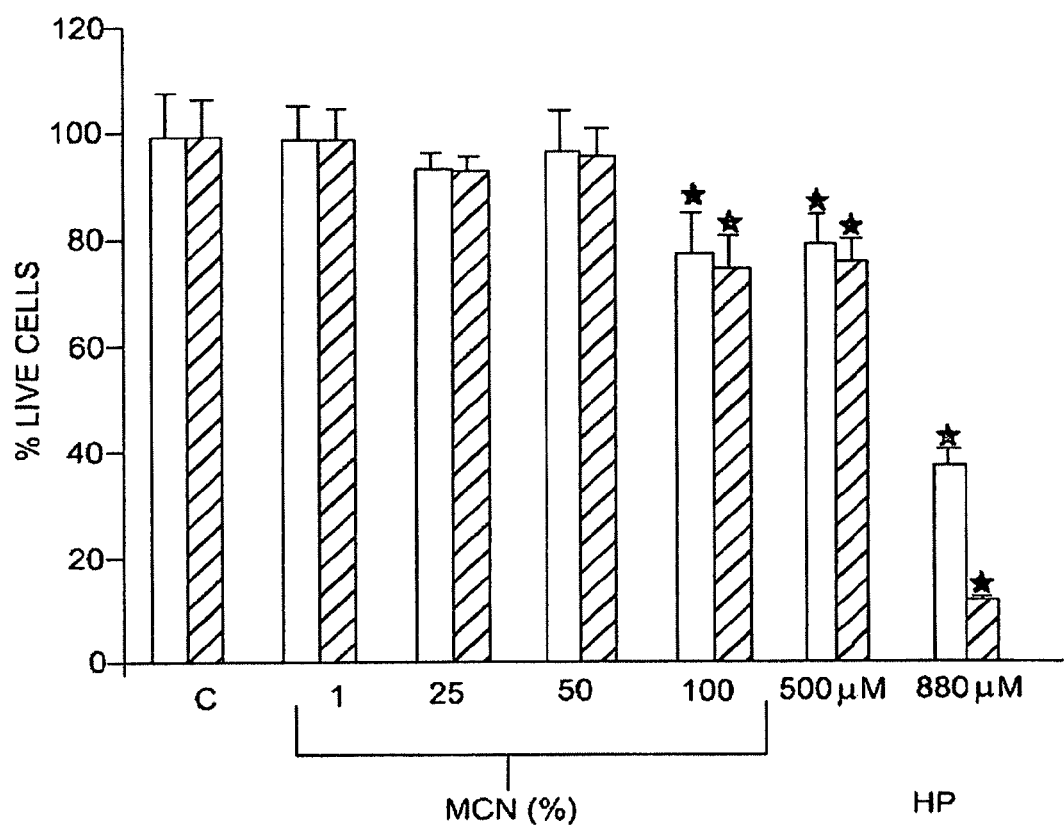
FIG. 4A-4C depict a graphical comparison of cell viability, apoptosis and necrosis in human diploid fibroblasts (HDFs) treated with an exemplary ORP water solution (MCN) versus hydrogen peroxide (HP).
Figure 4B:
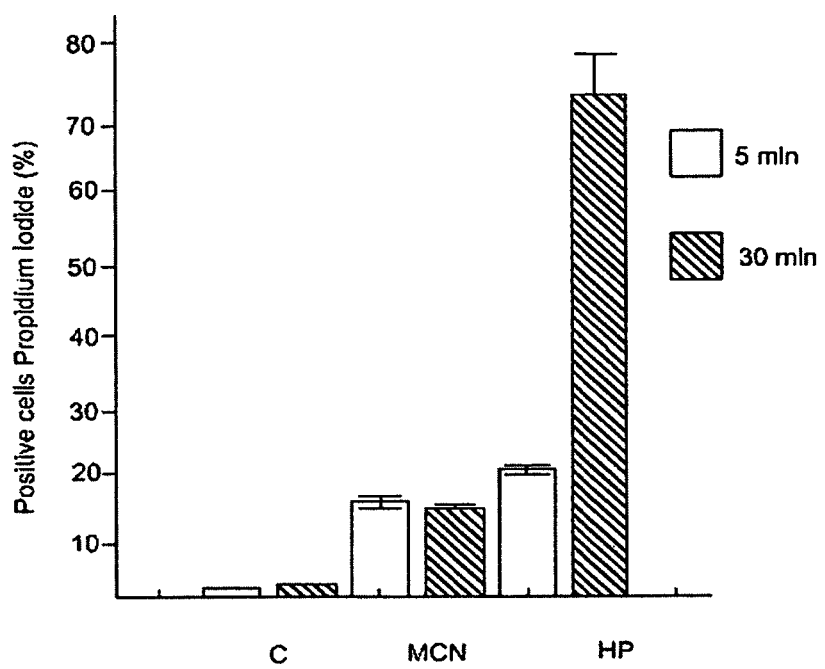
Figure 4C:
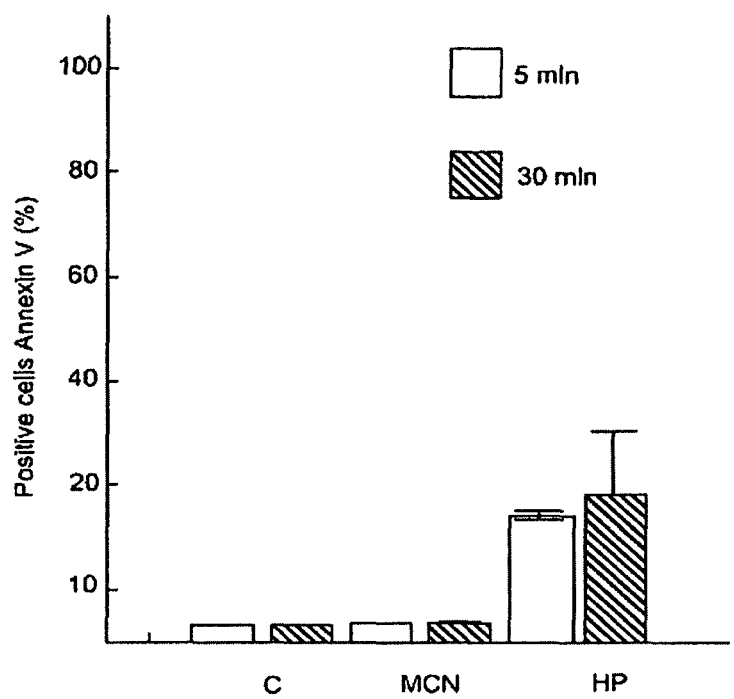

HDF cultures were obtained from three different foreskins, which were pooled and cryopreserved together for the purpose of this study. Only diploid cells were used for all experiments. On cell cycle analysis, DNA diploidy was defined as the presence of a single G0-G1 peak with a CV</=7% and a corresponding G2/M peak collected from at least 20,000 total events. FIG. 4A-4C disclose the results where exposure times of 5 and 30 minutes are depicted in white and black bars, respectively. Simultaneous analyses of these parameters were performed in the same cell populations by flow cytometry using: A) 7-aminoactinomycin D (7AAD); B) Annexin V-FITC; and C) Propidium iodide. FIG. 4A-4C disclose percentage values expressed as mean±SD (n=3).

Cell viability was 75% and 55% after a 5 minute exposure to antiseptic concentrations of full strength-ORP water solution and 880 mM HP, respectively (FIG. 4A). The effect of full strength ORP water solution on cell viability was comparable to a very diluted HP solution considered sublethal but not disinfectant (i.e. 500 µM). If the exposure was prolonged to 30 min, cell viability further decreased to 70% and 5%, respectively. Apparently, the ORP water solution induced cell death through necrosis because 15% of the cells incorporated propidium iodide in the flow cytometry analysis at both times (FIG. 4C). Apoptosis does not seem to be the mechanism by which the ORP water solution induces cell death because only 3% of ORP water solution-treated cells exposed Annexin-V in the cellular surface (a marker of apoptosis) (FIG. 4B). This percentage was actually similar to the one measured in the control group. On the contrary, HP induced necrosis in 20% and 75% of treated cells and apoptosis in 15% and 20% after 5 and 30 min of exposure, respectively. Altogether these results show that the (undiluted) ORP water solution is far less toxic for HDFs than an antiseptic concentration of HP.

EXAMPLE 17

This example demonstrates the effect of an exemplary ORP water solution relative to hydrogen peroxide (HP) on oxidative DNA damage and formation of the DNA adduct 8-hydroxy-2'-deoxiguanosine (8-OHdG) in HDFs. It is known that the production of 8-OHdG adducts in a cell is a marker of oxidative damage at specific residues of DNA. In addition, high cellular levels of this adduct correlate with mutagenesis, carcinogenesis and cellular aging.

Figure 5:
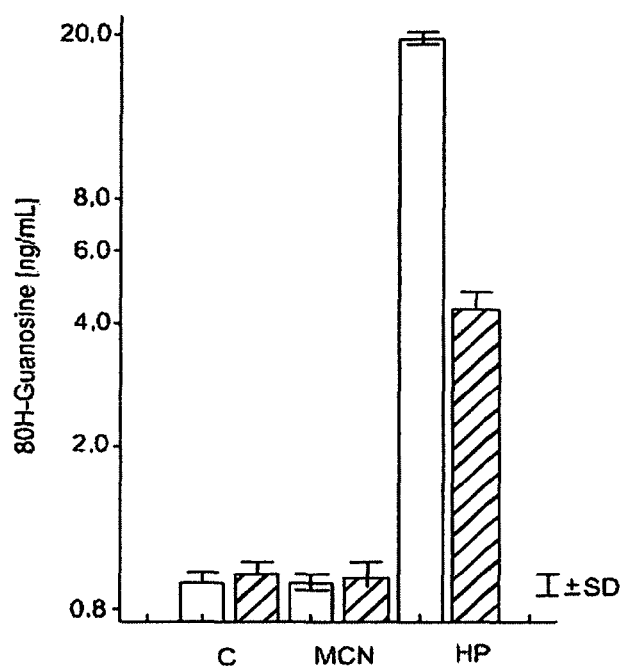
FIG. 5 is a graphical comparison of the levels of 8-hydroxy-2'-deoxyguanosine (8-OHdG) adducts in HDFs treated with an exemplary ORP water solution (MCN) versus 500 µM hydrogen peroxide (HP).

FIG. 5 shows the levels of 8-OHdG adducts present in DNA samples from HDFs after control treatments, ORP water solution treatments and HP-treatments for 30 minutes. DNA was extracted right after the exposure (T0, white bars) or three hours after the challenge period (T3, black bars). DNA was digested and the 8-OHdG adducts were measured by ELISA kit as per the manufacturer's instructions. Values are shown (ng/mL) as mean±SD (n=3). The exposure to ORP water solution for 30 minutes did not increase the formation of adducts in the treated cells in comparison to control cells after incubation for 30 minutes. In contrast, the treatment with 500 µM HP for 30 minutes increased the number of 8-OHdG adducts by about 25 fold relative to the control-treated or ORP water solution-treated cells.

The ORP water solution-treated cells were able to decrease the levels of 8-OHdG adducts if left in supplemented DMEM for 3 hours after exposure to the ORP water solution. Despite being allowed the same 3 hour recovery period, HP-treated cells still presented about 5 times more adducts than control-treated or ORP water solution treated cells. Altogether, these results demonstrate that acute exposure to the ORP water solution does not induce significant DNA oxidative damage. These results also indicate that the ORP water solution will not likely induce mutagenesis or carcinogenesis in vitro or in vivo.

EXAMPLE 18

Figure 6:
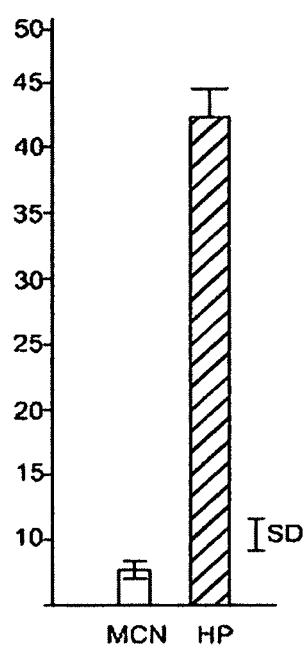
FIG. 6 illustrates cellular senescence demonstrated by β-galactosidase expression in HDFs after chronic exposure to low concentrations of an exemplary ORP water solution (MCN) versus hydrogen peroxide (HP).

This example demonstrates the effects on HDFs of chronic exposure to low concentrations of an exemplary ORP water solution versus HP. It is known that chronic oxidative stress induces premature aging of cells. In order to mimic a prolonged oxidative stress, primary HDF cultures were chronically exposed to low concentrations of the ORP water solution (10%) or HP (5 µM) during 20 population doublings. The expression and activity of the SA-β-galactosidase enzyme has previously been associated with the senescence process in vivo and in vitro. In this example the expression of the SA-β-galactosidase enzyme was analyzed after one month of continuous exposure of HDF to the ORP water solution or HP. The results are depicted in FIG. 6. The expression of the enzyme SA-β-galactosidase was analyzed by counting the number of blue cells in 20 microscopic fields. FIG. 6 shows that only HP treatment accelerated the aging of cells as indicated by the number of cells over-expressing SA-β-galactosidase (n=3). Chronic treatment with a low dose of HP increased the SA-β-Gal expression in 86% of cells while the treatment with the ORP water solution did not induce the overexpression of this protein. It can be concluded from this example that ORP water solution is not an inducer of premature cellular aging.

EXAMPLE 19

This example demonstrates the effect of an exemplary ORP water solution on the reduction of peritoneal bacterial load and on the reduction in the length of hospital stay in patients with peritonitis. All patients admitted to the Hospital Ruben Leñero in Mexico City from June 2004 to January 2005, and with a diagnosis of acute generalized, secondary peritonitis, were included in the ORP water solution-treated group. Secondary peritonitis was defined as the result of the loss of integrity of the gastrointestinal or genito-urinary tract leading to contamination of the peritoneal space. Retrospective analysis of paired-cases presenting similar peritoneal infections between 2003 and 2004 at the same Institution was undertaken for the control group. Twenty consecutive patients were prospectively included in the ORP water solution-treated group (i.e. study group).

Upon admission, all patients underwent open surgery and intra-operative peritoneal lavage ("IOPL") of all quadrants of the abdomen. Intraoperative peritoneal-culture samples were taken in both groups. IOPL was performed with 10 L of saline solution in both groups and followed by 5 L of the ORP water solution in the study group only. The excess ORP water solution was removed and no further rinsing was conducted. The abdominal cavity was covered with a plastic mesh in both groups. However, in the study group, a dressing soaked in ORP water solution was left on top of the mesh. The dressing was changed t.i.d. Emperic antimicrobial therapy was started in all patients with two antibiotics including clindamycin and cefotaxime or amikacin. Post-operative management in the study group included daily irrigation of the mesh with 100 mL of the ORP water solution t.i.d., without further rinsing or lavage. Severe cases of peritonitis required re-laparotomy and IOPL every 72 hours. Cultures of the peritoneal fluid for aerobic bacteria and fungi were taken every 72 hours in both groups for up to one week. The duration of length of stay in the hospital was recorded.

Twenty control cases were selected from the medical records of the Institution and paired to the study group by age, sex and etiology of peritonitis. The control and study populations were comparable in age, sex and prognostic factors at entry. The anatomic origin and etiology of peritonitis was also similar for both groups (Table 6).

TABLE 6

| Diagnoses. | | | | |
|---|---|---|---|---|
| DIAGNOSIS | CONTROL | STUDY | TOTAL | % |
| Appendicitis | 3 | 6 | 9 | 23.0 |
| Post-trauma | 1 | 3 | 4 | 10.0 |
| Pancreatitis | 6 | 3 | 9 | 23.0 |
| Cholecystitis | 1 | 2 | 3 | 7.5 |
| Colon cancer | 0 | 1 | 1 | 2.5 |
| Small bowel fistula | 4 | 1 | 5 | 12.5 |
| Diverticulitis | 1 | 1 | 2 | 5.0 |
| Gastric perforation | 4 | 0 | 4 | 10.0 |
| Other Organ perforation | 0 | 2 | 2 | 5.0 |
| Other | 0 | 1 | 1 | 2.5 |
| TOTAL | 20 | 20 | 40 | 100.0 |

Post-operative peritonitis was present in 19 and 17 patients of the control and study groups, respectively. All cases underwent surgical treatment followed by IOPL. The types of surgeries performed in control/study groups, were: appendicectomy (3/6), gastric resection (4/0), cholecystectomy (1/2), pancreatic necrosectomy (6/3), small bowel suture/resection with anastomosis (4/3), Hartman's operation (1/1), colonic resection (0/1) and miscellaneous (1/4). The use of antibiotics was very similar in both groups. For control and study groups, three antibiotics were administered in 16 and 15 patients and more than 3 antibiotics in 4 and 5 cases, respectively. Patients were kept at the ICU and were mechanically ventilated post-operatively. Peri-operative intra-abdominal samples were taken in all 40 patients (Table 7).

TABLE 7

Microorganisms isolated from intraperitoneal samples and length of hospital stay in patients with peritonitis.

| | CONTROL GROUP | | | STUDY GROUP | | |
|---|---|---|---|---|---|---|
| | Isolated strains (n) | | | Isolated strains (n) | | |
| Organism | Peri-op | Post-op | Hospital Days | Peri-op | Post-op | Hospital Days |
| C. albicans | 10 | 7 | 19.4 | 7 | 0 | 6.3 |
| E. coli | 3 | 2 | 17.6 | 6 | 1 | 10.2 |
| S. aureus | 10 | 9 | 22.3 | 8 | 1 | 14.1 |
| coagulase neg. Staph. | 0 | 0 | 0 | 2 | 0 | 17.8 |
| A. baumanii | 0 | 0 | 0 | 1 | 0 | 22.4 |
| E. faecalis | 3 | 3 | 23.7 | 1 | 0 | 28.6 |
| A. xilosoxidans | 0 | 0 | 0 | 1 | 0 | 28.6 |
| P. aeruginosa | 2 | 2 | 24.0 | 3 | 0 | 33.9 |
| E. coacae | 1 | 1 | 13.0 | 1 | 0 | 37.0 |
| TOTAL | 29 | 24 | 31.9 | 30 | 2 | 22.4 |

Samples were obtained in the peri-operative period and in the following week after intra-operative lavage with saline solution only (control group) or saline solution and ORP water solution (study group). The average hospital stay was then analyzed for each microorganism isolated at entry and for the whole group.

Peri-operative samples were taken in all 40 patients (Table 7). The average numbers of microorganisms grown from these samples were 29 in the control and 30 in the study group. The microorganisms isolated are shown in Table 8. *Escherichia coli, Enterococcus, Staphylococcus aureus, Pseudomonas aeruginosa* and fungi were isolated from these groups in 3/6, 4/2, 10/8, 2/3 and 10/7 occasions, respectively. Positive cultures for *A. xilosoxidans* (1), coagulase negative Staphylococci (2) and *A. baumanii* (1) were only found in the study group.

A second intra-abdominal culture was taken during the first week after surgery (Table 7). At this time, the average number of organisms isolated in the control group (24) was almost the same as in the peri-operative sample (29). Importantly, there was a strong reduction in the number of positive samples in the study group. From 30 positive cultures in the peri-operative samples, only one remained positive for *S. aureus* and another one for *E. coli*. In the analysis of hospital days, the control group had a longer stay (31.9 days) in comparison to the study group (22.4 days). Thus, the ORP water solution effectively reduced the peritoneal bacterial load and length of hospital stay in patients with peritonitis.

The mortality rates were also analyzed. There were six deaths in the control group and 3 in the study one. All deaths occurred in the first 30 days after the first surgery and the calculated relative risk was higher for the control group (i.e. 3.3 versus 0). However, the sample size was too small to achieve statistical significance. No local side effects were recorded with the use of ORP water in the IOPL. Surviving patients in the study group were followed for 6 to 12 months. None of the 20 patients in the ORP water-treated group presented intestinal occlusion or data suggesting sclerosing peritonitis in the follow-up period.

EXAMPLE 20

This example demonstrates the effectiveness of an exemplary ORP water solution (Mycrocyn) in inhibiting mast cell degranulation. Mast cells have been recognized as principal players in type I hypersensitivity disorders. Multiple clinical symptoms observed in atopic dermatitis, allergic rhinitis, and atopic asthma are produced by IgE-antigen stimulation of mast cells located in distinct affected tissues. The currently accepted view of the pathogenesis of atopic asthma is that allergens initiate the process by triggering IgE-bearing pulmonary mast cells (MCs) to release mediators such as histamine, leukotrienes, prostaglandins, kininis, platelet activating factor (PAF), etc. in the so-called early phase of the reaction. In turn, these mediators induce bronchoconstriction and enhance vascular permeability and mucus production. According to this model, following mast cell activation, those cells secrete various pro-inflammatory cytokines in a late phase, including tumor necrosis factor alpha (TNF-α), IL-4, IL-5 and IL-6, which participate in the local recruitment and activation of other inflammatory cells such as eosinophils, basophils, T lymphocytes, platelets and mononuclear phagocytes. These recruited cells, in turn, contribute to the development of an inflammatory response that may then become autonomous and aggravate the asthmatic symptoms. This late phase response constitutes a long term inflammation process which can induce plastic changes in surrounding tissues (see Kumar et al., pp. 193-268).

Antigenic stimulation of mast cells occurs via the activation of the high affinity receptor for IgE (the FIERI receptor), which is a multimeric protein that binds IgE and subsequently can be aggregated by the interaction of the receptor-bound IgE with a specific antigen. Its structure comprises four polypeptides, an IgE binding α chain, a β chain that serves to amplify its signaling capacity, and two disulfide-linked γ chains, which are the principal signal transducers via the encoded immunoreceptor tyrosine-based (ITAM) activation motif. Signaling pathways activated by the cross-linking of this receptor have been characterized using bone marrow-derived mast cells (BMMC), the rat leukemia cell line RBL 2H3, mouse and rat peritoneal mast cells, and other mast cell lines, such as MC-9, In all of them, the presence of antigen bound to IgE causes mast cell degranulation, calcium mobilization, cytoskeletal re-arrangements and activation of different transcription factors (NFAT, NFκB, AP-1, PU.1, SP1, Ets, etc.) which activate cytokine gene transcription that culminate with cytokine production.

Figure 7:
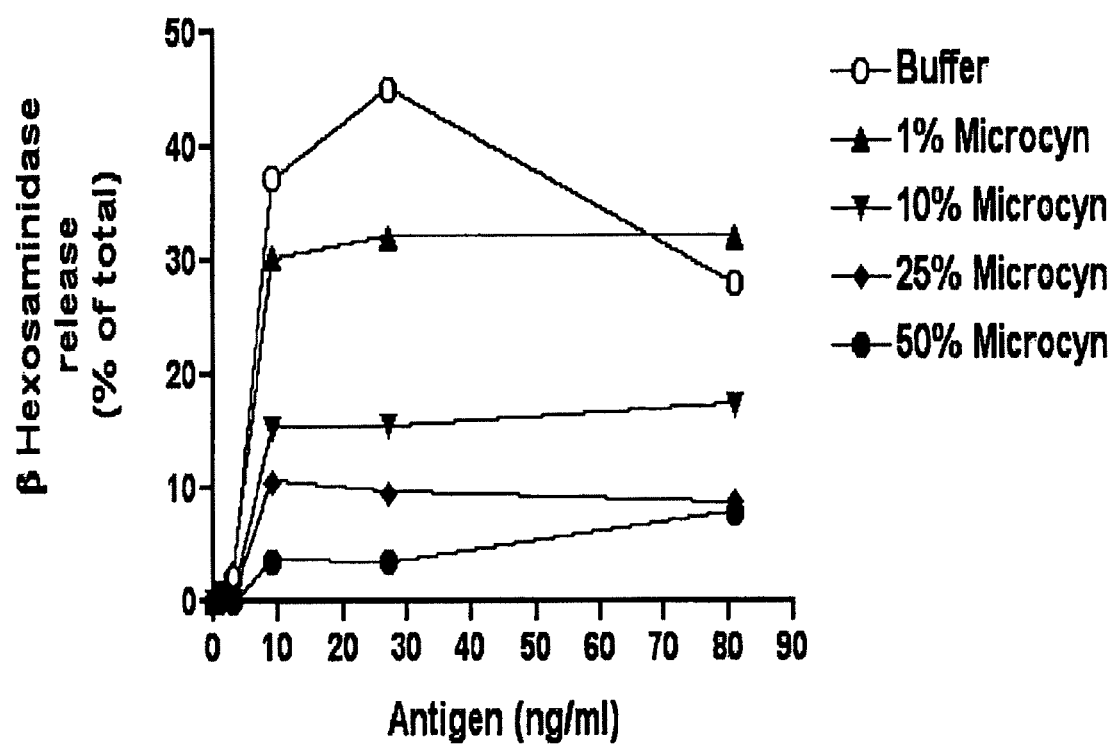
FIG. 7 illustrates the effect on degranulation of antigen-activated mast cells treated with various concentrations of an exemplary ORP water solution (MCN).

Mature murine bone-derived mast cells (BMMC) were loaded with a monoclonal anti-Dinitrophenol IgE (300 ng/million cell) during 4 hours at 37° C. Culture media was removed and cells were resuspended in physiological buffer (Tyrode's Buffer/BSA). Cells were then treated 15 minutes at 37° C. with distinct concentrations of the ORP water solution (in its Microcyn embodiment). Buffer was removed and cells resuspended in fresh Tyrode's/BSA and stimulated with different concentrations of antigen (Human Albumin coupled to Dinitrophenol) during a 30 minute incubation at 37° C. Degranulation was measured by β-hexosaminidase activity determination in supernatants and pellets of the stimulated cells, using a colorimetric reaction based on the capacity of this enzyme to hydrolize distinct carbohydrates. (β-hexosaminidase has been shown to be located in the same granules that contain histamine in mast cells.) The results (FIG. 7) demonstrate that degranulation is significantly reduced with increasing concentrations of the ORP water solution.

Figure 8:
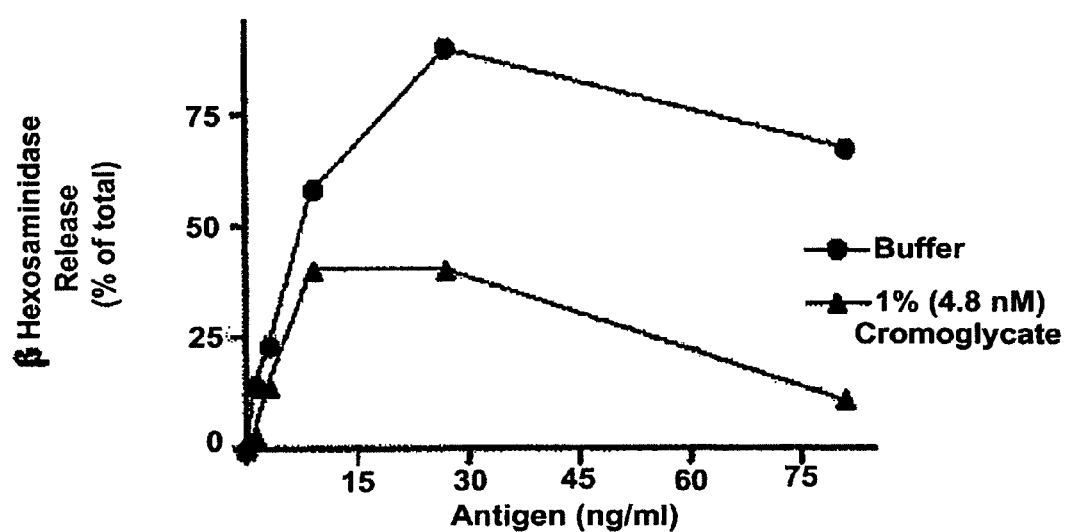
FIG. 8 comparatively illustrates the effect on degranulation of antigen-activated mast cells treated with cromoglycate.
Figure 9:
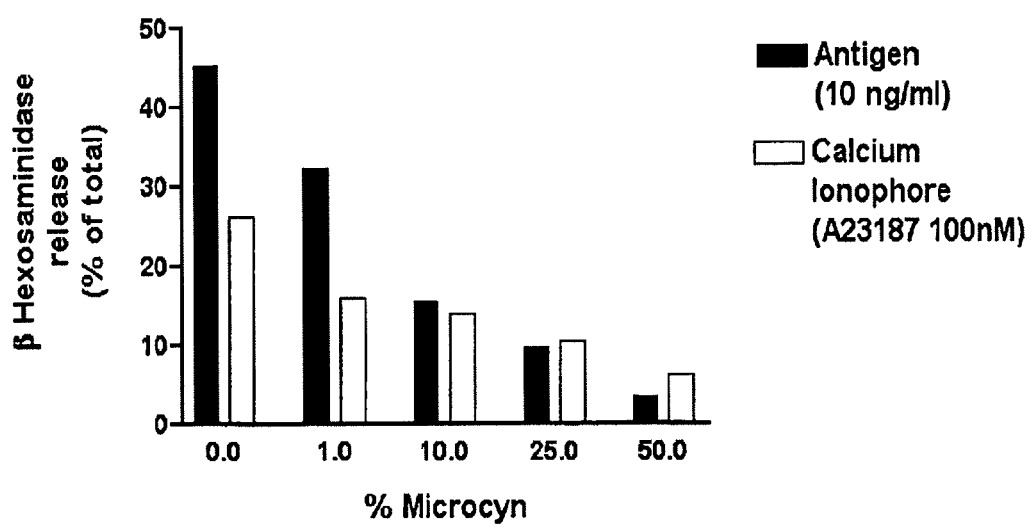
FIG. 9 illustrates the effect on degranulation of antigen-activated and calcium ionophore (A23187)-activated mast cells treated with various concentrations of an exemplary ORP water solution (MCN).

Surprisingly, the inhibitory effect of the ORP water solution (Microcyn) on mast cell degranulation at least is similar to that observed with the clinically effective "mast cell stabilizer" and established anti-allergic compound sodium cromoglycate (Intel™) Degranulation was again measured by β-hexosaminidase enzymatic activity in the pellet and supernatant of stimulated cells, using a colorimetric reaction based on the capacity of this enzyme to hydrolize distinct carbohydrates. Cells loaded with anti-DNP monoclonal IgE were stimulated with or without a 15 minute pre-incubation with sodium cromoglycate (Intel™). Cromoglycate was no more effective than the ORP water solution in reducing degranulations (Compare FIG. 7 with FIG. 8; both achieving at least about 50% reduction in degranulation.)

EXAMPLE 21

This example demonstrates the inhibitory activity of an exemplary ORP water solution on mast cell activation by a calcium ionophore.

Mast cells can be stimulated via the activation of calcium fluxes induced by a calcium ionophore. Signaling pathways activated by calcium ionophores have been characterized using bone marrow-derived mast cells (BMMC), the rat leukemia cell line RBL 2H3, mouse and rat peritoneal mast cells, and other mast cell lines, such as MC-9. In all of these systems the calcium mobilization causes mast cell degranulation (e.g. histamine release), cytoskeletal re-arrangements, and activation of different transcription factors (e.g., NFAT, NFκB, AP-1, PU.1, SP1, Ets.) which activate cytokine gene transcription that culminate with cytokine production and secretion.

Mature murine BMMC were loaded with a monoclonal anti-Dinitrophenol IgE (300 ng/million cell) during 4 hours at 37° C. Culture media was removed and cells were resuspended in physiological buffer (Tyrode's Buffer/BSA). Cells were then treated for 15 minutes at 37° C. with distinct concentrations of the ORP water solution (Microcyn). Buffer was removed and cells were resuspended in fresh Tyrode's/BSA and stimulated with calcium ionophore (100 mM A23187) during a 30 minute incubation at 37° C. Degranulation was measured by β-hexosaminidase activity determination in supernatants and pellets of the stimulated cells, using a colorimetric reaction based on the capacity of this enzyme to hydrolyze distinct carbohydrates. (β-hexosaminidase has been shown to be located in the same granules that contain histamine in mast cells.) The results (FIG. 8) demonstrate that degranulation is significantly reduced with increasing concentrations of the ORP water solution.

These results suggest that ORP water solution is a non-specific inhibitor of histamine release. Thus, ORP water solution—even at different concentrations—will inhibit the degranulation of mast cells independently of the stimulus (e.g. antigen or ionophore). While not desiring to be bound by any theory, ORP water solution probably modifies the secretory pathway system at the level of the plasma membrane and/or cytoskeleton. Because the mechanism of action of ORP water solution is believed to be non-specific, it is believed that ORP water solution can have broad potential clinical applications.

EXAMPLE 22

This example demonstrates the effect of an exemplary ORP water solution on the activation of mast cell cytokine gene transcription.

Figure 10A:
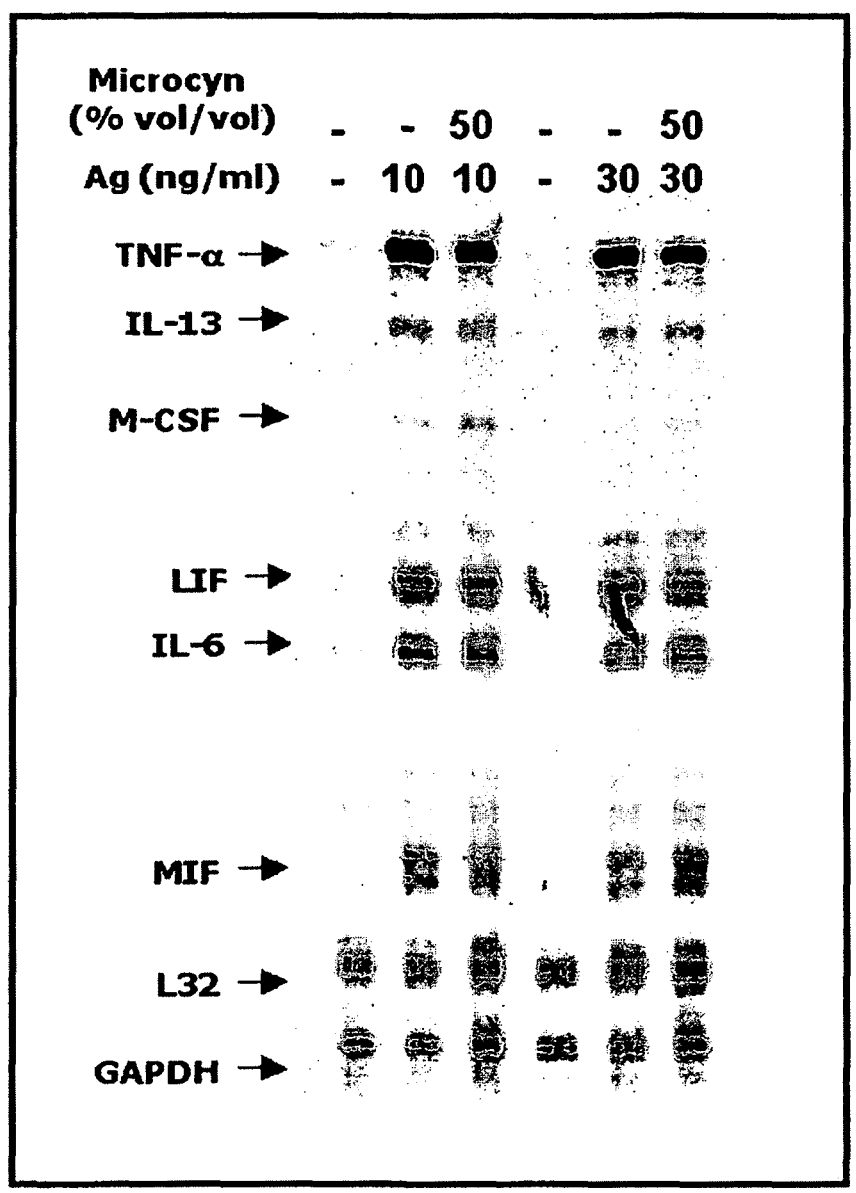
FIG. 10A-10B are RNAse protection assays illustrating cytokine mRNA levels after antigen challenge in control versus ORP water solution-treated mast cells.
Figure 10B:
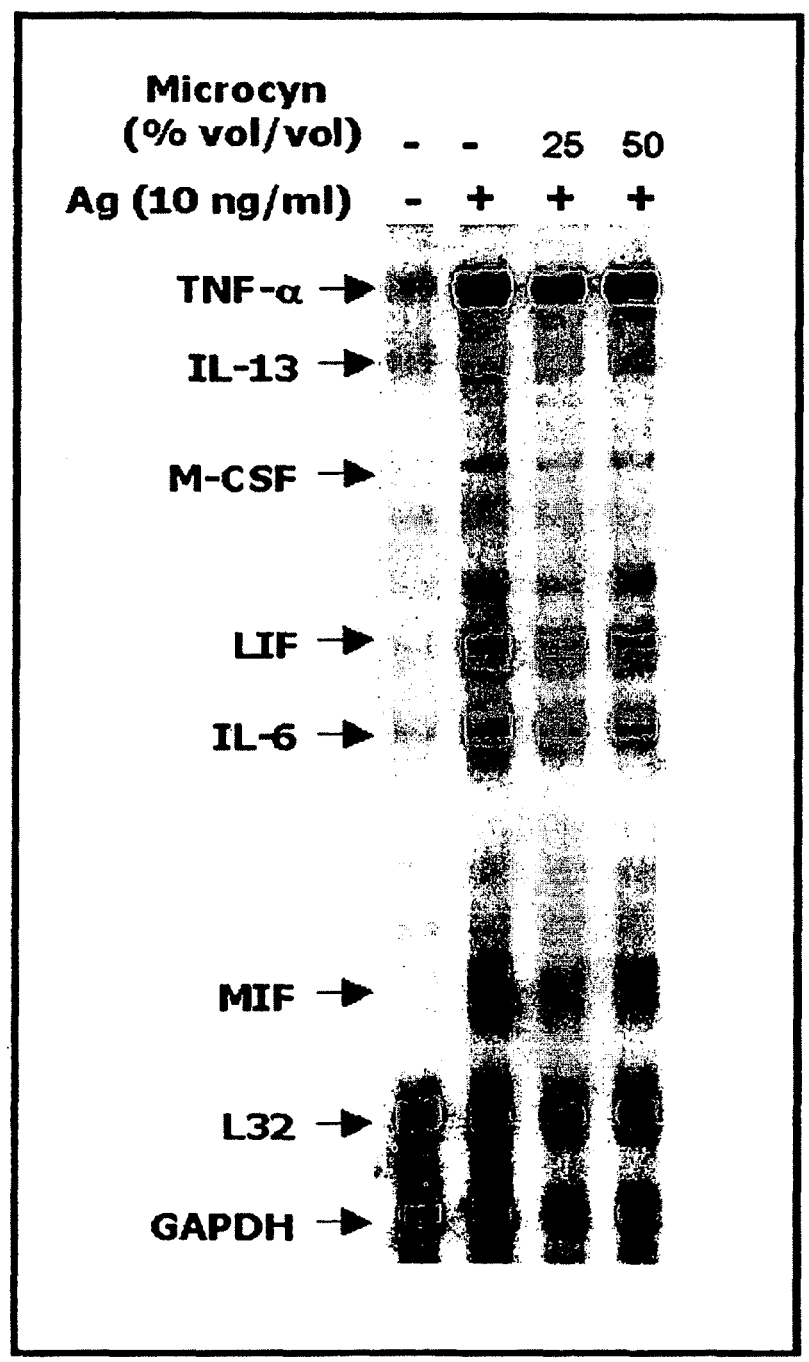

FIGS. 10A and 10B are RNAase protection assays from mast cells treated with ORP water solution at different concentrations for 15 minutes and further stimulated by antigen as described in Example 20. After stimulation, mRNA was extracted using affinity chromatography columns (RNAeasy kit, Qiagene) and the RNAse Protection Assay was performed using standard kit conditions (Clontech, Becton & Dickinson) in order to detect mRNA production of distinct cytokines after antigen challenge. The cytokines included TNF-α, LIF, IL13, M-CSF, IL6, MIF and L32.

FIGS. 10A and 10B show that the ORP solution water (Microcyn) did not modify cytokine mRNA levels after antigen challenge in mast cells irrespective of the concentrations of ORP water solution or antigen used for the experiment.

In this study, the level of transcripts (i.e., the RNA content of stimulated mast cells) of proinflammatory genes was not changed in ORP water solution-treated mast cells after being stimulated with various concentrations of antigen. Thus, the ORP water solution inhibited the secretory pathway of these cytokines without affecting their transcription.

EXAMPLE 23

This example demonstrates the inhibitory activity of an exemplary ORP water solution on mast cell secretion of TNF-α.

Mast cells were treated with different concentrations of ORP water solution for 15 minutes and further stimulated by antigen as described in Example 20, Thereafter, the tissue culture medium was replaced and samples of the fresh medium were collected at various periods of time (2-8 hours) for measuring TNF-α levels. Samples were frozen and further analyzed with a commercial ELISA kit (Biosource) according to the manufacturer's instructions.

Figure 11:
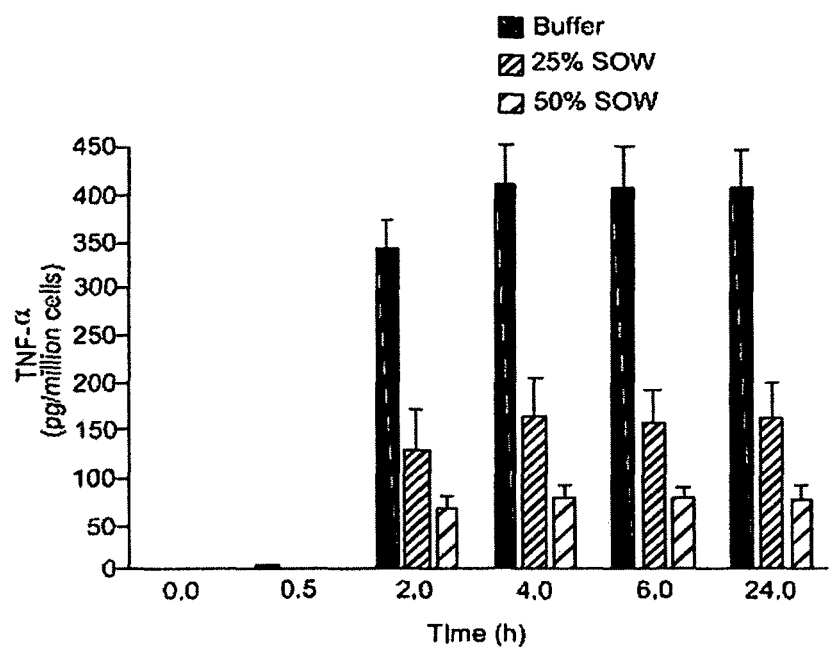
FIG. 11 is a graphical comparison of TNF-α secretion by antigen-activated mast cells treated with various concentrations of an exemplary ORP water solution (MCN).

FIG. 11 shows that the level of secreted TNF-α to the medium from ORP water solution-treated cells after antigen stimulation is significantly decreased in comparison to the untreated cells.

Since the release of TNF-α and that of various other pro-inflammatory molecules depends on a separate secretory pathway than that of histamine, it is possible that the ORP solution can stop the secretion of those other cytokines leading the late inflammatory phase.

Thus, the ORP water solution inhibited TNF-α secretion of antigen-stimulated mast cells. These results are in agreement with clinical observations that the use of ORP water solutions can decrease the inflammatory reaction in various wounds after surgical procedures.

EXAMPLE 24

This example demonstrates the inhibitory activity of an exemplary ORP water solution on mast cell secretion of MIP 1-α.

Mast cells were treated with different concentrations of an exemplary ORP water solution (Microcyn) for 15 minutes and further stimulated by antigen as described in Example 20. Thereafter, the tissue culture medium was replaced and samples of the fresh medium were collected at various periods of time (2-8 hours) for measuring MIP 1-α levels. Samples were frozen and further analyzed with a commercial ELISA kit (Biosource) according to the manufacturer's instructions.

Figure 12:
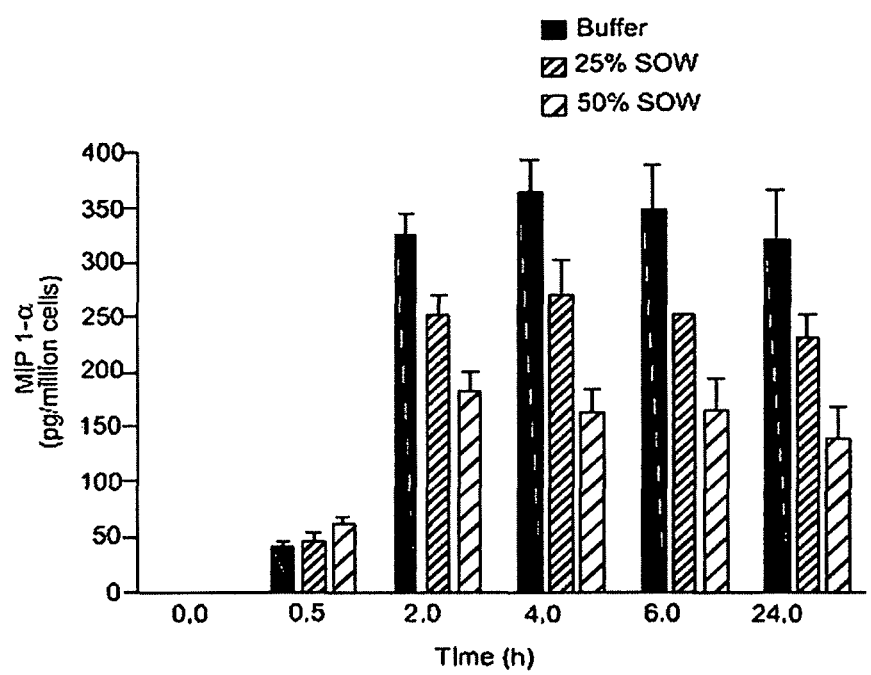
FIG. 12 is a graphical comparison of MIP1-α secretion by antigen-activated mast cells treated with various concentrations of an exemplary ORP water solution (MCN).

FIG. 12 shows that the level of secreted MIP 1-α to the medium from ORP water solution-treated cells after antigen stimulation was significantly decreased in comparison to the untreated cells.

Thus, the ORP water solution inhibited MIP 1-α secretion of antigen-stimulated mast cells. These results are in agreement with clinical observations that the use of ORP water solutions can decrease the inflammatory reaction in various wounds after surgical procedures.

Since the release of MIP 1-α and that of various other pro-inflammatory molecules depends on a separate secretory pathway than that of histamine, it is possible that the ORP solution can stop the secretion of those other cytokines leading the late inflammatory phase.

Figure 13:
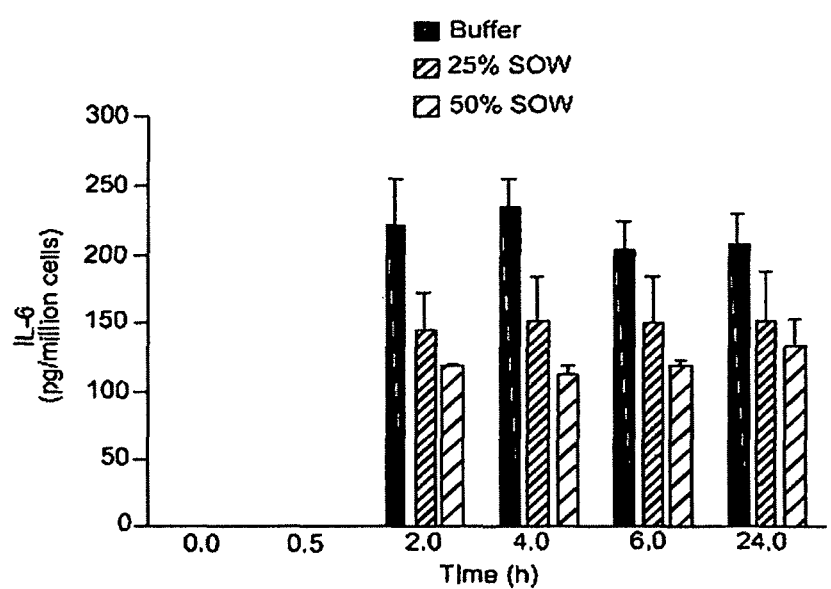
FIG. 13 is a graphical comparison of IL-6 secretion by antigen-activated mast cells treated with various concentrations of an exemplary ORP water solution (MCN).
Figure 14:
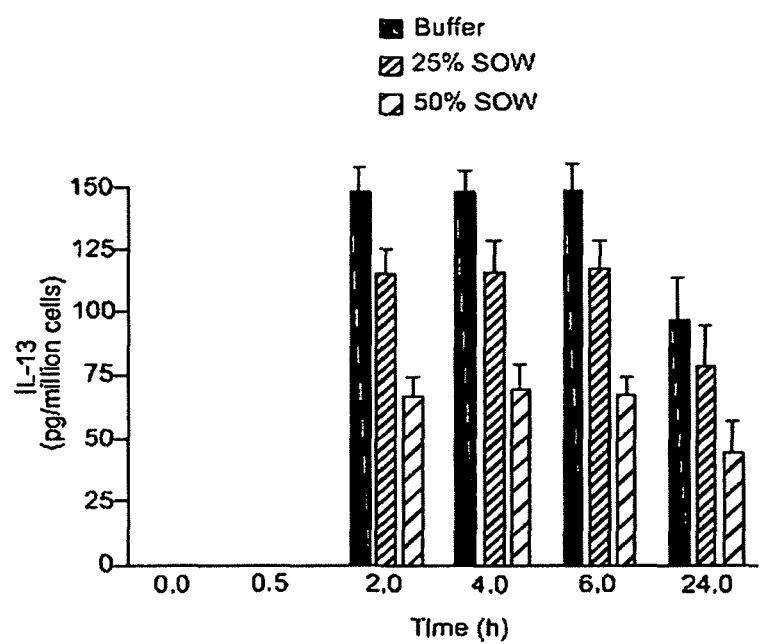
FIG. 14 is a graphical comparison of IL-13 secretion by antigen-activated mast cells treated with various concentrations of an exemplary ORP water solution (MCN).

The results of analogous studies measuring IL-6 and IL-13 secretion are depicted in FIGS. 13 and 14.

Examples 20-23 and this example further demonstrate that the ORP water solution is able to inhibit early and late phase allergic responses initiated by IgE receptor crosslinking.

EXAMPLE 25

This example demonstrates the results of a toxicity study using an exemplary ORP water solution.

An acute systemic toxicity study was performed in mice to determine the potential systemic toxicity of Microcyn 60, an exemplary ORP water solution. A single dose (50 mL/kg) of Microcyn 60 was injected intraperitoneally in five mice. Five control mice were injected with a single dose (50 mL/kg) of saline (0.9% sodium chloride). All animals were observed for mortality and adverse reactions immediately following the injection, at 4 hours after injection, and then once daily for 7 days. All animals were also weighed prior to the injection and again on Day 7. There was no mortality during the study. All animals appeared clinically normal throughout the study. All animals gained weight. The estimated Microcyn 60 acute intraperitoneal LD50 from this study is greater than 50 mL/kg. This example demonstrates that Microcyn 60 lacks significant toxicity and should be safe for therapeutic use accordance with the invention.

EXAMPLE 26

This example illustrates a study conducted to determine the potential cytogenetic toxicity of an exemplary ORP water solution.

A micronucleus test was performed using an exemplary ORP water solution (10% Microcyn™) to evaluate the mutagenic potential of intraperitoneal injection of an ORP water solution into mice. The mammalian in vivo micronucleus test is used for the identification of substances which cause damage to chromosomes or the mitotic apparatus of murine polychromatic erythrocytes. This damage results in the formation of "micronuclei," intracellular structures containing lagging chromosome fragments or isolated whole chromosomes. The ORP water solution study included 3 groups of 10 mice each (5 males/5 females): a test group, dosed with the ORP water solution; a negative control group, dosed with a 0.9% NaCl solution; and a positive control group, dosed with a mutagenic cyclophosphamide solution. The test and the negative control groups received an intraperitoneal injection (12.5 ml/kg) of the ORP water solution or 0.9% NaCl solution, respectively, for two consecutive days (days 1 and 2). The positive control mice received a single intraperitoneal injection of cyclophosphamide (8 mg/mL, 12.5 ml/kg) on day 2. All mice were observed immediately after injection for any adverse reactions. All animals appeared clinically normal throughout the study and no sign of toxicity was noted in any group. On day 3, all mice were weighed and terminated.

The femurs were excised from the terminated mice, the bone marrow was extracted, and duplicate smear preparations were performed for each mouse. The bone marrow slides for each animal were read at 40× magnification. The ratio of polychromatic erythrocytes (PCE) to normochromatic erythrocytes (NCE), an index of bone marrow toxicity, was determined for each mouse by counting a total of at least 200 erythrocytes. Then a minimum of 2000 scoreable PCE per mouse were evaluated for the incidence of micronucleated polychromatic erythrocytes. Statistical analysis of the data were done using the Mann and Whitney test (at 5% risk threshold) from a statistical software package (Statview 5.0®, SAS Institute Inc., USA).

The positive control mice had statistically significant lower PCE/NCE ratios when compared to their respective negative controls (males: 0.77 vs. 0.90 and females: 0.73 vs. 1.02), showing the toxicity of the cyclophosphamide on treated bone marrow. However, there was no statistically significant difference between the PCE/NCE ratios for the ORP water solution-treated mice and negative controls. Similarly, positive control mice had a statistically significant higher number of polychromatic erythrocytes bearing micronuclei as compared to both the ORP water solution-treated mice (males: 11.0 vs. 1.4/females: 12.6 vs. 0.8) and the negative controls (males: 11.0 vs. 0.6/females: 12.6 vs. 1.0). There was no statistically significant difference between the number of polychromatic erythrocytes bearing micronculei in ORP water solution-treated and negative control mice.

This example demonstrates that Microcyn™ 10% did not induce toxicity or mutagenic effects after intraperitoneal injections into mice.

EXAMPLE 27

This study demonstrates the lack of toxicity of an exemplary ORP water solution, Dermacyn.

This study was done in accordance with ISO 10993-5: 1999 standard to determine the potential of an exemplary ORP water solution, Dermacyn, to cause cytotoxicity. A filter disc with 0.1 mL of Dermacyn was placed onto an agarose surface, directly overlaying a monolayer of mouse fibroblast cells (L-929). The prepared samples were observed for cytotoxic damage after 24 hours of incubation at 37° C. in the presence of 5% $CO_2$. Observations were compared to positive and negative control samples. The Dermacyn containing samples did not reveal any evidence of cell lysis or toxicity, while positive and negative control performed as anticipated.

Based on this study Dermacyn was concluded not to generate cytotoxic effects on murine fibroblasts.

EXAMPLE 28

This study was conducted with 16 rats to evaluate the local tolerability of an exemplary ORP water solution, Dermacyn, and its effects on the histopathology of wound beds in a model of full-thickness dermal wound healing. Wounds were made on both sides of the subject rat. During the healing process skin sections were taken on either the left or the right sides (e.g., Dermacyn-treated and saline-treated, respectively).

Masson's trichrome-stained sections and Collagen Type II stained sections of the Dermacyn and saline-treated surgical wound sites were evaluated by a board-certified veterinary pathologist. The sections were assessed for the amount of Collagen Type 2 expression as a manifestiation of connective tissue proliferation, fibroblast morphology and collagen formation, presence of neoepidermis in cross section, inflammation and extent of dermal ulceration.

The findings indicate that Dermacyn was well tolerated in rats. There were no treatment-related histopathologic lesions in the skin sections from either sides' wounds (Dermacyn-treated and saline-treated, respectively). There were no relevant histopathologic differences between the saline-treated and the Dermacyn-treated wound sites, indicating that the Dermacyn-treatement was well tolerated. There were no significant differences between Collagen Type 2 expression between the saline-treated and the Dermacyn™-treated wound sites indicating that the Dermacyn does not have an adverse effect on fibroblasts or on collagen elaboration during wound healing.

EXAMPLE 29

This example demonstrates the use of an exemplary oxidative reductive potential water, Microcyn, in accordance with the invention as an effective antimicrobial solution.

An In-Vitro Time-Kill evaluation was performed using Microcyn oxidative reductive potential water. Microcyn was evaluated versus challenge suspensions of fifty different microorganism strains—twenty-five American Type Culture Collection (ATCC) strains and twenty-five Clinical Isolates of those same species—as described in the Tentative Final Monograph, Federal Register, 17 Jun. 1994, vol. 59:116, pg. 31444. The percent reductions and the $Log_{10}$ reductions from the initial population of each challenge strain were determined following exposures to Microcyn for thirty (30) seconds, one (1) minute, three (3) minutes, five (5) minutes, seven (7) minutes, nine (9) minutes, eleven (11) minutes, thirteen (13) minutes, fifteen (15) minutes, and twenty (20) minutes. All agar-plating was performed in duplicate and Microcyn was evaluated at a 99% (v/v) concentration. All testing was performed in accordance with Good Laboratory Practices, as specified in 21 C.F.R. Part 58.

The following table summarizes the results of the above-mentioned In-Vitro Time-Kill evaluation at the thirty second exposure mark for all populations tested which were reduced by more than 5.0 $Log_{10}$:

TABLE 8

30-Second In-Vitro Kill.

| No. | Microorganism Species | Initial Population (CFU/mL) | Post-Exposure Population (CFU/mL) | $\text{Log}_{10}$ Reduction | Percent Reduction |
|---|---|---|---|---|---|
| 1 | Acinetobacter baumannii (ATCC #19003) | $2.340 \times 10^9$ | $<1.00 \times 10^3$ | 6.3692 | 99.9999 |
| 2 | Acinetobacter baumannii Clinical Isolate BSLI #061901Ab3 | $1.8150 \times 10^9$ | $<1.00 \times 10^3$ | 6.2589 | 99.9999 |
| 3 | Bacteroides fragilis (ATCC #43858) | $4.40 \times 10^{10}$ | $<1.00 \times 10^3$ | 7.6435 | 99.9999 |
| 4 | Bacteroides fragilis Clinical Isolate BSLI #061901Bf6 | $2.70 \times 10^{10}$ | $<1.00 \times 10^3$ | 7.4314 | 99.9999 |
| 5 | Candida albicans (ATCC #10231) | $2.70 \times 10^{10}$ | $<1.00 \times 10^3$ | 6.3345 | 99.9999 |
| 6 | Candida albicans Clinical Isolate BSLI #042905Ca | $5.650 \times 10^9$ | $<1.00 \times 10^3$ | 6.7520 | 99.9999 |
| 7 | Enterobacter aerogenes (ATCC #29007) | $1.2250 \times 10^9$ | $<1.00 \times 10^3$ | 6.0881 | 99.9999 |
| 8 | Enterobacter aerogenes Clinical Isolate BSLI #042905Ea | $1.0150 \times 10^9$ | $<1.00 \times 10^3$ | 6.0065 | 99.9999 |
| 9 | Enterococcus faecalis (ATCC #29212) | $2.610 \times 10^9$ | $<1.00 \times 10^3$ | 6.4166 | 99.9999 |
| 10 | Enterococcus faecalis Clinical Isolate BSLI #061901Efs2 | $1.2850 \times 10^9$ | $<1.00 \times 10^3$ | 6.1089 | 99.9999 |
| 11 | Enterococcus faecium VRE, MDR (ATCC #51559) | $3.250 \times 10^9$ | $<1.00 \times 10^3$ | 6.5119 | 99.9999 |
| 12 | Enterococcus faecium Clinical Isolate BSLI #061901Efm1 | $1.130 \times 10^9$ | $<1.00 \times 10^3$ | 6.0531 | 99.9999 |
| 13 | Escherichia coli (ATCC #11229) | $5.00 \times 10^8$ | $<1.00 \times 10^3$ | 5.6990 | 99.9998 |
| 14 | Escherichia coli Clinical Isolate BSLI #042905Ec1 | $3.950 \times 10^8$ | $<1.00 \times 10^3$ | 5.5966 | 99.9997 |
| 15 | Escherichia coli (ATCC #25922) | $6.650 \times 10^8$ | $<1.00 \times 10^3$ | 5.8228 | 99.9998 |
| 16 | Escherichia coli Clinical Isolate BSLI #042905Ec2 | $7.40 \times 10^8$ | $<1.00 \times 10^3$ | 5.8692 | 99.9998 |
| 17 | Haemophilus influenzae (ATCC #8149) | $1.5050 \times 10^9$ | $<1.00 \times 10^4$ | 5.1775 | 99.9993 |
| 18 | Haemophilus influenzae Clinical Isolate BSLI #072605Hi | $1.90 \times 10^9$ | $<1.00 \times 10^4$ | 5.2788 | 99.9995 |
| 19 | Klebsiella oxytoca MDR (ATCC #15764) | $1.120 \times 10^9$ | $<1.00 \times 10^3$ | 6.0492 | 99.9999 |
| 20 | Klebsiella oxytoca Clinical Isolate BSLI #061901Ko1 | $1.810 \times 10^9$ | $<1.00 \times 10^3$ | 6.2577 | 99.9999 |
| 21 | Klebsiella pneumoniae subsp. ozaenae (ATCC #29019) | $1.390 \times 10^9$ | $<1.00 \times 10^3$ | 6.1430 | 99.9999 |
| 22 | Klebsiella pneumoniae Clinical Isolate BSLI #061901Kpn2 | $9.950 \times 10^8$ | $<1.00 \times 10^3$ | 5.9978 | 99.9999 |
| 23 | Micrococcus luteus (ATCC #7468) | $6.950 \times 10^8$ | $<1.00 \times 10^3$ | 5.8420 | 99.9999 |
| 24 | Micrococcus luteus Clinical Isolate BSLI #061901Ml2 | $1.5150 \times 10^9$ | $<1.00 \times 10^3$ | 6.1804 | 99.9999 |
| 25 | Proteus mirabilis (ATCC #7002) | $1.5950 \times 10^9$ | $<1.00 \times 10^3$ | 6.2028 | 99.9999 |
| 26 | Proteus mirabilis Clinical Isolate BSLI #061901Pm2 | $2.0950 \times 10^9$ | $<1.00 \times 10^3$ | 6.3212 | 99.9999 |
| 27 | Pseudomonas aeruginosa (ATCC #15442) | $6.450 \times 10^8$ | $<1.00 \times 10^3$ | 5.8096 | 99.9999 |
| 28 | Pseudomonas aeruginosa Clinical Isolate BSLI #072605Pa | $1.3850 \times 10^9$ | $<1.00 \times 10^3$ | 6.1414 | 99.9999 |

TABLE 8-continued

30-Second In-Vitro Kill.

| No. | Microorganism Species | Initial Population (CFU/mL) | Post-Exposure Population (CFU/mL) | $\text{Log}_{10}$ Reduction | Percent Reduction |
|---|---|---|---|---|---|
| 29 | *Pseudomonas aeruginosa* (ATCC #27853) | $5.550 \times 10^8$ | $<1.00 \times 10^3$ | 5.7443 | 99.9999 |
| 30 | *Pseudomonas aeruginosa* Clinical Isolate BSLI #061901Pa2 | $1.1650 \times 10^9$ | $<1.00 \times 10^3$ | 6.0663 | 99.9999 |
| 31 | *Serratia marcescens* (ATCC #14756) | $9.950 \times 10^8$ | $<1.00 \times 10^3$ | 5.9978 | 99.9999 |
| 32 | *Serratia marcescens* Clinical Isolate BSLI #042905Sm | $3.6650 \times 10^9$ | $<1.00 \times 10^3$ | 6.5641 | 99.9999 |
| 33 | *Staphylococcus aureus* (ATCC #6538) | $1.5050 \times 10^9$ | $<1.00 \times 10^3$ | 6.1775 | 99.9999 |
| 34 | *Staphylococcus aureus* Clinical Isolate BSLI #061901Sa1 | $1.250 \times 10^9$ | $<1.00 \times 10^3$ | 6.0969 | 99.9999 |
| 35 | *Staphylococcus aureus* (ATCC #29213) | $1.740 \times 10^9$ | $<1.00 \times 10^3$ | 6.2405 | 99.9999 |
| 36 | *Staphylococcus aureus* Clinical Isolate BSLI #061901Sa2 | $1.1050 \times 10^9$ | $<1.00 \times 10^3$ | 6.0434 | 99.9999 |
| 37 | *Staphylococcus epidermidis* (ATCC #12228) | $1.0550 \times 10^9$ | $<1.00 \times 10^3$ | 6.0233 | 99.9999 |
| 38 | *Staphylococcus epidermidis* Clinical Isolate BSLI #072605Se | $4.350 \times 10^8$ | $<1.00 \times 10^3$ | 5.6385 | 99.9998 |
| 39 | *Staphylococcus haemolyticus* (ATCC #29970) | $8.150 \times 10^8$ | $<1.00 \times 10^3$ | 5.9112 | 99.9999 |
| 40 | *Staphylococcus haemolyticus* Clinical Isolate BSLI #042905Sha | $8.350 \times 10^8$ | $<1.00 \times 10^3$ | 5.9217 | 99.9999 |
| 41 | *Staphylococcus hominis* (ATCC #27844) | $2.790 \times 10^8$ | $<1.00 \times 10^3$ | 5.4456 | 99.9996 |
| 42 | *Staphylococcus hominis* Clinical Isolate BSLI #042905Sho | $5.20 \times 10^8$ | $<1.00 \times 10^3$ | 5.7160 | 99.9998 |
| 43 | *Staphylococcus saprophyticus* (ATCC #35552) | $9.10 \times 10^8$ | $<1.00 \times 10^3$ | 5.9590 | 99.9999 |
| 44 | *Staphylococcus saprophyticus* Clinical Isolate BSLI #042905Ss | $1.4150 \times 10^9$ | $<1.00 \times 10^3$ | 6.1508 | 99.9999 |
| 45 | *Streptococcus pneumoniae* (ATCC #33400) | $2.1450 \times 10^9$ | $<1.00 \times 10^4$ | 5.3314 | 99.9995 |
| 46 | *Streptococcus pyogenes* (ATCC #19615) | $5.20 \times 10^9$ | $<1.00 \times 10^3$ | 6.7160 | 99.9999 |
| 47 | *Streptococcus pyogenes* Clinical Isolate BSLI #061901Spy7 | $2.5920 \times 10^9$ | $<1.00 \times 10^3$ | 6.4141 | 99.9999 |

While their microbial reductions were measured at less than 5.0 $\text{Log}_{10}$, Microcyn also demonstrated antimicrobial activity against the remaining three species not included in Table 8. More specifically, a thirty second exposure to Microcyn reduced the population of *Streptococcus pneumoniae* (Clinical Isolate; BSLI #072605Spn1) by more than 4.5 $\text{Log}_{10}$, which was the limit of detection versus this species. Further, when challenged with *Candida tropicalis* (ATCC #750), Microcyn demonstrated a microbial reduction in excess of 3.0 $\text{Log}_{10}$ following a thirty second exposure. Additionally, when challenged with *Candida tropicalis* (BSLI #042905Ct), Microcyn demonstrated a microbial reduction in excess of 3.0 $\text{Log}_{10}$ following a twenty minute exposure.

The exemplary results of this In-Vitro Time-Kill evaluation demonstrate that Microcyn oxidative reductive potential water exhibits rapid (i.e., less than 30 seconds in most cases) antimicrobial activity versus a broad spectrum of challenging microorganisms. Microbial populations of forty-seven out of the fifty Gram-positive, Gram-negative, and yeast species evaluated were reduced by more than 5.0 $\text{Log}_{10}$ within thirty seconds of exposure to the product.

EXAMPLE 30

This example demonstrates a comparison of the antimicrobial activity of an exemplary oxidative reductive potential water, Microcyn, used in accordance with the invention versus HIBICLENS® chlorhexidine gluconate solution 4.0% (w/v) and 0.9% sodium chloride irrigation (USP).

An In-Vitro Time-Kill evaluation was performed as described in Example 29 using HIBICLENS® chlorhexidine gluconate solution 4.0% (w/v) and a sterile 0.9% sodium chloride irrigation solution (USP) as reference products. Each reference product was evaluated versus suspensions of the ten American Type Culture Collection (ATCC) strains specifically denoted in the Tentative Final Monograph. The data collected was then analyzed against the Microcyn microbial reduction activity recorded in Example 29.

Microcyn oxidative reductive potential water reduced microbial populations of five of the challenge strains to a level comparable to that observed for the HIBICLENS® chlorhexidine gluconate solution. Both Microcyn and HIBICLENS® provided a microbial reduction of more than 5.0 $Log_{10}$ following a thirty second exposure to the following species: *Escherichia coli* (ATCC #11229 and ATCC #25922), *Pseudomonas aeruginosa* (ATCC #15442 and ATCC #27853), and *Serratia* marcescens (ATCC #14756). Further, as shown above in Table 9, Microcyn demonstrated excellent antimicrobial activity against *Micrococcus luteus* (ATCC #7468) by providing a 5.8420 $Log_{10}$ reduction after a thirty second exposure. However, a direct *Micrococcus luteus* (ATCC #7468) activity comparison to HIBICLENS® was not possible because after a thirty second exposure, HIBICLENS® reduced the population by the detection limit of the test (in this specific case, by more than 4.8 $Log_{10}$). It is noted that the sterile 0.9% sodium chloride irrigation solution reduced microbial populations of each of the six challenge strains discussed above by less than 0.3 $Log_{10}$ following a full twenty minute exposure.

Microcyn oxidative reductive potential water provided greater antimicrobial activity than both HIBICLENS® and the sodium chloride irrigation for four of the challenge strains tested: *Enterococcus faecalis* (ATCC #29212), *Staphylococcus aureus* (ATCC #6538 and ATCC #29213), and *Staphylococcus epidermidis* (ATCC #12228). The following table summarizes the microbial reduction results of the In-Vitro Time-Kill evaluation for these four species:

TABLE 9

Comparative Results

| Microorganism Species | Exposure Time | $Log_{10}$ Reduction Microcyn | HIBICLENS ® | NaCl Irrigation |
|---|---|---|---|---|
| *Enterococcus faecalis* (ATCC #29212) | 30 seconds | 6.4166 | 1.6004 | 0.3180 |
| | 1 minute | 6.4166 | 2.4648 | 0.2478 |
| | 3 minutes | 6.4166 | 5.2405 | 0.2376 |
| | 5 minutes | 6.4166 | 5.4166 | 0.2305 |
| | 7 minutes | 6.4166 | 5.4166 | 0.2736 |
| | 9 minutes | 6.4166 | 5.4166 | 0.2895 |
| | 11 minutes | 6.4166 | 5.4166 | 0.2221 |
| | 13 minutes | 6.4166 | 5.4166 | 0.2783 |
| | 15 minutes | 6.4166 | 5.4166 | 0.2098 |
| | 20 minutes | 6.4166 | 5.4166 | 0.2847 |
| *Staphylococcus aureus* (ATCC #6538) | 30 seconds | 6.1775 | 1.1130 | 0.0000 |
| | 1 minute | 6.1775 | 1.7650 | 0.0191 |
| | 3 minutes | 6.1775 | 4.3024 | 0.0000 |
| | 5 minutes | 6.1775 | 5.1775 | 0.0000 |
| | 7 minutes | 6.1775 | 5.1775 | 0.0000 |
| | 9 minutes | 6.1775 | 5.1775 | 0.0000 |
| | 11 minutes | 6.1775 | 5.1775 | 0.0267 |
| | 13 minutes | 6.1775 | 5.1775 | 0.0000 |
| | 15 minutes | 6.1775 | 5.1775 | 0.0191 |
| | 20 minutes | 6.1775 | 5.1775 | 0.0000 |
| *Staphylococcus aureus* (ATCC #29213) | 30 seconds | 6.2405 | 0.9309 | 0.0000 |
| | 1 minute | 6.2405 | 1.6173 | 0.0000 |
| | 3 minutes | 6.2405 | 3.8091 | 0.0460 |
| | 5 minutes | 6.2405 | 5.2405 | 0.0139 |
| | 7 minutes | 6.2405 | 5.2405 | 0.0000 |
| | 9 minutes | 6.2405 | 5.2405 | 0.0113 |
| | 11 minutes | 6.2405 | 5.2405 | 0.0283 |
| | 13 minutes | 6.2405 | 5.2405 | 0.0000 |
| | 15 minutes | 6.2405 | 5.2405 | 0.0000 |
| | 20 minutes | 6.2405 | 5.2405 | 0.0615 |
| *Staphylococcus epidermidis* (ATCC #12228) | 30 seconds | 5.6385 | 5.0233 | 0.0456 |
| | 1 minute | 5.6385 | 5.0233 | 0.0410 |
| | 3 minutes | 5.6385 | 5.0233 | 0.0715 |
| | 5 minutes | 5.6385 | 5.0233 | 0.0888 |
| | 7 minutes | 5.6385 | 5.0233 | 0.0063 |
| | 9 minutes | 5.6385 | 5.0233 | 0.0643 |
| | 11 minutes | 5.6385 | 5.0233 | 0.0211 |
| | 13 minutes | 5.6385 | 5.0233 | 0.1121 |
| | 15 minutes | 5.6385 | 5.0233 | 0.0321 |
| | 20 minutes | 5.6385 | 5.0233 | 0.1042 |

The results of this comparative In-Vitro Time-Kill evaluation demonstrate that Microcyn oxidative reductive potential water not only exhibits comparable antimicrobial activity to HIBICLENS® against *Escherichia coli* (ATCC #11229 and ATCC #25922), *Pseudomonas aeruginosa* (ATCC #15442 and ATCC #27853), *Serratia* marcescens (ATCC #14756), and *Micrococcus luteus* (ATCC #7468), but provides more effective treatment against *Enterococcus faecalis* (ATCC #29212), *Staphylococcus aureus* (ATCC #6538 and ATCC #29213), and *Staphylococcus epidermidis* (ATCC #12228). As shown in Table 9, Microcyn exemplifies a more rapid antimicrobial response (i.e., less than 30 seconds) in some species. Moreover, exposure to Microcyn results in a greater overall microbial reduction in all species listed in Table 9.

EXAMPLE 31

This example demonstrates the effectiveness of an ORP water solution against Penicillin Resistant *Streptococcus pneumoniae* (ATCC 51915).

A culture of *Streptococcus pneumoniae* was prepared by using a frozen culture to inoculate multiple BAP plates and incubating for 2-3 days at 35-37° C. with CO2. Following incubation 3-7 mL of sterile diluent/medium was transferred to each agar plate and swabbed to suspend the organism. The suspensions from all plates were collected and transferred to a sterile tube and compared to a 4.0 McFarland Standard. The suspension was filtered through sterile gauze and vortex mixed prior to use in the testing procedure.

An inoculum of 0.1 ml of the organism suspension was added to 49.9 ml of the Microcyn or control substance. At each exposure period, the test mixture was mixed by swirling. The test mixture was exposed for 15 seconds, 30 seconds, 60 seconds, 120 seconds, 5 minutes, and 15 minutes at 25.0° C.

A 1.0 ml sample was removed from the test mixture and added to 9.0 ml of neutralizer representing a 100 dilution of the neutralized inoculated test mixture. A 5 ml aliquot of the 100 neutralized inoculated test mixture was transferred to a 0.45 microliter filter apparatus pre-wetted with 10 ml of Butterfield's Buffer. The filter was rinsed with approximately 50 mL of Butterfield's Buffer, aseptically removed from the apparatus, and transferred to a BAP plate. Additional 1:10 serial dilutions were prepared and one (1.0) ml aliquots of the 10-3-10-4 dilutions of neutralized inoculated test mixture were plated in duplicate on BAP.

The bacterial subculture plates were incubated for 48±4 hours at 35-37° C. in CO2. Subculture plates were refrigerated for two days at 2-8° C. prior to examination. Following incubation and storage, the agar plates were observed visually for the presence of growth. The colony forming units were enumerated and the number of survivors at each exposure time was determined. Representative subcultures demonstrating growth were appropriately examined for confirmation of the test organisms.

The exemplary ORP water solution, Microcyn, demonstrated a >99.93197279% reduction of Penicillin Resistant *Streptococcus pneumoniae* (ATCC 51915) after 15 second, 30 second, 60 second, 120 second, 5 minute, and 15 minute contact times at 25.0° C.

EXAMPLE 32

The objective of this Example is to determine the microbial activity of an exemplary ORP water solution (Dermacyn) versus Bacitracin using a bacterial suspension assay.

Dermacyn is a ready to use product, therefore performing dilutions during testing was not required. Bacitracin is a concentrated re-hydrated solution requiring a dilution to 33 Units/ml.

A purchased spore suspension of *B. atropheus* at $2.5 \times 10^7$/ml was used for testing. In addition fresh suspensions of *Pseudomonas aeruginosa*, and *Staphylococcus aureus* were prepared and measured using a spectrophotometer to ensure the titer was acceptable Nine microliters of test substance was added to 100 ul of microbe suspension. The test mixture was held at 20° C. for the contact times of 20 seconds, 5 minutes, and 20 minutes. 1.0 ml of the test mixture (entire mixture) was added to 9.0 ml of neutralizer for 20 minutes (this is the original neutralization tube or ONT) 1.0 ml of the neutralized test mixture was plated on Tryptic Soy Agar in duplicate for the 5 minute and 20 minute contact times. Additional dilutions and spread plates were used for the 20 second time point, to achieve countable plates.

All plates were incubated at 30° C.-35° C. for a total of 3 days and were evaluated after each day of incubation. To determine the number of microbes exposed to Dermacyn and Bacitracin during testing the suspensions Four 10-fold dilutions were performed and 1.0 ml of the final 2 dilutions was plated in duplicate, where applicable.

Dermacyn when challenged with the test organisms showed total eradication (>4 log reduction) of the vegetative bacteria at all time points and for spores at the 5, and 20 minute time points. Bacitracin only produced approximately 1 log reduction. Microcyn at the 20 second time point showed some reduction in spores. Bacitracin showed no evidence of lowering the bacterial or spore populations over the time periods tested.

EXAMPLE 33

This example demonstrates the effectiveness of two exemplary ORP water solutions (M1 and M2) against bacteria in biofilms.

The parental strain for all studies is *P. aeruginosa* PAO1. All planktonic strains were grown aerobically in minimal medium (2.56 g $Na_2HPO_4$, 2.08 g $KH_2PO_4$, 1.0 g $NH_4Cl$, 0.04 g $CaCl_2.2H_2O$, 0.5 g $MgSO_4.7H_2O$, 0.1 mg $CuSO_4.5H_2O$, 0.1 mg $ZnSO_4.H_2O$, 0.1 mg $FeSO_4.7H_2O$, and 0.004 mg $MnCl_2.4H_2O$ per liter, pH 7.2) at 22° C. in shake flasks at 220 rpm. Biofilms were grown as described below at 22° C. in minimal medium. Glutamate (130 mg/liter) was used as the sole carbon source.

Biofilms were grown as described previously (Sauer et. al., J. Bacteriol. 184:1140-1154 (2002), which is hereby incorporated by reference). Briefly, the interior surfaces of silicone tubing of a once-through continuous flow tube reactor system were used to cultivate biofilms at 22° C. Biofilms were harvested after 3 days (maturation-1 stage), 6 days (maturation—2 stage), and 9 days (dispersion stage) of growth under flowing conditions. Biofilm cells were harvested from the interior surface by pinching the tube along its entire length, resulting in extrusion of the cell material from the lumen. The resulting cell paste was collected on ice. Prior to sampling, the bulk liquid was purged from the tubing to prevent interference from detached, planktonic cells.

The population size of planktonic and biofilm cells was determined by the number of CFU by using serial dilution plate counts. To do so, biofilms were harvested from the interior surface after various periods of time of exposure to SOSs. Images of biofilms grown in once-through flow cells were viewed by transmitted light with an Olympus BX60 microscope (Olympus, Melville, N.Y.) and a 100 magnification A100 PL objective lens. Images were captured using a Magnafire cooled three-chip charge-coupled device camera (Optronics Inc., Galena, Calif.) and a 30-ms exposure. In addition, confocal scanning laser microscopy was performed with an LSM 510 Meta inverted microscope (Zeiss, Heidelberg, Germany). Images were obtained with a LD-Apochrome 40_/0.6 lens and with the LSM 510 Meta software (Zeiss).

A 2-log reduction was observed for M1-treated biofilms within 60 min of treatment. The finding indicates that every 10.8 min (+/−2.8 min), treatment with M1 results in a 50% reduction in biofilm viability.

TABLE 10

| M1 Killing. | |
|---|---|
| Time (min) | Viability (%) |
| 0 | 100 |
| 10 | 50 |
| 20 | 25 |
| 34 | 12.5 |
| 47 | 6.25 |
| 54 | 3.125 |

However, overall M2 was somewhat more effective in killing biofilms than M1 because the results indicated that every 4.0 min (+/−1.2 min), treatment with M2 results in a 50% reduction in biofilm viability.

TABLE 11

| M2 Killing. | |
|---|---|
| Time (min) | Viability (%) |
| 0 | 100 |
| 2.5 | 50 |
| 7 | 25 |
| 12 | 12.5 |
| 15 | 6.25 |
| 20 | 3.125 |

Thus, ORP water is effective against bacteria in biofilms.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of treating atopic dermatitis in a patient, the method comprising administering to the patient a therapeutically effective amount of an oxidative reductive potential water solution, wherein the solution is stable for at least two months and the solution has a pH of from about 6.4 to about 7.8, wherein the oxidative reductive potential water solution comprises a mixture of cathode water and anode water, wherein the oxidative reductive potential water solution comprises free chlorine species at a level of about 10 ppm to about 400 ppm, wherein the free chlorine species is selected from the group consisting of hypochlorous acid, hypochlorite ions, sodium hypochlorite, chlorite ions, dissolved chlorine gas, and mixtures thereof, wherein the oxidative reductive potential water solution inhibits mast cell degranulation, thereby treating the atopic dermatitis wherein the oxidative reductive potential water solution does not contain an antibiotic.

2. The method of claim 1, wherein the oxidative reductive potential water solution is administered topically to cutaneous tissue or subcutaneous tissue.

3. The method of claim 1, wherein the oxidative reductive potential water solution is administered as a liquid, steam, aerosol, mist or spray.

4. The method of claim 1, wherein the oxidative reductive potential water solution is administered by aerosolization, nebulization or atomization.

5. The method of claim 1, wherein the atopic dermatitis is caused by an autoimmune reaction.

6. The method of claim 1, wherein the atopic dermatitis is caused by an infection.

7. The method of claim 6, wherein the infection is by one or more microorganisms selected from the group consisting of viruses, bacteria, and fungi.

8. The method of claim 1, wherein the oxidative reductive potential water solution is stable for at least six months.

9. The method of claim 1, wherein the oxidative reductive potential water solution is stable for at least one year.

10. The method of claim 1, wherein the pH of the oxidative reductive potential water solution is from about 7.4 to about 7.6.

11. The method of claim 1, wherein the oxidative reductive potential water solution comprises from about 10% by volume to about 50% by volume of cathode water and from about 50% by volume to about 90% by volume of anode water.

12. The method of claim 1, wherein the oxidative reductive potential water solution comprises from about 15 ppm to about 35 ppm hypochlorous acid, from about 25 ppm to about 50 ppm sodium hypochlorite, a pH of from about 6.2 to about 7.8, and the solution is stable for at least two months.

13. The method of claim 1, wherein the oxidative reductive potential water solution has a potential between about −400 mV and about +1300 mV.

* * * * *